US006132961A

United States Patent [19]
Gray et al.

[11] Patent Number: 6,132,961
[45] Date of Patent: *Oct. 17, 2000

[54] METHODS OF BIOLOGICAL DOSIMETRY EMPLOYING CHROMOSOME-SPECIFIC STAINING

[75] Inventors: Joe W. Gray, Livermore; Daniel Pinkel, Walnut Creek, both of Calif.

[73] Assignee: The Regents of the University of California, Oakland, Calif.

[*] Notice: This patent is subject to a terminal disclaimer.

[21] Appl. No.: 08/479,526

[22] Filed: Jun. 7, 1995

Related U.S. Application Data

[62] Division of application No. 08/364,400, Dec. 23, 1994, Pat. No. 5,756,696, which is a continuation of application No. 08/242,075, May 13, 1994, abandoned, which is a continuation of application No. 08/120,190, Sep. 13, 1993, abandoned, which is a continuation of application No. 07/862,060, Apr. 2, 1992, abandoned, which is a continuation of application No. 07/444,669, Dec. 1, 1989, abandoned, which is a continuation-in-part of application No. 06/937,793, Dec. 4, 1986, abandoned, which is a continuation-in-part of application No. 06/819,314, Jan. 16, 1986, abandoned.

[51] Int. Cl.[7] .................................................... C12Q 1/68

[52] U.S. Cl. ................................ 435/6; 422/50; 422/68.1

[58] Field of Search .................................. 435/6, 5, 91.2; 536/24.3–24.33; 422/50, 68.1

[56] References Cited

U.S. PATENT DOCUMENTS

| | | | |
|---|---|---|---|
| 4,302,204 | 11/1981 | Wahl et al. | 23/230.3 |
| 4,358,535 | 11/1982 | Falkow et al. | 435/5 |
| 4,582,789 | 4/1986 | Sheldon, III et al. | 435/6 |
| 4,647,529 | 3/1987 | Rodland et al. | 435/6 |
| 4,675,286 | 6/1987 | Calenoff | 435/7 |
| 4,681,840 | 7/1987 | Stephenson et al. | 435/6 |
| 4,683,195 | 7/1987 | Mullis et al. | 435/6 |
| 4,683,202 | 7/1987 | Mullis | 435/91 |
| 4,707,440 | 11/1987 | Stavrianopoulos | 435/6 |

FOREIGN PATENT DOCUMENTS

| | | |
|---|---|---|
| 0 430 402 A2 | 6/1991 | European Pat. Off. . |
| 2019408 | 10/1979 | United Kingdom . |
| 2215724 | 9/1989 | United Kingdom . |
| 8705027 | 8/1987 | WIPO . |
| 9005789 | 5/1990 | WIPO . |

OTHER PUBLICATIONS

Lichter et al., Proceedings of the National Academy of Sciences, (USA) vol. 85, pp 9664–9668, 1988.
Pardue, in Nucleic Acid Hybridization: A Practical Approach, Ed Hames and Higgins, IRL Press, Ch 8, 1985.
Devilee et al. Nucleic Acids Research 14: 2059–2073, 1986.

(List continued on next page.)

*Primary Examiner*—Ardin H. Marschel
*Attorney, Agent, or Firm*—Burns, Doane, Swecker & Mathis, L.L.P.

[57] ABSTRACT

Methods and compositions for staining based upon nucleic acid sequence that employ nucleic acid probes are provided. Said methods produce staining patterns that can be tailored for specific cytogenetic analyses. Said probes are appropriate for in situ hybridization and stain both interphase and metaphase chromosomal material with reliable signals. The nucleic acid probes are typically of a complexity greater than 50 kb, the complexity depending upon the cytogenetic application. Methods are provided to disable the hybridization capacity of shared, high copy repetitive sequences and/or remove such sequences to provide for useful contrast. Still further methods are provided to produce chromosome-specific staining reagents which are made specific to the targeted chromosomal material, which can be one or more whole chromosomes, one or more regions on one or more chromosomes, subsets of chromosomes and/or the entire genome. Probes and test kits are provided for use in tumor cytogenetics, in the detection of disease related loci, in analysis of structural abnormalities, such as translocations, and for biological dosimetry. Further, methods and prenatal test kits are provided to stain targeted chromosomal material of fetal cells, including fetal cells obtained from maternal blood. Still further, the invention provides for automated means to detect and analyse chromosomal abnormalities.

13 Claims, 6 Drawing Sheets

U.S. PATENT DOCUMENTS

| | | |
|---|---|---|
| 4,710,465 | 12/1987 | Weissman et al. ......................... 435/91 |
| 4,711,955 | 12/1987 | Ward et al. ................................ 536/29 |
| 4,721,669 | 1/1988 | Barton ......................................... 435/6 |
| 4,725,536 | 2/1988 | Fritsch et al. ................................ 435/6 |
| 4,755,458 | 7/1988 | Rabbani et al. .............................. 435/5 |
| 4,770,992 | 9/1988 | Van den Engh et al. ................... 435/6 |
| 4,772,691 | 9/1988 | Herman ..................................... 536/27 |
| 4,888,278 | 12/1989 | Singer et al. ................................ 435/6 |
| 5,085,983 | 2/1992 | Scanlon ....................................... 435/6 |
| 5,427,932 | 6/1995 | Weier et al. ............................ 435/91.2 |
| 5,447,841 | 9/1995 | Gray et al. ................................... 435/6 |
| 5,472,842 | 12/1995 | Stokke et al. ................................ 435/6 |
| 5,503,981 | 4/1996 | Mueller et al. ......................... 435/7.21 |

OTHER PUBLICATIONS

Bauman et al., "A New Method for Flourescence Microscopial Localization of Specific DNA Sequences by In Situ Hybridization of Fluorochrome–labelled RNA," *Exp Cell Res*, vol. 128, 1980, pp. 485–490.

Boyle et al, "Differential Distribution of Long and Short Interspersed Element Sequences in the Mouse Genome: Chromosome Karyotyping By Fluorescence In Situ Hybridization," *PNAS (USA)*, vol. 87, Oct. 1990, pp. 7757–7761.

Brock et al., "Quantitative in situ Hybridization Reveals Extent of Sequence Homology Between Related DNA Sequences in *Drosophila melanogaster*", *Chromosoma (Berl.)*, vol. 83, 1981, pp. 159–168.

Bufton et al. "A Highly Polymorphic Locus On Chromosome 16q Revealed By A Probe From A Chromosome–Specific Cosmid Library," *Human Genetics*, vol. 74, 1986, pp. 425–431

Bufton et al, "Four Restriction Fragment Length Polymorphisms Revealed By Probes From A Single Cosmid Map To Human Chromosome 19," *Am J. Hum Genet*, vol. 38, 1986, pp. 447–460.

Burk et al, "Organization and Chromosomal Specificity of Autosomal Homologs of Human Y Chromosome Repeated DNA," *Chromosoma*, vol. 92, 1985, pp. 225–233.

Buroker et al, "Four Restriction Fragment Length Polymorphisms Revealed By Probes From A Single Cosmid Map To Human Chromosome 12q," *Human Genetics*, vol. 72, 1986, pp. 86–94.

Coté et al, "Quantitation of in situ Hybridization of Ribosomal Ribonucleic Acids to Human Diploid Cells," *Chromosoma*, vol. 80, 1980, pp. 349–367.

Cremer et al, "Preparative Dual–Beam Sorting of the Human Y Chromosome and In Situ Hybridization of Cloned DNA Probes," *Cytometry*, vol. 5, 1984, pp. 572–579.

Davies, "The Application of DNA Recombinant Technology to the Analysis of the Human Genome and Genetic Disease," *Human Genetics*, vol. 58, 1981, pp. 351–357.

Dennis et al, "Cytogenetics of the Parthenogenetic Grasshopper *Warramaba virgo* and Its Bisexual Relatives," *Chromosoma*, vol. 82, 1981, pp. 453–469.

Dutrillaux et al, "Characterization of Chromosomal Anomalies in Human Breast Cancer," *Cancer Genet. Cytogenet.*, vol. 49, (1990), pp. 203–217.

Gerhard et al, "Localization Of a Unique Gene By Direct Hybridization in situ," *PNAS*, vol. 78, 1981, pp. 3755–3759.

Haase et al, "Detection of Two Viral Genomes in Single Cells By Double–Label Hybridization in situ and Color Microradioautography," *Science*, vol. 227, 1985, pp. 189–192.

Holden et al, "Amplified Sequences from Chromosome 15, Including Centromeres, Nucleolar Organizer Regions, and Centromeric Heterochromatin, in Homogeneously Staining Regions in the Human Melanoma Cell Line MeWo," *Cancer Genet. & Cytogenet.*, vol. 14, 1985, pp. 131–146.

Houldsworth et al, "Comparative Genomic Hybridization: An Overview," *Am. J. Pathology*, vol. 145, No. 6, 1994, pp. 1253–1260.

Kallioniemi et al, "Comparative Genomic Hybridization for Molecular Cytogenetic Analysis of Solid Tumors," *Science*, vol. 258, 1992, pp. 818–821.

Kallioniemi et al, "Optimizing Comparative Genomic Hybridization for Analysis of DNA Sequence Copy Number Changes in Solid Tumors," *Genes. Chromosomes & Cancer*, vol. 10, 1994, pp. 231–243.

Kallioniemi et al, "ERBB2 Amplification in Breast Cancer Analyzed by Fluorescence in situ Hybridization," *PNAS USA*, vol. 89, 1992, pp. 5321–5325.

Krumlauf et al, "Construction and Characterization of Genomic Libraries From Specific Human Chromosomes," *PNAS*, vol. 79, 1982, pp. 2971–2975.

Kunkel et al, "Organization and Heterogeneity of Sequences Within A Repeating Unit Of Human Y Chromosome Deoxyribonucleic Acid," *Biochem.*, vol. 18, 1979, pp. 3343–3353.

Landegent et al, "Fine Mapping Of The Huntington Disease Linked D4S10 Locus By Non–Radioactive In Situ Hybridization," *Human Genetics*, vol. 73, 1986, pp. 354–357.

Lichter et al, "Fluorescence In Situ Hybridization with Alu and L1 Polymerase Chain Reaction Probes for Rapid Characterization of Human Chromosomes in Hybrid Cell Lines," *PNAS (USA)*, vol. 87, Sep. 1990, pp. 6634–6638.

Litt et al, "A Highly Polymorphic Locus In Human DNA Revealed By Probes From Cosmid 1–5 Maps To Chromosome 2q35–37," *Am J Hum Genet*, vol. 38, 1986, pp. 288–296.

Litt et al, "A Polymorphic Locus On The Long Arm Of Chromosome 20 Defined By Two Probes From A Single Cosmid," *Human Genetics*, vol. 73, 1986, pp. 340–345.

Lux et al, "Hereditary spherocytosis associated with delection of human erythrocyte ankyrin gene on chromosome 8," *Nature*, vol. 345, 1990, pp 736–739.

Malcolm et al, "Chromosomal Localization Of A Single Copy Gene By in situ Hybridization—Human β Globin Genes On The Short Arm Of Chromosome 11," *Am. Human. Genet.*, vol. 45, 1981, pp. 134–141.

Moyzis et al., "Human Chromosome–specific Repetitive DNA Sequences: Novel Markers for Genetic Analysis", *Chromosoma (Berl.)*, vol. 95, 1987, pp. 375–386.

Nelson et al, "Genomic Mismatch Scanning: A New Approach To Genetic Linkage Mapping," Nature Genetics, vol. 4, 1993, pp. 11–18.

Park et al, "Amplification, Overexpression, and Rearrangement of the erbB–2 Protooncogene in Primary Human Stomach Carcinomas," *Cancer Research*, vol. 49, Dec. 1989, pp. 6605–6609.

Pierce et al, " Analysis Of A Dispersed Repetitive DNA Sequence In Isogenic Lines of Drosophila," *Chromosoma*, vol. 82, 1981, pp. 471–492.

Rabin, "Mapping Minimally Reiterated Genes On Diploid Chromosomes By In Situ Hybridization," thesis, Dept. of Biochemistry, Univ. Ill., 1982.

Rabin et al, "Two Homoeo Box Loci Mapped In Evolutionarily Related Mouse And Human Chromosomes," *Nature*, vol. 314, 1985, pp. 175–178.

Ried et al, "Direct carrier detection by in situ suppression hybridization with cosmid clones of the Duchene/Becker muscular dystropy locus," Hum. Genet., vol. 85, 1990, pp. 581–586.

Ried et al, "Simultaneous Visualization of Seven Different DNA Probes by In Situ Hybridization Using Combinatorial Fluorescence and Digital Imaging Microscopy," PNAS (USA), vol. 89, Feb. 1992, pp. 1388–1392.

Ruddle, "A New Era In Mammalian Gene Mapping: Somatic Cell Genetics And Recombinant DNA Methodologies," Nature, vol. 294, 1981, pp. 115–120.

Saint–Ruf et al, "Proto–Oncogene Amplification and Homogeneously Staining Regions in Human Breast Carcinomas," Genes, Chromosomes & Cancer, vol. 2, (1990), pp. 18–26.

Siracusa et al, "Use of Repetitive DNA Sequences To Distinguish *Mus musculus* and *Mus caroli* Cells By in situ Hybridization," J. Embryol. exp. Morph., vol. 73, 1983, pp. 163–178.

Sondermeijer et al, "The Activity of Two Heat Shock Loci of *Drosophila hydei* In Tissue Culture Cells and Salivary Gland Cells as Analyzed by in situ Hybridization of Complementary DNA," Chromosoma, vol. 72, 1979, pp. 281–291.

Steinemann, "Multiple Sex Chromosomes in *Drosophila miranda*: A System to Study the Degeneration of a Chromosome," Chromosoma, vol. 86, 1982, pp. 59–76.

Szabo et al, "Quantitative in Situ Hybridization of Ribosomal RNA Species to Polytene Chromosomes of *Drosophila melanogaster,*" J. Mol. Biol., vol. 115, 1977, pp. 539–563.

Albertson, "Mapping Muscle Protein Genes by in situ Hybridization Using Biotin–Labeled Probes," EMBO J., vol. 4, No. 10, 1985, pp. 2493–2498.

Albertson, "Localization of the Ribosomal Genes in *Caenorhabditis elegans* Chromosomes by in situ Hybridization Using Biotin–Labeled Probes," EMBO J., vol. 3, No. 6, 1984, pp. 1227–1234.

Ardeshir et al, "Structure of Amplified DNA in Different Syrian Hamster Cell Lines Resistant to N–(Phosphonacetyl-)–L–Aspartate," Molecular and Cellular Biology, vol. 3, No. 11, Nov. 1983, pp. 2076–2088.

Arnoldus et al, "Detection of the Philadelphia Chromosome in Interphase Nuclei (With 2 Color Plates)," Cytogenet. Cell Genet., vol. 54, 1990, pp. 108–111.

Bar–Am et al, "Detection of Amplified DNA Sequences in Human Tumor Cell Lines by Fluorescence In Situ Hybridization," Genes, Chromosomes & Cancer, vol. 4, 1992, pp. 314–320.

Benton et al, "Screening λgt Recombinant Clones by Hybridization to Single Plaques in situ," Science, vol. 196, 1977, pp. 180–182.

Bergerheim et al, "Deletion Mapping in Human Renal Cell Carcinoma," Cancer Res., vol. 49, Mar. 1989, pp. 1390–1396.

Bookstein et al, "Human Retinoblastoma Susceptibility Gene: Genomic Organization and Analysis of Heterozygous Intragenic Deletion Mutants," PNAS (USA), vol. 85, Apr. 1988, pp. 2210–2214.

Brison et al, "General Method for Cloning Amplified DNA by Differential Screening with Genomic Probes," Molecular and Cellular Biology, vol. 2, No. 5, May 1982, pp. 578–587.

Britten et al, "Analysis of Repeating DNA Sequences by Reassociation," Methods of Enzymology, vol. 29, 1974, pp. 363–418.

Buongiorno–Nardelli et al, "Autoradiographic Detection of Molecular Hybrids between rRNA and DNA in Tissue Sections," Nature, vol. 225, Mar. 1970, pp. 946–948.

Cannizzaro et al, "In Situ Hybridization and Translocation Breakpoint Mapping II. Two Unusual t(21;22) Translocations," Cytogenet. Cell Genet., vol. 39, 1985, pp. 173–178.

Cantor et al, "The Behavior of Biological Macromolecules, Part III," Biophysical Chemistry, Freeman & Co. 1980, pp. 1183, 1226–1228.

Cohen et al, "Hereditary Renal–Cell Carcinoma Associated with a Chromosomal Translocation," N. Engl. J. Med., vol. 301, No. 11, Sep. 1979, pp. 592–595.

Collins and Weissman, "Directional cloning of DNA fragments at a large distance from an initial probe: A circularization method", PNAS (USA), 81: 6812–6816 (Nov. 1984).

Cox et al, "Detection of mRNAs in Sea Urchin Embryos by in Situ Hybridization Using Asymmetric RNA Probes," Developmental Biology, vol. 101, 1984, pp. 485–502.

Cremer et al, "Detection of Chromosome Aberrations in Metaphase and Interphase Tumor Cells by in situ Hybridization Using Chromosome–Specific Library Probes," Human Genetics, vol. 80, 1988, pp. 235–246.

Cremer et al, "Detection of Chromosome Aberrations in the Human Interphase Nucleus by Visualization of Specific Target DNAs with Radioactive and Non–Radioactive in situ Hybridization Techniques: Diagnosis of Trisomy 18 with Probe L1.84," Hum. Genet., vol. 74, 1986, pp. 346–352.

Cremer et al, "Rapid Interphase and Metaphase Assessment of Specific Chromosomal Changes in Neuroectodermal Tumor Cells by in Situ Hybridization with Chemically Modified DNA Probes," Exp. Cell Res., vol. 176, 1988, pp. 199–220.

Cremer et al, "Rapid Metaphase and Interphase Detection of Radiation–Induced Chromosome Aberrations in Human Lymphocytes by Chromosomal Suppression In Situ Hybridization," Cytometry, vol. 11, 1990, pp. 110–118.

Devilee et al, "Detection of Chromosome Aneuploidy in Interphase Nuclei from Human Primary Breast Tumors Using Chromosome–specific Repetitive DNA Probes," Cancer Res., vol. 48, Oct. 1988, pp. 5825–5830.

Durnam et al, "Detection of Species Specific Chromosomes in Somatic Cell Hybrids," Som. Cell Molec. Genetics, vol. 11, No. 6, 1985, pp. 571–577.

Erikson et al, "Heterogeneity of Chromosome 22 Breakpoint in Philadelphia–positive (Ph$^+$) Acute Lymphocytic Leukemia," PNAS, USA, vol. 83, Mar. 1986, pp. 1807–1811.

Fisher et al, "Adhesive and Degradative Properties of Human Placental Cytotrophoblast Cells In Vitro," J. Cell Biol., vol. 109, No. 2, 1989, pp. 891–902.

Fisher et al, "Molecular Hybridization Under Conditions of High Stringency Permits Cloned DNA Segments Containing Reiterated DNA Sequences to be Assigned to Specific Chromosomal Locations," PNAS, USA, vol. 81, Jan. 1984, pp. 520–524.

Friend et al, "A Human DNA Segment with Properties of the Gene that Predisposes to Retinoblastoma and Osteosarcoma," Nature, vol. 323, Oct. 16, 1986, pp. 643–646.

Fuscoe et al, "An Efficient Method for Selecting Unique–Sequence Clones from DNA Libraries and Its Application To Fluorescent Staining of Human Chromosome 21 Using in Situ Hybridization," Genomics, vol. 5, 1989, pp. 100–109.

Gall et al, "Formation and Detection of RNA–DNA Hybrid Molecules in Cytological Preparations," PNAS (USA), vol. 63, 1969, pp. 378–383.

Gray et al, "Flow Cytometric Detection of Chromosome Aberrations," (Abstract) Conference on Flow Cytometry in Cell Biology and Genetics, Clift Hotel, San Francisco, California, Jan. 15, 1985–Jan. 17, 1985.

Gray et al, "Fluorescence Hybridization to Human Chromosome 21 Using Probes From A Charon 21 A Library," *Cytometry*, (Suppl. 1), 1987, Abst. 19, p. 4.

Grunstein et al, "Colony Hybridization: A Method for the Isolation of Cloned DNAs That Contain A Specific Gene," *PNAS, USA*, vol. 72, No. 10, Oct. 1975, pp. 3961–3965.

Harper et al, "Localization of Single Copy DNA Sequences on G–Banded Human Chromosomes by in situ Hybridization," *Chromosoma (Berl.)*, vol. 83, 1981, pp. 431–439.

Harper et al, "Localization of the Human Insulin Gene to the Distal End of the Short Arm of Chromosome 11," *PNAS (USA)*, vol. 78, No. 7, Jul. 1981, pp. 4458–4460.

Herzenberg et al, "Fetal Cells in the Blood of Pregnant Women: Detection and Enrichment by Fluorescence–Activated Cell Sorting," *PNAS (USA)*, vol. 76, No. 3, Mar. 1979, pp. 1453–1455.

Leroy E. Hood et al, *Molecular Biology of Eucaryotic Cells*, W. A. Benjamin, Inc., Menlo Park, CA, pp. 47–51 (1975).

Jabs et al, "Characterization of a Cloned DNA Sequence that is Present at Centromeres of All Human Autosomes and the X Chromosome and Shows Polymorphic Variation," *PNAS (USA)*, vol. 81, Aug. 1984, pp. 4884–4888.

John et al, "RNA–DNA Hybrids at the Cytological Level," *Nature*, vol. 223, Aug. 1969, pp. 582–587.

Kao et al, "Assignment of the Structural Gene Coding for Albumin to Human Chromosome 4," *Human Genetics*, vol. 62, 1982, pp. 337–341.

Kievits et al, "Direct Nonradioactive In Situ Hybridization of Somatic Cell Hybrid DNA to Human Lymphocyte Chromosomes," *Cytometry*, vol. 11, 1990, pp. 105–109.

Landegent et al, "Use of Whole Cosmid Cloned Genomic Sequences for Chromosomal Localization of Non–Radioactive in situ Hybridization," *Hum. Genet.*, vol. 77, 1987, pp. 366–370.

Landegent et al, "Chromosomal Localization of a Unique Gene by Non–Autoradiographic in situ Hybridization," *Nature*, vol. 317, Sep. 1985, pp. 175–177.

Landegent et al, "2–Acetylaminofluorene–Modified Probes for the Indirect Hybridocytochemical Detection of Specific Nucleic Acid Sequences," *Exp. Cell Res.*, vol. 153, 1984, pp. 61–72.

Landegren et al, "DNA Diagnostics—Molecular Techniques and Automation," *Science*, vol. 242, Oct. 1988, pp. 229–237.

Langer–Safer et al, "Immunological Method for Mapping Genes on Drosophila Polytene Chromosomes," *PNAS (USA)*, vol. 79, 1982, pp. 4381–4385.

Lawrence et al, "Sensitive, High–Resolution Chromatin and Chromosome Mapping In Situ: Presence and Orientation of Two Closely Integrated Copies of EBV in a Lymphoma Line," *Cell*, vol. 52, Jan. 1988, pp. 51–61.

LeGrys et al, "Clinical Applications of DNA Probes in the Diagnosis of Genetic Diseases," *CRC Crit. Rev. Clin. Lab. Sci.*, vol. 25, No. 4, 1987, pp. 255–274.

Lewin, "Genetic Probes Become Ever Sharper—Rapid Detection of Multiple–Pathogen Infections, Including Major Drug–Resistance Genes, May be Possible Using a Newly Developed Technique," *Science*, vol. 221, No. 4616, Sep. 1983, p. 1167.

Lichter et al, "Delineation of Individual Human Chromosomes in Metaphase and Interphase Cells by in situ Suppression Hybridization Using Recombinant DNA Libraries," *Human Genet.*, vol. 80, 1988, pp. 224–234.

Lichter et al, "High–Resolution Mapping of Human Chromosome 11 by in Situ Hybridization with Cosmid Clones," *Science*, vol. 247, Jan. 5, 1990, pp. 64–69.

Lichter et al, "Is Non–Isotopic in situ Hybridization Finally Coming of Age?," *Nature*, vol. 345, May 1990, pp. 93–94.

Litt et al, "A Highly Polymorphic Locus in Human DNA Revealed by Cosmid–Derived Probes," *PNAS, USA*, vol. 82, Sep. 1985, pp. 6206–6210.

LLNL, "Fluorescent Labeling of Human Chromosomes with Recombinant DNA Probes," *Energy & Tech. Review*, Jul. 1985, pp. 84–85.

LLNL, Chromosome–Specific Human Gene Libraries, *Energy & Tech. Review*, Jul. 1985, pp. 82–83.

Lucas et al, "Rapid Translocation Analysis Using Fluorescence In Situ Hybridization: Applied to Long Term Biological Dosimetry", (UCRL 102265 Abstract), Radiation Research Meeting, New Orleans, Louisiana, Apr. 7, 1990–Apr. 12, 1990.

Manuelidis, "Individual Interphase Chromosome Domains Revealed by in situ Hybridization," *Hum. Genet.*, vol. 71, 1985, pp. 288–293.

Manuelidis et al, "Chromosomal and Nuclear Distribution of the HindIII 1.9–kb Human DNA Repeat Segment," *Chromosoma (Berl.)*, vol. 91, 1984, pp. 28–38.

Manuelidis, "Different Central Nervous System Cell Types Display Distinct and Nonrandom Arrangements of Satellite DNA Sequences," *PNAS (USA)*, vol. 81, May 1984, pp. 3123–3127.

McCormick, "The Polymerase Chain Reaction and Cancer Diagnosis," *Cancer Cells*, vol. 1, No. 2, Oct. 1989, pp. 56–61.

Montgomery et al, "Specific DNA Sequence Amplification in Human Neuroblastoma Cells," *PNAS USA*, vol. 80, Sep. 1983, pp. 5724–728.

Nederlof et al, "Detection of Chromosome Aberrations in Interphase Tumor Nuclei by Nonradioactive In Situ Hybridation," *Cancer Genet. Cytogenet.*, vol. 42, 1989, pp. 87–98.

Olsen et al, "Isolation of Unique Sequence Human X Chromosomal Deoxyribonucleic Acid," *Biochemistry*, vol. 19, 1980, pp. 2419–2428.

Pinkel et al, "Detection of Structural Chromosome Aberrations in Metaphase Spreads and Interphase Nuclei by in situ Hybridization High Complexity Probes Which Stain Entire Human Chromosomes," *Am. J. Hum. Genet.* (Supplement) vol. 43, No. 3, Sep. 1988, p. A118 (Abstract 0471: 11.5).

Pinkel et al, "Cytogenetic Analysis Using Quantitative, High–Sensitivity, Fluorescence Hybridization," *PNSA (USA)*, vol. 83, May 1986, pp. 2934–2938.

Pinkel et al, "Cytogenetic Analysis by In Situ Hybridization with Fluorescently Labeled Nucleic Acid Probes," *Cold Spring Harbor Symposia on Quantitative Biology*, vol. L1, 1986, pp. 151–157.

Pinkel et al, "Genetic Analysis by Quantitative Microscopy and Flow Cytometry Using Fluorescence In Situ Hybridization with Chromosome–Specific Nucleic Acid Probes," *Am. J. Hum. Genet.* (Supplement), vol. 39, No. 3, Sep. 1986, p. A129 (379).

Pinkel et al, "Cytogenetic Analysis During Leukemia Therapy Using Fluorescence in situ Hybridization with Chromosome–Specific Nucleic Acid Probes," *Am. J. Hum. Genet.* (Supplement), vol. 41, No. 3, Sep. 1987, p. A34 (096; 12.12).

Pinkel et al, "Simplified Cytogenetics Using Biotin Labeled Nucleic Acid Probes and Quantitative Fluorescence Microscopy," *Am. J. Hum. Genet.* (Supplement), vol. 37, No. 4, Jul. 1985, pp. A112 (328; 17.2).

Pinkel et al, "Fluorescence in situ Hybridization with Human Chromosome–Specific Libraries: Detection of Trisomy 21 and Translocations of Chromosome 4," *PNSA (USA)*, vol. 85, Dec. 1988, pp. 9138–9142.

Pinkel et al, "Cytogenetics Using Fluorescent Nucleic Acid Probes and Quantitative Microscopic Measurement" (UCRL 93269 Abstract), Analytical Cytology X Conference, Hilton Head Resort, Hilton Head Island, S.C., Nov. 17, 1985–Nov. 22, 1985.

Pinkel et al, "Rapid Quantitative Cytogenic Analysis Using Fluorescently Labeled Nucleic Acid Probes", (UCRL 93553 Abstract), U.S.—Japan Joint Environmental Panel Conf., Research Triangle Park, N.C., Oct. 21, 1985–Oct. 23, 1985.

Pinkel et al, "Detection of Structural and Numerical Abnormalities in Metaphase Spreads and Interphase Nuclei Using In Situ Hybridization", *Cancer Genet. and Cytogenet.* (UCRL 101043 Abstract) 41:236 (Oct. 1989).

Lewin, *Genes*, (2nd Ed., John Wiley & Sons, Inc. 1984) pp. 298–299 and pp. 464–465.

Pinkel et al, "Detection of Translocations and Aneuploidy in Metaphase Spreads and Interphase Nuclei by In Situ Hybridization with Probes Which Stain Entire Human Chromosomes," (UCRL 101042 Abstract) 21st Oak Ridge Conference on Advanced Conepts in the Clinical Laboratory, Apr. 13, 1989–Apr. 14, 1989.

Rappold et al, "Sex Chromosome Positions in Human Interphase Nuclei as Studied by in situ Hybridization with Chromosome Specific DNA Probes," *Human Genetics*, vol. 67, 1984, pp. 317–322.

Roelofs et al, "Gene Amplification in Human Cells May Involve Interchromosomal Transposition and Persistence of the Original DNA Region," *The New Biologist*, vol. 4, No. 1, (Jan. 1992), pp. 75–86.

Scalenghe et al, "Microdissection and Cloning of DNA from a Specific Region of *Drosophila melanogaster* Polytene Chromosomes," *Chromosoma (Berl.)*, vol. 82, 1981, pp. 205–216.

Schardin et al, "Specific Staining of Human Chromosomes in Chinese Hamster X Man Hybrid Cell Lines Demonstrates Interphase Chromosome Territories," *Hum. Genet.*, vol. 71, 1985, pp. 281–287.

Schmeckpeper et al, "Partial Purification and Characterization of DNA from the Human X Chromosome," *PNAS (USA)*, vol. 76, No. 12, Dec. 1979, pp. 6525–6528.

Sealy, et al, "Removal of Repeated Sequences from Hybridisation Probes," *Nucleic Acid Research*, vol. 13, No. 6, 1985, pp. 1905–1922.

Selypes et al, "A Noninvasive Method for Determination of the Sex and Karyotype of the Fetus from the Maternal Blood," *Hum. Genet.*, vol. 79, 1988, pp. 357–359.

Smith et al, "Distinctive Chromosomal Structures Are Formed Early in the Amplification of CAD Genes in Syrian Hamster Cells," *Cell*, vol. 63, (Dec. 21, 1990), pp. 1219–1227.

Sparkes et al, "Regional Assignment of Genes for Human Esterase D and Retinoblastoma to Chromosome Band 13q14," *Science*, vol. 208, May 30, 1988, pp. 1042–1044.

Stewart et al, "Cloned DNA Probes Regionally Mapped to Human Chromosome 21 and Their Use in Determining the Origin of Nondisjunction," *Nucleic Acids Research*, vol. 13, No. 11, 1985, pp. 4125–4132.

Straume et al, "Chromosome Translocation of Low Radiation Doses Quantified Using Fluorescent DNA Probes", (UCRL 93837 Abstract), Radiation Research Society Meeting, Las Vegas, Nevada, Apr. 12, 1986–Apr. 17, 1986.

Szabo et al, "What's New With Hybridization in situ?" *TIBS*, vol. 7, No. 11, Dec. 1982, pp. 425–427.

Thompson et al, *Thompson & Thompson: Genetics in Medicine*, 5th ed., W.B. Saunders Co., Philadelphia, PA, pp. 38–39 (1991).

Trask et al, "The Proximity of DNA Sequences in Interphase Cell Nuclei Is Correlated to Genomic Distance and Permits Ordering of Cosmids Spanning 250 Kilobase Pairs," *Genomics*, vol. 5, 1989, pp. 710–717.

Trask et al, "Detection of DNA Sequences in Nuclei in Suspension by In Situ Hybridization and Dual Beam Flow Cytometry" (UCRL 93372 Abstract)—Analytical Cytology X Conference, Hilton Head Resort, Hilton Head Island, S.C., Nov. 17, 1985–Nov. 22, 1985.

Trask et al, "Early Dihydrofolate Reductase Gene Amplification Events in CHO Cells Usually Occur on the Same Chromosome Arm as the Original Locus," *Genes & Development*, vol. 3, (1989), pp. 1913–1925.

Trent et al, "Report of the Committee on Structural Chromosome Changes in Neoplasia," *Cytogenet. Cell Genet.*, vol. 51, 1989, pp. 533–562.

Van Dilla et al, "Construction and Availability of Human Chromosome–Specific DNA Libraries From Flow Sorted Chromosomes: Status Report," *Am. J. of Human Genetics*, vol. 37 (R Supplement) Jul. 1985, p. A179.

Wallace et al, "The Use of Synthetic Oligonucleotides as Hybridization Probes—II Hybridization of Oligonucleotides of Mixed Sequence to Rabbit β Globin DNA," *Nucleic Acids Research*, vol. 9, No. 4, 1981, pp. 879–894.

Weiss et al, "Organization and Evolution of the Class I Gene Family in the Major Histocompatibility Complex of the C57BL/10 Mouse," *Nature*, vol. 310, No. 23, Aug. 1984, pp. 650–655.

Willard et al, "Isolation and Characterization of a Major Tandem Repeat Family from the Human X Chromosome," *Nucleic Acids Research*, vol. 11, No. 7, 1983, pp. 2017–2033.

Windle et al, "A Central Role for Chromosome Breakage in Gene Amplification, Deletion Formation, and Amplicon Integration," *Genes & Development*, vol. 5, (1991), pp. 160–174.

Yunis et al, "Localization of Sequences Specifying Messenger RNA to Light–Staining G–Bands of Human Chromosomes," *Chromosoma (Berl.)*, vol. 61, 1977, pp. 335–344.

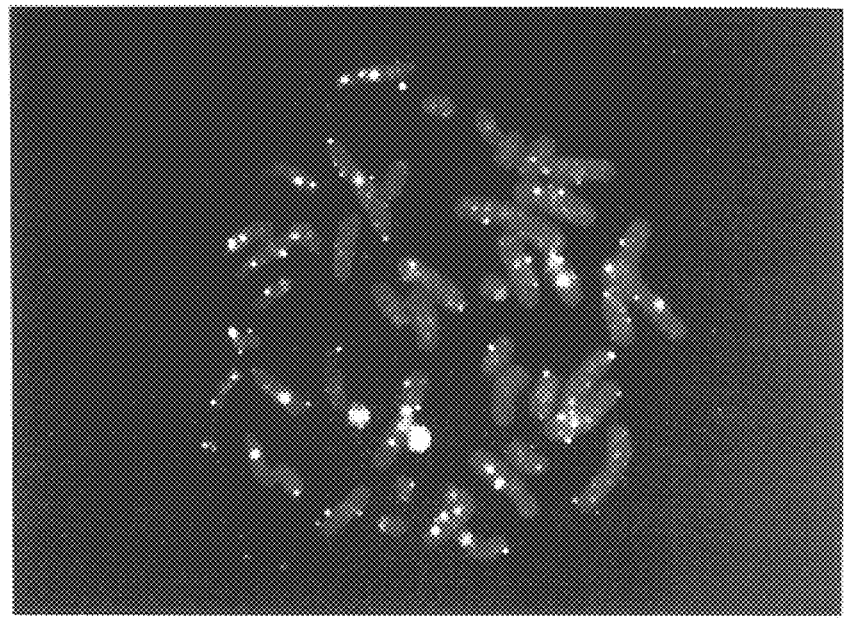
FIG. 3
 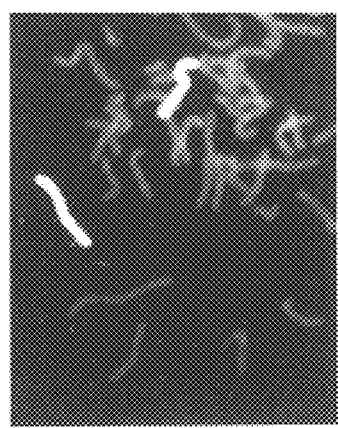 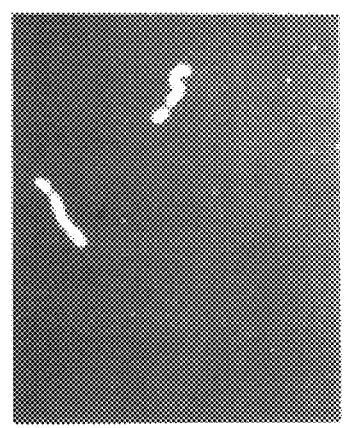
FIG. 4A          FIG. 4B          FIG. 4C

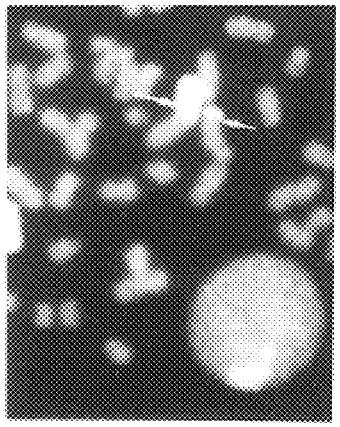 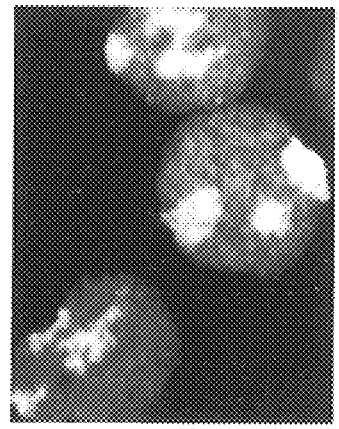 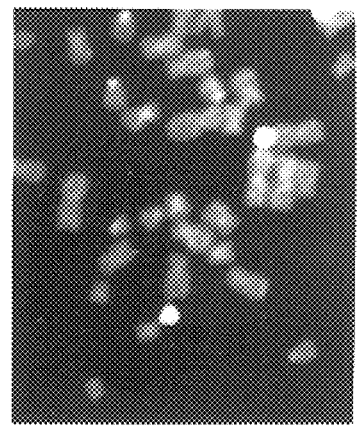
FIG. 4D  FIG. 4E  FIG. 4F
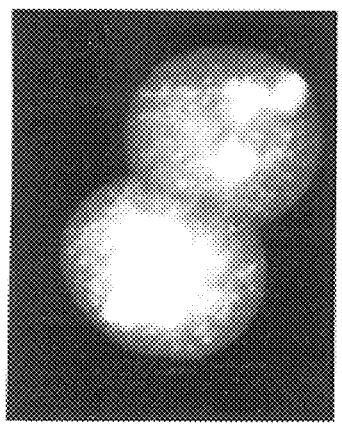 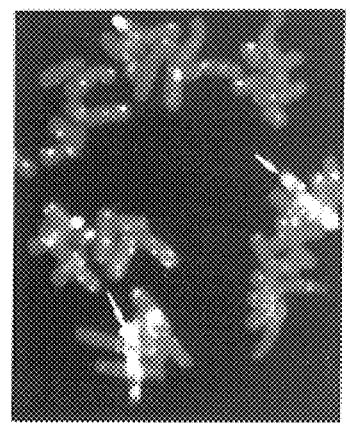
FIG. 4G  FIG. 4H

METHODS OF BIOLOGICAL DOSIMETRY EMPLOYING CHROMOSOME-SPECIFIC STAINING

RELATED APPLICATION

This application is a divisional application Ser. No. 08/364,400, filed Dec. 23, 1994, now U.S. Pat. No. 5,756,696; which is a continuation of application Ser. No. 08/242,075, filed May 13, 1994, now abandoned, which is a continuation of application Ser. No. 08/120,190, filed Sep. 13, 1993, now abandoned, which is a continuation of application Ser. No. 07/862,060, filed Apr. 2, 1992, now abandoned, which is a continuation of application Ser. No. 07/444,669, filed Dec. 1, 1989, now abandoned, which is a continuation-in-part of application Ser. No. 06/937,793, filed Dec. 4, 1986, now abandoned, which is a continuation-in-part of application Ser. No. 06/819,314, filed Jan. 16, 1986, now abandoned.

The United States Government has rights in this invention pursuant to Contract No. W-7405-ENG-48 between the U.S. Department of Energy and the University of California, for the operation of Lawrence Livermore National Laboratory.

FIELD OF THE INVENTION

The invention relates generally to the field of cytogenetics, and more particularly, to the field of molecular cytogenetics. The invention concerns methods for identifying and classifying chromosomes. Still more particularly, this invention concerns nucleic acid probes which can be designed by the processes described herein to produce staining distributions that can extend along one or more whole chromosomes, and/or along a region or regions on one or more chromosomes, including staining patterns that extend over the whole genome. Staining patterns can be tailored for any desired cytogenetic application, including prenatal, tumor and disease related cytogenetic applications, among others. The invention provides for compositions of nucleic acid probes and for methods of staining chromosomes therewith to identify normal chromosomes and chromosomal abnormalities in metaphase spreads and in interphase nuclei. The probe-produced staining patterns of this invention facilitate the microscopic and/or flow cytometric identification of normal and abnormal chromosomes and the characterization of the genetic nature of particular abnormalities.

Although most of the examples herein concern human chromosomes and much of the language herein is directed to human concerns, the concept of using nucleic acid probes for staining or painting chromosomes is applicable to chromosomes from any source including both plants and animals.

BACKGROUND OF THE INVENTION

Chromosome abnormalities are associated with genetic disorders, degenerative diseases, and exposure to agents known to cause degenerative diseases, particularly cancer, German, "Studying Human Chromosomes Today, " *American Scientist,* Vol. 58, pgs. 182–201 (1970); Yunis, "The Chromosomal Basis of Human Neoplasia," *Science,* Vol. 221, pgs. 227–236 (1983); and German, "Clinical Implication of Chromosome Breakage," in *Genetic Damage in Man Caused by Environmental Agents,* Berg, Ed., pgs. 65–86 (Academic Press, New York, 1979). Chromosomal abnormalities can be of several types, including: extra or missing individual chromosomes, extra or missing portions of a chromosome (segmental duplications or deletions), breaks, rings and chromosomal rearrangements, among others. Chromosomal rearrangements include translocations (transfer of a piece from one chromosome onto another chromosome), dicentrics (chromosomes with two centromeres), and inversions (reversal in polarity of a chromosomal segment).

Detectable chromosomal abnormalities occur with a frequency of one in every 250 human births. Abnormalities that involve deletions or additions of chromosomal material alter the gene balance of an organism and generally lead to fetal death or to serious mental and physical defects. Down syndrome can be caused by having three copies of chromosome 21 instead of the normal 2. This syndrome is an example of a condition caused by abnormal chromosome number, or aneuploidy. Down syndrome can also be caused by a segmental duplication of a subregion on chromosome 21 (such as, 21q22), which can be present on chromosome 21 or on another chromosome. Edward syndrome (18+), Patau syndrome (13+), Turner syndrome (XO) and Kleinfelter syndrome (XXY) are among the most common numerical aberrations. [Epstein, *The Consequences of Chromosome Imbalance: Principles, Mechanisms and Models* (Cambridge Univ. Press 1986); Jacobs, *Am. J. Epidemiol,* 105:180 (1977); and Lubs et al., *Science,* 169:495 (1970).]

Retinoblastoma (del 13q14), Prader-Willi syndrome (del 15q11->q13), Wilm's tumor (del 11p13) and Cri-du-chat syndrome (del 5p) are examples of important disease linked structural aberrations. [Nora and Fraser, *Medical Genetics: Principles and Practice,* (Lea and Febiger 1989).]

Chronic myelogeneous leukemia is associated with the exchange of chromosomal material between chromosome 9 and chromosome 22. The transfer of chromosomal material in this leukemia is an example of a translocation. Clearly, a sensitive method for detecting chromosomal abnormalities would be a highly useful tool for genetic screening.

Measures of the frequency of structurally aberrant chromosomes, for example, dicentric chromosomes, caused by clastogenic agents, such as, ionizing radiation or chemical mutagens, are widely used as quantitative indicators of genetic damage caused by such agents, *Biochemical Indicators of Radiation Injury in Man* (International Atomic Energy Agency, Vienna, 1971); and Berg, Ed. *Genetic Damage in Man Caused by Environmental Agents* (Academic Press, New York, 1979). A host of potentially carcinogenic and teratogenic chemicals are widely distributed in the environment because of industrial and agricultural activity. These chemicals include pesticides, and a range of industrial wastes and by-products, such as halogenated hydrocarbons, vinyl chloride, benzene, arsenic, and the like, Kraybill et al., Eds., *Environmental Cancer* (Hemisphere Publishing Corporation, New York, 1977). Sensitive measures of chromosomal breaks and other abnormalities could form the basis of improved dosimetric and risk assessment methodologies for evaluating the consequences of exposure to such occupational and environmental agents.

Current procedures for genetic screening and biological dosimetry involve the analysis of karyotypes. A karyotype is the particular chromosome complement of an individual or of a related group of individuals, as defined both by the number and morphology of the chromosomes usually in mitotic metaphase. It includes such things as total chromosome number, copy number of individual chromosome types (e.g., the number of copies of chromosome X), and chromosomal morphology, e.g., as measured by length, centromeric index, connectedness, or the like. Chromosomal abnormalities can be detected by examination of karyotypes. Karyotypes are conventionally determined by staining an organism's metaphase, or otherwise condensed (for example, by premature chromosome condensation) chromosomes. Condensed chromosomes are used because, until recently, it has not been possible to visualize interphase chromosomes due to their dispersed condition and the lack of visible boundaries between them in the cell nucleus.

A number of cytological techniques based upon chemical stains have been developed which produce longitudinal patterns on condensed chromosomes generally referred to as bands. The banding pattern of each chromosome within an organism usually permits unambiguous identification of each chromosome type, Latt, "Optical Studies of Metaphase Chromosome Organization," *Annual Review of Biophysics and Bioengineering*, Vol. 5, pgs. 1–37 (1976). Accurate detection of some important chromosomal abnormalities, such as translocations and inversions, has required such banding analysis.

Unfortunately, such conventional banding analysis requires cell culturing and preparation of high quality metaphase spreads, which is time consuming and labor intensive, and frequently difficult or impossible. For example, cells from many tumor types are difficult to culture, and it is not clear that the cultured cells are representative of the original tumor cell population. Fetal cells capable of being cultured need to be obtained by invasive means and need to be cultured for several weeks to obtain enough metaphase cells for analysis. In many cases, the banding patterns on the abnormal chromosomes do not permit unambiguous identification of the portions of the normal chromosomes that make them up. Such identification may be important to indicate the location of important genes involved in the abnormality. Further, the sensitivity and resolving power of current methods of karyotyping are limited by the fact that multiple chromosomes or chromosomal regions have highly similar staining characteristics, and that abnormalities (such as deletions) which involve only a fraction of a band are not detectable. Therefore, such methods are substantially limited for the diagnosis and detailed analysis of contiguous gene syndromes, such as partial trisomy, Prader-Willi syndrome [Emanuel, *Am. J. Hum. Genet.*, 43:575 (1988); Schmickel, *J. Pediatr.*, 109:231 (1986)] and retinoblastoma [Sparkes, *Biochem. Biophys. Acta.*, 780:95 (1985)].

Thus, conventional banding analysis has several important limitations, which include the following. 1) It is labor intensive, time consuming, and requires a highly trained analyst. 2) It can be applied only to condensed chromosomes. 3) It does not allow for the detection of structural aberrations involving less than 3–15 megabases (Mb), depending upon the nature of the aberration and the resolution of the banding technique [Landegren et al., *Science*, 242:229 (1988)]. This invention provides for probe compositions and methods to overcome such limitations of conventional banding analysis.

The chemical staining procedures of the prior art provide patterns over a genome for reasons not well understood and which cannot be modified as required for use in different applications. Such chemical staining patterns were used to map the binding site of probes. However, only occasionally, and with great effort, was in situ hybridization used to obtain some information about the position of a lesion, for example, a breakpoint relative to a particular DNA sequence. The present invention overcomes the inflexibility of chemical staining in that it stains a genome in a pattern based upon nucleic acid sequence; therefore the pattern can be altered as required by changing the nucleic acid sequence of the probe. The probe-produced staining patterns of this invention provide reliable fundamental landmarks which are useful in cytogenetic analysis.

Automated detection of structural abnormalities of chromosomes with image analysis of chemically stained bands would require the development of a system that can detect and interpret the banding patterns produced on metaphase chromosomes by conventional techniques. It has proven to be very difficult to identify reliably by automated means normal chromosomes that have been chemically stained; it is much more difficult to differentiate abnormal chromosomes having structural abnormalities, such as, translocations. Effective automated detection of translocations in conventionally banded chromosomes has not been accomplished after over a decade of intensive work. The probe-produced banding patterns of this invention are suitable for such automated detection and analysis.

In recent years rapid advances have taken place in the study of chromosome structure and its relation to genetic content and DNA composition. In part, the progress has come in the form of improved methods of gene mapping based on the availability of large quantities of pure DNA and RNA fragments for probes produced by genetic engineering techniques, e.g., Kao, "Somatic Cell Genetics and Gene Mapping," *International Review of Cytology*, Vol. 85, pgs. 109–146 (1983), and D'Eustachio et al., "Somatic Cell Genetics in Gene Families," *Science*, Vol. 220, pgs. 9, 19–924 (1983). The probes for gene mapping comprise labeled fragments of single-stranded or double-stranded DNA or RNA which are hybridized to complementary sites on chromosomal DNA. With such probes it has been crucially important to produce pure, or homogeneous, probes to minimize hybridizations at locations other than at the site of interest, Henderson, "Cytological Hybridization to Mammalian Chromosomes," *International Review of Cytology*, Vol. 76, pgs. 1–46 (1982).

The hybridization process involves unravelling, or melting, the double-stranded nucleic acids of the probe and target by heating, or other means (unless the probe and target are single-stranded nucleic acids). This step is sometimes referred to as denaturing the nucleic acid. When the mixture of probe and target nucleic acids cool, strands having complementary bases recombine, or anneal. When a probe anneals with a target nucleic acid, the probe's location on the target can be detected by a label carried by the probe or by some intrinsic characteristics of the probe or probe-target duplex. When the target nucleic acid remains in its natural biological setting, e.g., DNA in chromosomes, mRNA in cytoplasm, portions of chromsomes or cell nuclei (albeit fixed or altered by preparative techniques), the hybridization process is referred to as in situ hybridization.

In situ hybridization probes were initially limited to identifying the location of genes or other well defined nucleic acid sequences on chromosomes or in cells. Comparisons of the mapping of single-copy probes to normal and abnormal chromosomes were used to examine chromosomal abnormalities. Cannizzaro et al., *Cytogenetics and Cell Genetics*, 39:173–178 (1985). Distribution of the multiple binding sites of repetitive probes could also be determined.

Hybridization with probes which have one target site in a haploid genome, single-copy or unique sequence probes, has been used to map the locations of particular genes in the genome [Harper and Saunders, "Localization of the Human Insulin Gene to the Distal End of the Short Arm of Chromosome 11," *Proc. Natl. Acad. Sci.,* Vol. 78, pgs. 4458–4460 (1981); Kao et al., "Assignment of the Structural Gene Coding for Albumin to Chromosome 4," *Human Genetics,* Vol. 62, pgs. 337–341 (1982)]; but such hybridizations are not reliable when the size of the target site is small. As the amount of target sequence for low complexity single-copy probes is small, only a portion of the potential target sites in a population of cells form hybrids with the probe. Therefore, mapping the location of the specific binding site of the probe has been complicated by background signals produced by non-specific binding of the probe and also by noise in the detection system (for example, autoradiography or immunochemistry). The unreliability of signals for such prior art single-copy probes has required statistical analysis of the positions of apparent hybridization signals in multiple cells to map the specific binding site of the probe.

Wallace et al., in "The Use of Synthetic Oligonucleotides as Hybridization Probes. II. Hybridization of Oligonucleotides of Mixed Sequence to Rabbit Beta-Globin DNA," *Nucleic Acids Research,* Vol. 9, pgs. 879–894 (1981), disclose the construction of synthetic oligonucleotide probes having mixed base sequences for detecting a single locus corresponding to a structural gene. The mixture of base sequences was determined by considering all possible nucleotide sequences which could code for a selected sequence of amino acids in the protein to which the structural gene corresponded.

Olsen et al., in "Isolation of Unique Sequence Human X Chromosomal Deoxyribonucleic Acid," *Biochemistry,* Vol. 19, pgs. 2419–2428 (1980), disclose a method for isolating labeled unique sequence human X chromosomal DNA by successive hybridizations: first, total genomic human DNA against itself so that a unique sequence DNA fraction can be isolated; second, the isolated unique sequence human DNA fraction against mouse DNA so that homologous mouse/human sequences are removed; and finally, the unique sequence human DNA not homologous to mouse against the total genomic DNA of a human/mouse hybrid whose only human chromosome is chromosome X, so that a fraction of unique sequence X chromosomal DNA is isolated. Individual clones are then isolated from this fraction and are candidates for human X chromosome specific DNA sequences.

Manuelidis et al., in "Chromosomal and Nuclear Distribution of the Hind III 1.9-KB Human DNA Repeat Segment," *Chromosoma,* Vol. 91, pgs. 28–38 (1984), disclose the construction of a single kind of DNA probe for detecting multiple loci on chromosomes corresponding to the location of members of a family of repeated DNA sequences. Such probes are herein termed repetitive probes.

Different repetitive sequences may have different distributions on chromosomes. They may be spread over all chromosomes as in the just cited reference, or they may be concentrated in compact regions of the genome, such as, on the centromeres of the chromosomes, or they may have other distributions. In some cases, such a repetitive sequence is predominantly located on a single chromosome, and therefore is a chromosome-specific repetitive sequence. [Willard et al., "Isolation and Characterization of a Major Tandem Repeat Family from the Human X Chromosome," *Nucleic Acids Research,* Vol. 11, pgs. 2017–2033 (1983).]

A probe for repetitive sequences shared by all chromosomes can be used to discriminate between chromosomes of different species if the sequence is specific to one of the species. Total genomic DNA from one species which is rich in such repetitive sequences can be used in this manner. [Pinkel et al. (III), *PNAS USA,* 83:2934 (1986); Manuelidis, *Hum. Genet.,* 71: 288 (1985) and Durnam et al., *Somatic Cell Molec. Genet.,* 11: 571 (1985).]

Recently, there has been an increased availability of probes for repeated sequences (repetitive probes) that hybridize intensely and specifically to selected chromosomes. [Trask et al., *Hum. Genet.,* 78: 251 (1988) and references cited therein.] Such probes are now available for over half of the human chromosomes. In general, they bind to repeated sequences on compact regions of the target chromosome near the centromere. However, one probe has been reported that hybridizes to human chromosome 1p36, and there are several probes that hybridize to human chromosome Yq. Hybridization with such probes permits rapid identification of chromosomes in metaphase spreads, determination of the number of copies of selected chromosomes in interphase nuclei [Pinkel et al. (I), *PNAS USA.* 83: 2934 (1986); Pinkel et al. (II), *Cold Spring Harbor Symp. Quant. Biol.,* 51: 151 (1986) and Cremer et al., *Hum. Genet,* 74: 346 (1986)] and determination of the relative positions of chromosomes in interphase nuclei [Trask et al., supra; Pinkel et al. (I), supra; Pinkel et al. (II), supra; Manuelidis, *PNAS USA,* 81: 3123 (1984); Rappold et al., *Hum. Genet.,* 67:317 (1984); Schardin et al., *Hum. Genet.,* 71: 282 (1985); and Manuelidis, *Hum. Genet.,* 71: 288 (1985)].

However, many applications are still limited by the lack of appropriate probes. For example, until the methods described herein were invented, probes with sufficient specificity for prenatal diagnosis were not available for chromosome 13 or 21. Further, repetitive probes are not very useful for detection of structural aberrations since the probability is low that the aberrations will involve the region to which the probe hybridizes.

This invention overcomes the prior art limitations on the use of probes and dramatically enhances the application of in situ hybridization for cytogenetic analysis. As indicated above, prior art probes have not been useful for in-depth cytogenetic analysis. Low complexity single-copy probes do not at this stage of hybridization technology generate reliable signals. Although repetitive probes do provide reliable signals, such signals cannot be tailored for different applications because of the fixed distribution of repetitive sequences in a genome. The probes of this invention combine the hybridization reliability of repetitive probes with the flexibility of being able to tailor the binding pattern of the probe to any desired application.

The enhanced capabilities of the probes of this invention come from their increased complexity. Increasing the complexity of a probe increases the probability, and therefore the intensity, of hybridization to the target region, but also increases the probability of non-specific hybridizations resulting in background signals. However, within the concept of this invention, it was considered that such background signals would be distributed approximately randomly over the genome. Therefore, the net result is that the target region could be visualized with increased contrast against such background signals.

Exemplified herein are probes in an approximate complexity range of from about 50,000 bases (50 kb) to hundreds of millions of bases. Such representative probes are for compact loci and whole human chromosomes. Prior to this invention, probes employed for in situ hybridization techniques had complexities below 40 kb, and more typically on the order of a few kb.

Staining chromosomal material with the probes of this invention is significantly different from the chemical staining of the prior art. The specificity of the probe produced staining of this invention arises from an entirely new source—the nucleic acid sequences in a genome. Thus, staining patterns of this invention can be designed to highlight fundamental genetic information important to particular applications.

The procedures of this invention to construct probes of any desired specificity provide significant advances in a broad spectrum of cytogenetic studies. The analysis can be carried out on metaphase chromosomes and interphase nuclei. The techniques of this invention can be especially advantageous for applications where high-quality banding by conventional methods is difficult or suspected of yielding biased information, e.g., in tumor cytogenetics. Reagents targeted to sites of lesions known to be diagnostically or prognostically important, such as tumor type-specific translocations and deletions, permit rapid recognition of such abnormalities. Where speed of analysis is the predominant concern, e.g., detection of low-frequency chromosomal aberrations induced by toxic environmental agents, the compositions of this invention permit a dramatic increase in detection efficiency in comparison to previous techniques based on conventional chromosome banding.

Further, prenatal screening for disease-linked chromosome aberrations (e.g., trisomy 21) is enhanced by the rapid detection of such aberrations by the methods and compositions of this invention. Interphase aneuploidy analysis according to this invention is particularly significant for prenatal diagnosis in that it yields more rapid results than are available by cell culture methods. Further, fetal cells separated from maternal blood, which cannot be cultured by routine procedures and therefore cannot be analysed by conventional karyotyping techniques, can be examined by the methods and compositions of this invention. In addition, the intensity, contrast and color combinations of the staining patterns, coupled with the ability to tailor the patterns for particular applications, enhance the opportunities for automated cytogenetic analysis, for example, by flow cytometry or computerized microscopy and image analysis.

SUMMARY OF THE INVENTION

This invention concerns methods of staining chromosomal material based upon nucleic acid sequence that employ one or more nucleic acid probes. Said methods produce staining patterns that can be tailored for specific cytogenetic analyses. It is further an object of this invention to produce nucleic acid probes that are useful for cytogenetic analysis, that stain chromosomal material with reliable signals. Such probes are appropriate for in situ hybridization. Preferred nucleic acid probes for certain applications of this invention are those of sufficient complexity to stain reliably each of two or more target sites.

The invention provides methods and compositions for staining chromosomal material. The probe compositions of this invention at the current state of hybridization techniques are typically of high complexity, usually greater than about 50 kb of complexity, the complexity depending upon the application for which the probe is designed. In particular, chromosome specific staining reagents are provided which comprise heterogeneous mixtures of nucleic acid fragments, each fragment having a substantial fraction of its sequences substantially complementary to a portion of the nucleic acid for which specific staining is desired—the target nucleic acid, preferably the target chromosomal material. In general, the nucleic acid fragments are labeled by means as exemplified herein and indicated infra. However, the nucleic acid fragments need not be directly labeled in order for the binding of probe fragments to the target to be detected; for example, such nucleic acid binding can be detected by anti-RNA/DNA duplex antibodies and antibodies to thymidine dimers. The nucleic acid fragments of the heterogenous mixtures include double-stranded or single-stranded RNA or DNA.

One way to produce a probe of high complexity is to pool several or many clones, for example, phage, plasmid, cosmid, and/or YAC clones, among others, wherein each clone contains an insert that is capable or hybridizing to some part of the target in a genome. Another way to produce such a probe is to use the polymerase chain reaction (PCR).

Heterogeneous in reference to the mixture of labeled nucleic acid fragments means that the staining reagents comprise many copies each of fragments having different sequences and/or sizes (e.g., from the different DNA clones pooled to make the probe). In preparation for use, these fragments may be cut, randomly or specifically, to adjust the size distribution of the pieces of nucleic acid participating in the hybridization reaction.

As discussed more fully below, preferably the heterogeneous probe mixtures are substantially free from nucleic acid sequences with hybridization capacity to non-target nucleic acid. Most of such sequences bind to repetitive sequences which are shared by the target and non-target nucleic acids, that is, shared repetitive sequences.

Methods to remove undesirable nucleic acid sequences and/or to disable the hybridization capacity of such sequences are discussed more fully below. [See Section II]. Such methods include but are not limited to the selective removal or screening of shared repetitive sequences from the probe; careful selection of nucleic acid sequences for inclusion in the probe; blocking shared repetitive sequences by the addition of unlabeled genomic DNA, or, more carefully selecting nucleic acid sequences for inclusion in the blocking mixture; incubating the probe mixture for sufficient time for reassociation of high copy repetitive sequences, or the like.

Preferably, the staining reagents of the invention are applied to interphase or metaphase chromosomal DNA by in situ hybridization, and the chromosomes are identified or classified, i.e., karyotyped, by detecting the presence of the label, such as biotin or $^3$H, on the nucleic acid fragments comprising the staining reagent.

The invention includes chromosome staining reagents for the total genomic complement of chromosomes, staining reagents specific to single chromosomes, staining reagents specific to subsets of chromosomes, and staining reagents specific to subregions within single or multiple chromosomes. The term "chromosome-specific," is understood to encompass all of these embodiments of the staining reagents of the invention. The term is also understood to encompass staining reagents made from and directed against both normal and abnormal chromosome types.

A preferred method of making the chromosome-specific staining reagents of the invention includes: 1) isolating chromosomal DNA from a particular chromosome type or target region or regions in the genome, 2) amplifying the isolated DNA to form a heterogeneous mixture of nucleic acid fragments, 3) disabling the hybridization capacity of or removing shared repeated sequences in the nucleic acid fragments, and 4) labeling the nucleic acid fragments to form a heterogeneous mixture of labeled nucleic acid fragments. As described more fully below, the ordering of the steps for particular embodiments varies according to the particular means adopted for carrying out the steps.

The present invention addresses problems associated with karyotyping chromosomes, especially for diagnostic and dosimetric applications. In particular, the invention overcomes problems which arise because of the lack of stains that are sufficiently chromosome-specific by providing reagents comprising heterogeneous mixtures of nucleic acid fragments that can be hybridized to the target DNA and/or RNA, e.g., the target chromosomes, target subsets of chromosomes, or target regions of specific chromosomes. The staining technique of the invention opens up the possibility of rapid and highly sensitive detection of chromosomal abnormalities in both metaphase and interphase cells using standard clinical and laboratory equipment and improved analysis using automated techniques. It has direct application in genetic screening, cancer diagnosis, and biological dosimetry.

This invention further specifically provides for methods and nucleic acid probes for staining fetal chromosomal material, whether condensed, as in metaphase, or dispersed as in interphase. Still further, the invention provides for a non-embryo-invasive method of karyotyping the chromosomal material of fetal cells, wherein the fetal cells have been separated from maternal blood. Such fetal cells are preferably leukocytes and/or cytotrophoblasts. Exemplary nucleic acid probes are high complexity probes chromosome-specific for chromosome types 13, 18 and/or 21. Representative probes comprise chromosome-specific Bluescribe plasmid libraries from which a sufficient number of shared repetitive sequences have been removed or the hybridization capacity thereof has been disabled prior to and/or during hybridization with the target fetal chromosomes.

This invention still further provides for test kits comprising appropriate nucleic acid probes for use in tumor cytogenetics, in the detection of disease related loci, in the analysis of structural abnormalities, for example translocations, and for biological dosimetry.

This invention further provides for prenatal screening kits comprising appropriate nucleic acid probes of this invention.

The methods and compositions of this invention permit staining of chromosomal material with patterns appropriate for a desired application. The pattern may extend over some regions of one or more chromosomes, or over some or all the chromosomes of a genome and may comprise multiple distinguishable sections, distinguishable, for example, by multiple colors. Alternatively, the pattern may be focused on a particular portion or portions of a genome, such as a portion or portions potentially containing a deletion or breakpoint that is diagnostically or prognostically important for one or more tumors, or on those portions of chromosomes having significance for prenatal diagnosis.

The staining patterns may be adjusted for the analysis method employed, for example, either a human observer or automated equipment, such as, flow cytometers or computer assisted microscopy. The patterns may be chosen to be appropriate for analysis of condensed chromosomes or dispersed chromosomal material.

The invention further provides for automated means of detecting and analyzing chromosomal abnormalities as indicated by the staining patterns produced according to this invention.

BRIEF DESCRIPTION OF THE DRAWINGS

FIG. 1A is a binary image of the DAPI stain in the human metaphase spread obtained by using a TV camera attached to a fluorescence microscope. Filters appropriate for DAPI visualization were used. Computer processing of the image shows all portions above a chosen threshold intensity as white, and the rest as black.

FIG. 2A is a color photograph of the DAPI stain in a human metaphase spread which was prepared and hybridized contemporaneously with the spread shown in the computer generated binary images of FIGS. 1A, B and C.

FIG. 2B is a color photograph of the fluorescein attached to the DNA probe in the same human metaphase spread as shown in FIG. 2A. It was obtained by changing the filters in the fluorescence microscope to excite fluorescein rather than DAPI. The photograph is comparable to the binary image of FIG. 1B.

FIG. 3 is a photograph of a human metaphase spread prepared and hybridized contemporaneously with the spreads shown in FIGS. 1A, B and C and 2A and B. The procedures used were the same except that PI (propidium iodide) instead of DAPI, was used to stain all the chromosomes. Both PI and fluorescein stains can be viewed with the same microscope filters. Color film was used such that the propidium iodide counterstain appears red and the fluorescein of the probe appears yellow on the color film.

FIG. 4A shows the hybridization of the chromosome 4-specific library in Bluescribe plasmids (the library pBS-4) to a human metaphase spread wherein no unlabeled human genomic DNA was used, and wherein the hybridization mixture was applied immediately after denaturation. Both copies of chromosome 4 are seen as slightly brighter than the other chromosomes. The small arrows indicate regions that are unstained with the probe. As in FIG. 3 and as in the rest of the Figures below, PI is the counterstain and fluorescein is used to label the probe.

FIG. 4B shows the hybridization of pBS-4 to a human metaphase spread wherein unlabeled human genomic DNA was used during the hybridization (Q=2 of genomic DNA; the meaning of Q is explained infra). Quantitative image analysis shows that the intensity per unit length of the chomosome 4s is about 20X that of the other chromosomes. The chromosome 4s are yellow; the other chromosomes are red due to the propidium iodide counterstain. Two layers of avidin-fluorescein isothiocyanate have been used to make the target chromosomes sufficiently bright to be measured accurately. However, the number 4 chromosomes can be recognized easily after a single layer is applied.

FIG. 4C shows the same spread as in FIG. 4B but through a filter that passes only the fluorescein isothiocyanate fluorescence.

FIG. 4D shows the detection of a radiation-induced translocation (arrows) involving chromosome 4s in a human metaphase spread wherein pBS-4 specific libraries are used. The contrast ratio is about 5X.

FIG. 4E shows that normal and two derivative chromosomes resulting from a translocation between chromosome 4 and 11 (in cell line RS4;11) can be detected by the compositions and methods of this invention in interphase nuclei. They appear as three distinct domains.

FIG. 4F shows the hybridization of the chromosome 21-specific library in Bluescribe plasmids (the library pBS-21) to a metaphase spread of a trisomy 21 cell line. A small amount of hybridization is visible near the centromeres of the other acrocentric chromosomes.

FIG. 4G shows the same hybridization as in FIG. 4F but with interphase nuclei. Clearly shown are the three chromosome 21 domains.

FIG. 4H shows the hybridization with a pool of 120 single copy probes from chromosome 4 to a human metaphase spread. The number 4 chromosomes are indicated by arrows.

DETAILED DESCRIPTION OF THE INVENTION

Figure 1A:
FIGS. 1A, B and C

This invention concerns the use of nucleic acid probes to stain targeted chromosomal material in patterns which can extend along one or more whole chromosomes, and/or along one or more regions on one or more chromosomes, including patterns which extend over an entire genome. The staining reagents of this invention facilitate the microscopic and/or flow cytometric identification of normal and aberrant chromosomes and provide for the characterization of the genetic nature of particular abnormalities. The term "chromosome-specific " is herein defined to encompass the terms "target specific" and "region specific", that is, when the staining composition is directed to one chromosome, it is chromosome-specific, but it is also chromosome-specific when it is directed, for example, to multiple regions on multiple chromosomes, or to a region of only one chromosome, or to regions across the entire genome. The term chromosome-specific originated from the use of recombinant DNA libraries made by cloning DNA from a single normal chromosome type as the source material for the initial probes of this invention. Libraries made from DNA from regions of one or more chromosomes are sources of DNA for probes for that region or those regions of the genome. The probes produced from such source material are region-specific probes but are also encompassed within the broader phrase "chromosome-specific" probes. The term "target specific" is interchangeably used herein with the term "chromosome-specific".

The word "specific" as commonly used in the art has two somewhat different meanings. The practice is followed herein. "Specific" may refer to the origin of a nucleic acid sequence or to the pattern with which it will hybridize to a genome as part of a staining reagent. For example, isolation and cloning of DNA from a specified chromosome results in a "chromosome-specific library". [Eg., Van Dilla et al., "Human Chromosome-Specific DNA Libraries: Construction and Availability," *Biotechnology,* 4:537 (1986).] However, such a library contains sequences that are shared with other chromosomes. Such shared sequences are not chromosome-specific to the chromosome from which they were derived in their hybridization properties since they will bind to more than the chromosome of origin. A sequence is "chromosome-specific" if it binds only to the desired portion of a genome. Such sequences include single-copy sequences contained in the target or repetitive sequences, in which the copies are contained predominantly in the target.

"Chromosome-specific" in modifying "staining reagent" refers to the overall hybridization pattern of the nucleic acid sequences that comprise the reagent. A staining reagent is chromosome-specific if useful contrast between the target and non-target chromosomal material is achieved (that is, that the target can be adequately visualized).

A probe is herein defined to be a collection of nucleic acid fragments whose hybridization to the target can be detected. The probe is labeled as described below so that its binding to the target can be visualized. The probe is produced from some source of nucleic acid sequences, for example, a collection of clones or a collection of polymerase chain reaction (PCR) products. The source nucleic acid may then be processed in some way, for example, by removal of repetitive sequences or blocking them with unlabeled nucleic acid with complementary sequence, so that hybridization with the resulting probe produces staining of sufficient contrast on the target. Thus, the word probe may be used herein to refer not only to the detectable nucleic acid, but also to the detectable nucleic acid in the form in which it is applied to the target, for example, with the blocking nucleic acid, etc. The blocking nucleic acid may also be mentioned separately. What "probe" refers to specifically should be clear from the context in which the word is used.

The term "labeled" is herein used to indicate that there is some method to visualize the bound probe, whether or not the probe directly carries some modified constituent. Section III infra describes various means of directly labeling the probe and other labeling means by which the bound probe can be detected.

The terms "staining" or "painting" are herein defined to mean hybridizing a probe of this invention to a genome or segment thereof, such that the probe reliably binds to the targeted chromosomal material therein and the bound probe is capable of being visualized. The terms "staining" or "painting" are used interchangeably. The patterns resulting from "staining" or "painting" are useful for cytogenetic analysis, more particularly, molecular cytogenetic analysis. The staining patterns facilitate the microscopic and/or flow cytometric identification of normal and abnormal chromosomes and the characterization of the genetic nature of particular abnormalities. Section III infra describes methods of rendering the probe visible. Since multiple compatible methods of probe visualization are available, the binding patterns of different components of the probe can be distinguished—for example, by color. Thus, this invention is capable of producing any desired staining pattern on the chromosomes visualized with one or more colors (a multicolor staining pattern) and/or other indicator methods. The term "staining" as defined herein does not include the concept of staining chromosomes with chemicals as in conventional karotyping methods although such conventional stains may be used in conjunction with the probes of this invention to allow visualization of those parts of the genome where the probe does not bind. The use of DAPI and propidium iodide for such a purpose is illustrated in the figures.

The phrase "high complexity" is defined herein to mean that the probe, thereby modified contains on the order of 50,000 (50 kb) or greater, up to many millions or several billions, of bases of nucleic acid sequences which are not repeated in the probe. For example, representative high complexity nucleic acid probes of this invention can have a complexity greater than 50 kb, greater than 100,000 bases (100 kb), greater than 200,000 (200 kb), greater than 500,000 bases (500 kb), greater than one million bases (1 Mb), greater than 2 Mb, greater than 10 Mb, greater than 100 Mb, greater than 500 Mb, greater than 1 billion bases and still further greater than several billion bases.

The term "complexity" is defined herein according to the standard for nucleic acid complexity as established by Britten et al., *Methods of Enzymol.,* 29:363 (1974). See also Cantor and Schimmel, *Biophysical Chemistry: Part III: The Behavior of Biological Macromolecules,* at 1228–1230 (Freeman and Co. 1980) for further explanation and exemplification of nucleic acid complexity.

The complexity preferred for a probe composition of this invention is dependent upon the application for which it is designed. In general, the larger the target area, the more complex is the probe. It is anticipated that the complexity of a probe needed to produce a desired pattern of landmarks on a chromosome will decrease as hybridization sensitivity increases, as progress is made in hybridization technology. As the sensitivity increases, the reliability of the signal from smaller target sites will increase. Therefore, whereas from about a 40 kb to about a 100 kb target sequence may be presently necessary to provide a reliable, easily detectable signal, smaller target sequences should provide reliable signals in the future. Therefore, as hybridization sensitivity increases, a probe of a certain complexity, for example, 100 kb, should enable the user to detect considerably more loci in a genome than are presently reliably detected; thus, more information will be obtained with a probe of the same complexity. The term "complexity" therefore refers to the complexity of the total probe no matter how many visually distinct loci are to be detected, that is, regardless of the distribution of the target sites over the genome.

As indicated above, with current hybridization techniques it is possible to obtain a reliable, easily detectable signal with a probe of about 40 kb to about 100 kb (eg. the probe insert capacity of one or a few cosmids) targeted to a compact point in the genome. Thus, for example, a complexity in the range of approximately 100 kb now permits hybridization to both sides of a tumor-specific translocation. The portion of the probe targeted to one side of the breakpoint can be labeled differently than that targeted to the other side of the breakpoint so that the two sides can be differentiated with different colors, for example. Proportionately increasing the complexity of the probe permits analysis of multiple compact regions of the genome simultaneously. The conventional banding patterns produced by chemical stains may be replaced according to this invention with a series of probe-based, color coded (for example), reference points along each chromosome or significant regions thereof.

Uniform staining of an extended contiguous region of a genome, for example, a whole chromosome, requires a probe complexity proportional to but substantially less than, the complexity of the target region. The complexity required is only that necessary to provide a reliable, substantially uniform signal on the target. Section V.B, infra, demonstrates that fluorescent staining of human chromosome 21, which contains about 50 megabases (Mb) of DNA, is sufficient with a probe complexity of about 1 Mb. FIG. 4H illustrates hybridization of about 400 kb of probe to human chromosome 4, which contains about 200 Mb of DNA. In that case, gaps between the hybridization of individual elements of the probe are visible. FIGS. 4B and 4F demonstrate the results achieved with probes made up of entire libraries for chromosomes 4 and 21, respectively. The chromosomes are stained much more densely as shown in FIGS. 4B and 4F than with the lower complexity probe comprising single-copy nucleic acid sequences used to produce the pattern of FIG. 4H.

Increasing the complexity beyond the minimum required for adequate staining is not detrimental as long as the total nucleic acid concentration in the probe remains below the point where hybridization is impaired. The decrease in concentration of a portion of a sequence in the probe is compensated for by the increase in the number of target sites. In fact, when using double-stranded probes, it is preferred to maintain a relatively low concentration of each portion of sequence to inhibit reassociation before said portion of sequence can find a binding site in the target.

The staining patterns of this invention comprise one or more "bands". The term "band" is herein defined as a reference point in a genome which comprises a target nucleic acid sequence bound to a probe component, which duplex is detectable by some indicator means, and which at its narrowest dimension provides for a reliable signal under the conditions and protocols of the hybridization and the instrumentation, among other variables, used. A band can extend from the narrow dimension of a sequence providing a reliable signal to a whole chromosome to multiple regions on a number of chromosomes.

The probe-produced bands of this invention are to be distinguished from bands produced by chemical staining as indicated above in the Background. The probe-produced bands of this invention are based upon nucleic acid sequence whereas the bands produced by chemical staining depend on natural characteristics of the chromosomes, but not the actual nucleic acid sequence. Further, the banding patterns produced by chemical staining are only interpretable in terms of metaphase chromosomes whereas the probe-produced bands of this invention are useful both for metaphase and interphase chromosomes.

One method of forming the probes of the present invention is to pool many different low complexity probes. Such a probe would then comprise a "heterogeneous mixture" of individual cloned sequences. The number of clones required depends on the extent of the target area and the capacity of the cloning vector. If the target is made up of several discrete, compact loci, that is, single spots at the limit of microscopic resolution, then about 40 kb, more preferably 100 kb, for each spot gives a reliable signal given current techniques. The portion of the probe for each spot may be made up from, for example, a single insert from a yeast artificial chromosome (YAC), from several cosmids each containing 35–40 kb or probe sequence, or from about 25 plasmids each with 4 kb of sequence.

Representative heterogeneous mixtures of clones exemplified herein include phage (FIGS. 1, 2 and 3), and plasmids (FIG. 4). Yeast artificial chromosomes (YACS) (FIG. 5), and a single human chromosome in an inter-species hybrid cell (FIG. 6) are examples of high complexity probes for single loci and an entire chromosome that can be propagated as a single clone.

A base sequence at any point in the genome can be classified as either "single-copy" or "repetitive". For practical purposes the sequence needs to be long enough so that a complementary probe sequence can form a stable hybrid with the target sequence under the hybridization conditions being used. Such a length is typically in the range of several tens to hundreds of nucleotides.

A "single-copy sequence" is that wherein only one copy of the target nucleic acid sequence is present in the haploid genome. "Single-copy sequences" are also known in the art as "unique sequences". A "repetitive sequence" is that wherein there are more than one copy of the same target nucleic acid sequence in the genome. Each copy of a repetitive sequence need not be identical to all the others. The important feature is that the sequence be sufficiently similar to the other members of the family of repetitive sequences such that under the hybridization conditions being used, the same fragment of probe nucleic acid is capable of forming stable hybrids with each copy.

A "shared repetitive sequence" is a sequence with some copies in the target region of the genome, and some elsewhere.

When the adjectives "single-copy", "repetitive", "shared repetitive", among other such modifiers, are used to describe sequences in the probe, they refer to the type of sequence in the target to which the probe sequence will bind. Thus, "a repetitive probe" is one that binds to a repetitive sequence in the target; and "a single-copy probe" binds to a single-copy target sequence.

Repetitive sequences occur in multiple copies in the haploid genome. The number of copies can range from two to hundreds of thousands, wherein the Alu family of repetitive DNA are exemplary of the latter numerous variety. The copies of a repeat may be clustered or interspersed throughout the genome. Repeats may be clustered in one or more locations in the genome, for example, repetitive sequences occurring near the centromeres of each chromosome, and variable number tandem repeats (VNTRs) [Nakamura et al, Science, 235: 1616 (1987)]; or the repeats may be distributed over a single chromosome [for example, repeats found only on the X chromosome as described by Bardoni et al., Cytogenet. Cell Genet., 46: 575 (1987)]; or the repeats may be distributed over all the chromosomes, for example, the Alu family of repetitive sequences.

Herein, the terms repetitive sequences, repeated sequences and repeats are used interchangeably.

Shared repetitive sequences can be clustered or interspersed. Clustered repetitive sequences include tandem repeats which are so named because they are contiguous on the DNA molecule which forms the backbone of a chromosome. Clustered repeats are associated with well-defined regions of one or more chromosomes, e.g., the centromeric region. If one or more clustered repeats form a sizable fraction of a chromosome, and are shared with one or more non-target regions of the genome and are consequently removed from the heterogeneous mixture of fragments employed in the invention or the hybridization capacity thereof is disabled, perfect uniformity of staining of the target region may not be possible. That situation is comprehended by the use of the term "substantially uniform" in reference to the binding of the heterogeneous mixture of labeled nucleic acid fragments to the target.

Chromosome-specific staining of the current invention is accomplished by using nucleic acid fragments that hybridize to sequences specific to the target. These sequences may be either single-copy or repetitive, wherein the copies of the repeat occur predominantly in the target area. FIG. 4H and the results of the work detailed in section V infra indicate that probes can be made of single-copy sequences. However, in probes such as that of FIG. 4B, low-copy chromosome-specific repeats [Nakamura et al., and Bardoni et al., supra] may contribute to the hybridization as well.

If nucleic acid fragments complementary to non-target regions of the genome are included in the probe, for example, shared repetitive sequences or non-specific sequences, their hybridization capacity needs to be sufficiently disabled or their prevalence sufficiently reduced, so that adequate staining contrast can be obtained. Section V and FIG. 4H show examples of hybridization with probes that contain pools of clones in which each clone has been individually selected so that it hybridizes to single-copy sequences or very low copy repetitive sequences. The remaining figures illustrate use of probes that contain fragments that could have hybridized to high-copy repetitive sequences, but which have had the hybridization capacity of such sequences disabled.

The nucleic acid probes of this invention need not be absolutely specific for the targeted portion of the genome. They are intended to produce "staining contrast". "Contrast" is quantified by the ratio of the stain intensity of the target region of the genome to that of the other portions of the genome. For example, a DNA library produced by cloning a particular chromosome, such as those listed in Table I, can be used as a probe capable of staining the entire chromosome. The library contains sequences found only on that chromosome, and sequences shared with other chromosomes. In a simplified (approximately true to life) model of the human genome, about half of the chromosomal DNA falls into each class. If hybridization with the whole library were capable of saturating all of the binding sites, the target chromosome would be twice as bright (contrast ratio of 2) as the others since it would contain signal from the specific and shared sequences in the probe, whereas the other chromosome would only have signal from the shared sequences. Thus, only a modest decrease in hybridization of the shared sequences in the probe would substantially enhance the contrast. Contaminating sequences which only hybridize to non-targeted sequences, for example, impurities in a library, can be tolerated in the probe to the extent that said sequences do not reduce the staining contrast below useful levels.

In reality all of the target sites may not be saturated during the hybridization, and many other mechanisms contribute to producing staining contrast, but this model illustrates one general consideration in using probes targeted at a large portion of a genome.

The required contrast depends on the application for which the probe is designed. When visualizing chromosomes and nuclei, etc., microscopically, a contrast ratio of two or greater is often sufficient for identifying whole chromosomes. In FIGS. 4D–F, the contrast ratio is 3–5. The smaller the individual segments of the target region, the greater the contrast needs to be to permit reliable recognition of the target relative to the fluctuations in staining of the non-targeted regions. When quantifying the amount of target region present in a cell nucleus by fluorescence intensity measurements using flow cytometry or quantitative microscopy, the required contrast ratio is on the order of $1/T$ or greater on average for the genome, where T is the fraction of the genome contained in the targeted region. When the contrast ratio is equal to 1/T, half of the total fluorescence intensity comes from the target region and half from the rest of the genome. For example, when using a high complexity probe for chromosome 1, which comprises about 10% of the genome, the required contrast ratio is on the order of 10, that is, for the chromosome 1 fluorescence intensity to equal that of the rest of the genome.

Background staining by the probe, that is, to the non-target region of the genome, may not be uniform. FIG. 4F shows that a chromosome 21 specific probe contains probe fragments that hybridize weakly to compact regions near the centromeres of other acrocentric human chromosomes. This degree of non-specificity does not inhibit its use in the illustrated applications. For other applications, removal of or further disabling the hybridization capacity of the probe fragments that bind to these sequences may be necessary.

For other applications, repetitive sequences that bind to centromeres, for example, alpha-satellite sequences, and/or telomeres can be part of the chromosome-specific staining reagents wherein the target includes some or all of the centromeres and/or telomeres in a genome along with perhaps other chromosomal regions. Exemplary of such an application would be that wherein the staining reagent is designed to detect random structural aberrations caused by clastogenic agents that result in dicentric chromosomes and other structural abnormalities, such as translocations. Addition of sequences which bind to all centromeres in a genome, for example to the probe used to create the staining pattern of FIG. 4D, would allow more reliable distinguishing between dicentrics and translocations.

Application of staining reagents of this invention to a genome results in a substantially uniform distribution of probe hybridized to the targeted regions of a genome. The distribution of bound probe is deemed "substantially uniform" if the targeted regions of the genome can be visualized with useful contrast. For example, a target is substantially uniformly stained in the case wherein it is a series of visually separated loci if most of the loci are visible in most of the cells.

"Substantial proportions" in reference to the base sequences of nucleic acid fragments that are complementary to chromosomal DNA means that the complementarity is extensive enough so that the fragments form stable hybrids with the chromosomal DNA under the hybridization conditions used. In particular, the term comprehends the situation where the nucleic acid fragments of the heterogeneous mixture possess some regions of sequence that are not perfectly complementary to target chromosomal material. The stringency can be adjusted to control the precision of the complementarity required for hybridization.

The phrase "metaphase chromosomes" is herein defined to mean not only chromosomes condensed in the metaphase stage of mitosis but includes any condensed chromosomes, for example, those condensed by premature chromosome condensation.

To disable the hybridization capacity of a nucleic acid sequence is herein sometimes abbreviated as "disabling the nucleic acid sequence".

The following sections provide examples of making and using the staining compositions of this invention and are for purposes of illustration only and not meant to limit the invention in any way. The following abbreviations are used. Abbreviations BN—bicarbonate buffer with NP-40
DAPI—4,6-diamidino-2-phenylindole DCS—as in fluorescein-avidin DCS (a commercially available cell sorter grade of fluorescein Avidin D)
AAF—N-acetoxy-N-2-acetyl-aminofluorene
EDTA—ethylenediaminetetraacetate
FACS—fluorescence-activated cell sorting
FITC—fluorescein isothiocyanate
IB—isolation buffer
NP-40—non-ionic detergent commercially available from Sigma as Nonidet P-40 (St. Louis, Mo.)
PBS—phosphate-buffered saline
PI—propidium iodide
PMSF—phenylmethylsulfonyl fluoride
PN—mixture of 0.1 M $NaH_2PO_4$ and 0.1 M buffer $Na_2HPO_4$, pH 8; 0.1% NP-40
PNM—Pn buffer plus 5% nonfat dry milk (centrifuged); buffer 0.02% Na azide
SDS—sodium dodecyl sulfate
SSC—0.15 M NaCl/0.015 M Na citrate, pH 7
VNTR—variable number tandem repeat I. Methods of Preparing Chromosome-Specific Staining Reagents I.A. Isolation of Chromosome-Specific DNA and Formation of DNA Fragment Libraries.

The first step in a preferred method of making the compositions of the invention is isolating chromosome-specific DNA (which term includes target-specific and/or region-specific DNA, as indicated above, wherein specific refers to the origin of the DNA). This step includes first isolating a sufficient quantity of the particular chromosome type or chromosomal subregion to which the staining composition is directed, then extracting the DNA from the isolated chromosome(s) or chromosomal subregion(s). Here "sufficient quantity" means sufficient for carrying out subsequent steps of the method. Preferably, the extracted DNA is used to create a library of DNA inserts by cloning using standard genetic engineering techniques.

Preferred cloning vectors include, but are not limited to, yeast artificial chromosomes (YACS), plasmids, bacteriophages and cosmids. Preferred plasmids are Bluescribe plasmids; preferred bacteriophages are lambda insertion vectors, more preferably Charon 4A, Charon 21A, Charon 35, Charon 40 and GEM11; and preferred cosmids include Lawrist 4, Lawrist 5 and sCos1.

As indicated above, the DNA can be isolated from any source. Chromosome-specific staining reagents can be made from both plant and animal DNA according to the methods of this invention. Important sources of animal DNA are mammals, particularly primates or rodents wherein primate sources are more particularly human and monkey, and rodent sources are more particularly rats or mice, and more particularly mice.

1. Isolating DNA from an Entire Chromosome. A preferred means for isolating particular whole chromosomes (specific chromosome types) is by direct flow sorting [fluorescence-activated cell sorting (FACS)] of metaphase chromosomes with or without the use of interspecific hybrid cell systems. For some species, every chromosome can be isolated by currently available sorting techniques. Most, but not all, human chromosomes are currently isolatable by flow sorting from human cells, Carrano et al., "Measurement and Purification of Human Chromosomes by Flow Cytometry and Sorting," *Proc. Natl. Acad. Sci.*, Vol. 76, pgs. 1382–1384 (1979). Thus, for isolation of some human chromosomes, use of the human/rodent hybrid cell system may be necessary, see Kao, "Somatic Cell Genetics and Gene Mapping," *International Review of Cytology.* Vol. 85, pgs. 109–146 (1983), for a review, and Gusella et al., "Isolation and Localization of DNA Segments from Specific Human Chromosomes," *Proc. Natl. Acad. Sci.,* Vol. 77, pgs. 2829–2833 (1980). Chromosome sorting can be done by commercially available fluorescence-activated sorting machines, e.g., Becton Dickinson FACS-II, Coulter Epics V sorter, or special purpose sorters optimized for chromosome sorting or like instrument.

DNA is extracted from the isolated chromosomes by standard techniques, e.g., Marmur, "A Procedure for the Isolation of Deoxyribonucleic Acid from Micro-Organisms," *J. Mol. Biol.,* Vol. 3, pgs. 208–218 (1961); or Maniatis et al., *Molecular Cloning: A Laboratory Manual* (Cold Spring Harbor Laboratory, 1982) pgs. 280–281. These references are incorporated by reference for their descriptions of DNA isolation techniques.

Generation of insert libraries from the isolated chromosome-specific DNA is carried out using standard genetic engineering techniques, e.g., Davies et al., "Cloning of a Representative Genomic Library of the Human X Chromosome After Sorting by Flow Cytometry," *Nature,* Vol. 293, pgs. 374–376 (1981); Krumlauf et al., "Construction and Characterization of Genomic Libraries from Specific Human Chromosomes," *Proc. Natl. Acad. Sci.,* Vol. 79, pgs. 2971–2975 (1982); Lawn et al., "The Isolation and Characterization of Linked Delta-and-Beta-Globin Genes from a Cloned Library of Human DNA." *Cell,* Vol. 15, pgs. 1157–1174 (1978); and Maniatis et al., "Molecular Cloning: A Laboratory Manual," (Cold Springs Harbor Laboratory, 1982), pgs. 256–308; Van Dilla et al., id; Fuscoe, Gene, 52:291 (1987); and Fuscoe et al., *Cytogenet. Cell Genet.,* 43:79 (1986). Said references are herein incorporated by reference.

Recombinant DNA libraries for each of the human chromosomes have been constructed by the National Laboratory Gene Library Project and are available from the American Type Culture Collection. [Van Dilla et al., *Biotechnology,* 4:537 (1986).] Small insert-containing libraries were constructed by complete digestion of flow sorted human chromosome genomic DNA with HindIII or EcoRI and cloning into the Lambda insertion vector Charon 21A. The vector is capable of accepting human inserts of up to 9.1 kb in size. Thus, HindIII (or EcoRI) restriction fragments greater than 9.1 kb will not be recovered from these libraries. The observed average insert size in these libraries is approximately 4 kb. A representative list of the HindIII chromosome-specific libraries with their ATCC accession numbers are shown in Table 1.

TABLE 1

HUMAN CHROMOSOME - SPECIFIC GENOMIC LIBRARIES IN CHARON 21A VECTOR

| CHROMOSOME | ATCC # | LIBRARY |
|---|---|---|
| 1 | 57753 | LL01NS01 |
| 1 | 57754 | LL01NS02 |
| 2 | 57744 | LL02NS01 |
| 3 | 57751 | LL03NS01 |
| 4 | 57700 | LL04NS01 |
| 4 | 57745 | LL04NS02 |
| 5 | 57746 | LL05NS01 |
| 6 | 57701 | LL06NS01 |
| 7 | 57755 | LL07NS01 |
| 8 | 57702 | LL08NS02 |
| 9 | 57703 | LL09NS01 |
| 10 | 57736 | LL10NS01 |
| 11 | 57704 | LL11NS01 |
| 12 | 57756 | LL12NS01 |

TABLE 1-continued

HUMAN CHROMOSOME - SPECIFIC GENOMIC LIBRARIES IN CHARON 21A VECTOR

| CHROMOSOME | ATCC # | LIBRARY |
|---|---|---|
| 13 | 57705 | LL13NS01 |
| 13 | 57757 | LL13NS02 |
| 14 | 57706 | LL14NS01 |
| 14/15 | 57707 | LL99NS01 |
| 15 | 57737 | LL15NS01 |
| 16 | 57758 | LL16NS03 |
| 17 | 57759 | LL17NS02 |
| 18 | 57710 | LL18NS01 |
| 19 | 57711 | LL19NS01 |
| 20 | 57712 | LL20NS01 |
| 21 | 57713 | LL21NS02 |
| 22 | 57714 | LL22NS01 |
| X | 57747 | LL0XNS01 |
| Y | 57715 | LL0YNS01 |

Alternatively, the extracted DNA from a sorted chromosome type can be amplified by the polymerase chain reaction (PCR) rather than cloning the extracted DNA in a vector or propagating it in a cell line. Appropriate tails are added to the extracted DNA in preparation for PCR. References for such PCR procedures are set out in Section I.B infra.

Other possible methods of isolating the desired sequences from hybrid cells include those of Schmeckpeper et al., "Partial Purification and Characterization of DNA from Human X Chromosome," *Proc. Natl. Acad. Sci.,* Vol. 76, pgs. 6525–6528 (1979); or Olsen et al., supra (in Background). Accordingly, these references are incorporated by reference.

2. Isolating DNA from a Portion of a Chromosome. Among the methods that can be used for isolating region-specific chromosomal DNA include the selection of an appropriate chromosomal region from DNA that has previously been mapped, for example, from a library of mapped cosmids; the sorting of derivative chromosomes, for example, by FACS; the microdissection of selected chromosomal material; subtractive hybridization; identification of an appropriate hybrid cell containing a desired chromosomal fragment, extracting and amplifying the DNA, and selecting the desired amplified DNA; and the selection of appropriate chromosomal material from radiation hybrids. The standard genetic engineering techniques outlined above in subsection I.A.1 are used in such procedures well-known to those in the art. Amplification of the region-specific DNA can be performed by cloning in an appropriate vector, propagating in an appropriate cell line, and/or by the use of PCR (see I.B infra).

A preferred method of isolating chromosomal region-specific DNA is to use mapped short DNA sequences to probe a library of longer DNA sequences, wherein the latter library has usually been cloned in a different vector. For example, a probe cloned in a plasmid can be used to probe a cosmid or yeast artificial chromosome (YAC) library. By using an initial seed probe, overlapping clones in the larger insert library can be found (a process called "walking"), and a higher complexity probe can be produced for reliable staining of the chromosomal region surrounding the seed probe. Ultimately, when an entire genome for a species has been mapped (for example, by the Human Genome Project for the human species), ordered clones for the entire genome of the species will be available. One can then easily select the appropriate clones to form a probe of the desired specificity.

Another method of isolating DNA from a chromosomal region or regions (or also a whole chromosome) is to propagate such a chromosomal region or regions in an appropriate cell line (for example, a hybrid cell line such as a human/hamster hybrid cell), extract the DNA from the cell line and clone it in an appropriate vector and select clones containing human DNA to form a library. When a hybrid cell is used, the chromosomes in the hybrid cell containing the human chromosomal material may be separated by flow sorting (FACS) prior to cloning to increase the frequency of human clones in the library. Still further, total DNA from the hybrid cell can be isolated and labeled without further cloning and used as a probe, as exemplified in FIG. 6.

3. Single-Stranded Probes. In some cases, it is preferable that the nucleic acid fragments of the heterogeneous mixture consist of single-stranded RNA or DNA. Under some conditions, the binding efficiency of single-stranded nucleic acid probes has been found to be higher during in situ hybridization, e.g., Cox et al., "Detection of mRNAs in Sea Urchin Embryos by In Situ Hybridization Using Asymmetric RNA Probes," *Developmental Biology,* Vol. 101, pgs. 485–502 (1984).

Standard methods are used to generate RNA fragments from isolated DNA fragments. For example, a method developed by Green et al., described in *Cell,* Vol. 32, pgs. 681–694 (1983), is commercialy available from Promega Biotec (Madison, Wis.) under the tradename "Riboprobe." Other transcription kits suitable for use with the present invention are available from United States Biochemical Corporation (Cleveland, Ohio) under the tradename "Genescribe." Single-stranded DNA probes can be produced with the single-stranded bacteriophage M13, also available in kit form, e.g. Bethesda Research Laboratories (Gaithersburg, Md.). The hybridizations illustrated in FIG. 4 were performed with the libraries of Table 1 subcloned into the Bluescribe plasmid vector (Stratagene, La Jolla, Calif.). The Bluescribe plasmid contains RNA promoters which permit production of single-stranded probes.

Co-pending, commonly owned U.S. patent application Ser. No. 934,188 (filed Nov. 24, 1986), entitled "Method of Preparing and Applying Single Stranded DNA Probes to Double Stranded Target DNAs," provides methods for preparing and applying non-self-complementary single-stranded nucleic acid probes that improve signal-to-noise ratios attainable in in situ hybridization by reducing non-specific and mismatched binding of the probe. That application further provides for methods of denaturing double-stranded target nucleic acid which minimizes single-stranded regions available for hybridization that are non-complementary to probe sequences. Said application is herein specifically incorporated by reference. Briefly, probe is constructed by treating DNA with a restriction enzyme and an exonuclease to form template/primers for a DNA polymerase. The digested strand is resynthesized in the presence of labeled nucleoside triphosphate precursor, and the labeled single-stranded fragments are separated from the resynthesized fragments to form the probe. The target nucleic acid is treated with the same restriction enzyme used to construct the probe, and is treated with an exonuclease before application of the probe.

I.B. PCR

Another method of producing probes of this invention includes the use of the polymerase chain reaction [PCR]. [For an explanation of the mechanics of PCR, see Saiki et al., *Science,* 230:1350 (1985) and U.S. Pat. Nos. 4,683,195, 4,683,202 (both issued Jul. 28, 1987) and U.S. Pat. No. 4,800,159 (issued Jan. 24, 1989).] Target-specific nucleic acid sequences, isolated as indicated above, can be amplified by PCR to produce target-specific sequences which are reduced in or free of repetitive sequences. The PCR primers used for such a procedure are for the ends of the repetitive sequences, resulting in amplification of sequences flanked by the repeats.

Figure 7:
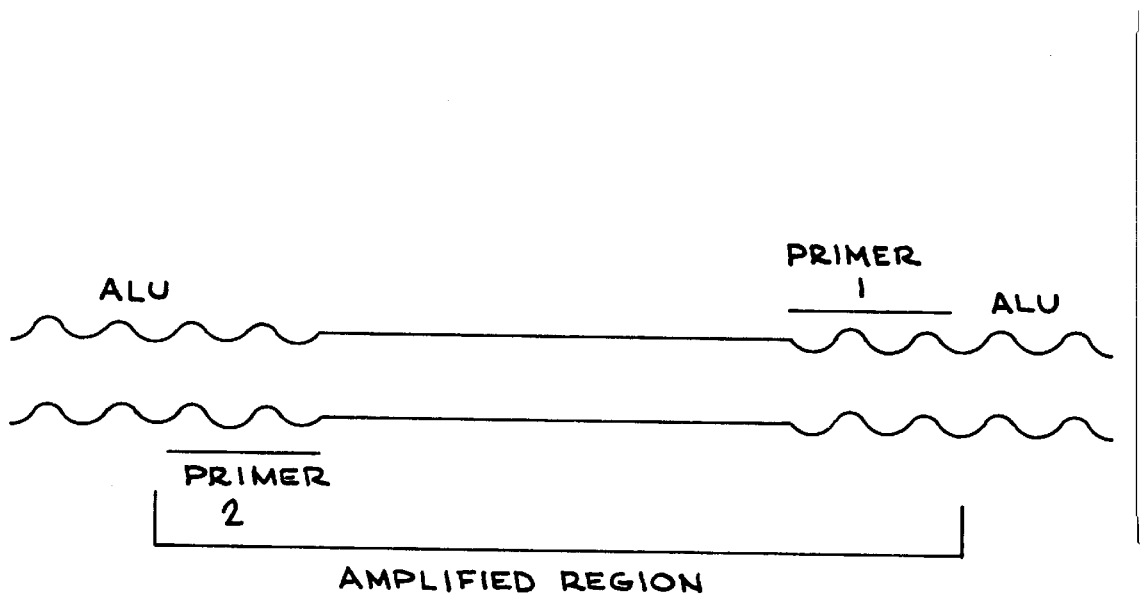
FIG. 7 illustrates a representative method of using the polymerase chain reaction (PCR) to produce probes of this invention which are reduced in repetitive sequences.

FIG. 7 illustrates such a method of using PCR wherein the representative repetitive sequence is Alu. If only short segments are amplified, it is probable that such sequences are free of other repeats, thus providing DNA reduced in repetitive sequences.

One can further suppress production of repetitive sequences in such a PCR procedure by first hybridizing complementary sequences to said repetitive sequence wherein said complementary sequences have extended non-complementary flanking ends or are terminated in nucleotides which do not permit extension by the polymerase. The non-complementary ends of the blocking sequences prevent the blocking sequences from acting as a PCR primer during the PCR process.

II. Removal of Repetitive Sequences and/or Disabling the Hybridization Capacity of Repetitive Sequences Typically a probe of the current invention is produced in a number of steps including: obtaining source nucleic acid sequences that are complementary to the target region of the genome, labeling and otherwise processing them so that they will hybridize efficiently to the target and can be detected after they bind, and treating them to either disable the hybridization capacity or remove a sufficient proportion of shared repetitive sequences, or both disable and remove such sequences. The order of these steps depends on the specific procedures employed.

The following methods can be used to remove shared repetitive sequences and/or disable the hybridization capacity of such shared repetitive sequences. Such methods are representative and are expressed schematically in terms of procedures well known to those of ordinary skill the art, and which can be modified and extended according to parameters and procedures well known to those in the art.

1. Single-copy probes. A single-copy probe consists of nucleic acid fragments that are complementary to single-copy sequences contained in the target region of the genome. One method of constructing such a probe is to start with a DNA library produced by cloning the target region. Some of the clones in the library will contain DNA whose entire sequence is single-copy; others will contain repetitive sequences; and still others will have portions of single-copy and repetitive sequences. Selection, on a clone by clone basis, and pooling of those clones containing only single-copy sequences will result in a probe that will hybridize specifically to the target region. The single-copy nature of a clone can ultimately be established by Southern hybridization using standard techniques. FIG. 4H shows hybridization with 120 clones selected in this way from a chromosome 4 library.

Southern analysis is very time consuming and labor intensive. Therefore, less perfect but more efficient screening methods for obtaining candidate single-copy clones are useful. In Section V.B, examples of improved methods are provided for screening individual phage and plasmid clones for the presence of repetitive DNA using hybridization with genomic DNA. The screening of plasmid clones is more efficient, and approximately 80% of selected clones contain only single-copy sequences; the remainder contain low-copy repeats. However, probes produced in this way can produce adequate staining contrast, indicating that the low-copy repetitive sequences can be tolerated in the probe (see subsection 3 of this section).

A disadvantage of clone by clone procedures is that a clone is discarded even if only a portion of the sequence it contains is repetitive. The larger the length of the cloned nucleic acid, the greater the chance that it will contain a repetitive sequence. Therefore, when nucleic acid is propagated in a vector that contains large inserts such as a cosmid, YAC, or in a cell line, such as hybrid cells, it may be advantageous to subclone it in smaller pieces before the single-copy selection is performed. The selection procedures just outlined above do not discriminate between shared and specific repetitive sequences; clones with detectable repetitive sequences of either type are not used in the probe.

2. Individual testing of hybridization properties. The hybridization specificity of a piece of nucleic acid, for example, a clone, can be tested by in situ hybridization. If under appropriate hybridization conditions it binds to single-copy or repetitive sequences specific for the desired target region, it can be included in the probe. Many sequences with specific hybridization characteristics are already known, such as chromosome-specific repetitive sequences [Trask et al., supra, (1988) and references therein], VNTRs, numerous mapped single copy sequences. More are continuously being mapped. Such sequences can be included in a probe of this invention.

3. Bulk Procedures. In many genomes, such as the human genome, a major portion of shared repetitive DNA is contained in a few families of highly repeated sequences such as Alu. A probe that is substantially free of such high-copy repetitive sequences will produce useful staining contrast in many applications. Such a probe can be produced from some source of nucleic acid sequences, for example, the libraries of Table I, with relatively simple bulk procedures. Therefore, such bulk procedures are the preferred methods for such applications.

These methods primarily exploit the fact that the hybridization rate of complementary nucleic acid strands increases as their concentration increases. Thus, if a heterogeneous mixture of nucleic acid fragments is denatured and incubated under conditions that permit hybridization, the sequences present at high concentration will become double-stranded more rapidly than the others. The double-stranded nucleic acid can then be removed and the remainder used as a probe. Alternatively, the partially hybridized mixture can be used as the probe, the double-stranded sequences being unable to bind to the target. The following are methods representative of bulk procedures that are useful for producing the target-specific staining of this invention.

3a. Self-reassociation of the probe. Double-stranded probe nucleic acid in the hybridization mixture is denatured and then incubated under hybridization conditions for a time sufficient for the high-copy sequences in the probe to become substantially double-stranded. The hybridization mixture is then applied to the sample. The remaining labeled single-stranded copies of the highly repeated sequences bind throughout the sample producing a weak, widely distributed signal. The binding of the multiplicity of low-copy sequences specific for the target region of the genome produce an easily distinguishable specific signal.

Such a method is exemplified in Section VI.B (infra) with chromosome-specific libraries for chromosomes 4 and 21 (pBS4 and pBS21) as probes for those chromosomes. The hybridization mix, containing a probe concentration in the range of 1–10 ng/ul was heated to denature the probe and incubated at 37° C. for 24 hours prior to application to the sample.

3b. Use of blocking nucleic acid. Unlabeled nucleic acid sequences which are complementary to those sequences in the probe whose hybridization capacity it is desired to inhibit are added to the hybridization mixture. The probe and blocking nucleic acid are denatured, if necessary, and incubated under appropriate hybridization conditions. The sequences to be blocked become double-stranded more rapidly than the others, and therefore are unable to bind to the target when the hybridization mixture is applied to the target. In some cases, the blocking reaction occurs so quickly that the incubation period can be very short, and adequate results can be obtained if the hybridization mix is applied to the target immediately after denaturation. A blocking method is generally described by Sealy et al., "Removal of Repeat Sequences form Hybridization Probes", *Nucleic Acid Research,* 13:1905 (1985), which reference is incorporated by reference. Examples of blocking nucleic acids include genomic DNA, a high-copy fraction of genomic DNA and particular sequences as outlined below (i–iii).

3b.i. Genomic DNA. Genomic DNA contains all of the nucleic acid sequences of the organism in proportion to their copy-number in the genome. Thus, adding genomic DNA to the hybridization mixture increases the concentration of the high-copy repeat sequences more than low-copy sequences, and therefore is more effective at blocking the former. However, the genomic DNA does contain copies of the sequences that are specific to the target and so will also reduce the desired chromosome-specific binding if too much is added. Guidelines to determine how much genomic DNA to add (see 3.e. Concept of Q, infra) and examples of using genomic blocking DNA are provided below. The blocking effectiveness of genomic DNA can be enhanced under some conditions by adjusting the timing of its addition to the hybridization mix; examples of such timing adjustments are provided with Protocol I and Protocol II hybridizations illustrated in FIGS. 4B through E (Protocol I) and FIG. 4F (Protocol II) and detailed in Section VI, infra.

3b.ii. High-copy fraction of genomic DNA. The difficulty with use of genomic DNA is that it also blocks the hybridization of the low-copy sequences, which are predominantly the sequences that give the desired target staining. Thus, fractionating the genomic DNA to obtain only the high-copy sequences and using them for blocking overcomes this difficulty. Such fractionation can be done, for example, with hydroxyapatite as described below (3c.i).

3b.iii. Specified sequences. The blocking of a particular sequence in the probe can be accomplished by adding many unlabeled copies of that sequence. For example, Alu sequences in the probe can be blocked by adding cloned Alu DNA. Blocking DNA made from a mixture of a few clones containing the highest copy sequences in the human genome can be used effectively with chromosome-specific libraries for example, those of Table I. Alternatively, unlabeled nucleic acid sequences from one or more chromosome-specific libraries could be used to block a probe containing labeled sequences from one or more other chromosome-specific libraries. The shared sequences would be blocked whereas sequences occurring only on the target chromosome would be unaffected. FIG. 4F shows that genomic DNA was not effective in completely blocking the hybridization of a sequence or sequences shared by human chromosome 21 and the centromeric regions of the other human acrocentric chromosomes. When a clone or clones containing such a sequence or sequences is or are eventually isolated, unlabeled DNA produced therefrom could be added to the genomic blocking DNA to improve the specificity of the staining.

3c. Removal of Sequences.

3c.i. Hydroxyapatite. Single- and double-stranded nucleic acids have different binding characteristics to hydroxyapatite. Such characteristics provide a basis commonly used for fractionating nucleic acids. Hydroxyapatite is commerically available (eg. Bio-Rad Laboratories, Richmond, Calif.). The fraction of genomic DNA containing sequences with a particular degree of repetition, from the highest copy-number to single-copy, can be obtained by denaturing genomic DNA, allowing it to reassociate under appropriate conditions to a particular value of $C_o t$, followed by separation using hydroxyapatite. The single- and double-stranded nucleic acid can also be discriminated by use of S1 nuclease. Such techniques and the concept of $C_o t$ are explained in Britten et al., "Analysis of Repeating DNA Sequences by Reassociation", in *Methods in Enzymology*, Vol. 29, pgs 363–418 (1974), which article is herein incorporated by reference.

The single-stranded nucleic acid fraction produced in 3a. or 3b. above can be separated by hydroxyapatite and used as a probe. Thus, the sequences that have been blocked (that become double-stranded) are physically removed. The probe can then be stored until needed. The probe can then be used without additional blocking nucleic acid, or its staining contrast can perhaps be improved by additonal blocking.

3c.ii. Reaction with immobilized nucleic acid. Removal of particular sequences can also be accomplished by attaching single-stranded "absorbing" nucleic acid sequences to a solid support. Single-stranded source nucleic acid is hybridized to the immobilized nucleic acid. After the hybridization, the unbound sequences are collected and used as the probe. For example, human genomic DNA can be used to absorb repetitive sequences from human probes. One such method is described by Brison et al., "General Method for Cloning Amplified DNA by Differential Screening with Genomic Probes," *Molecular and Cellular Biology*, Vol. 2, pgs. 578–587 (1982). Accordingly, that reference is incorporated by reference. Briefly, minimally sheared human genomic DNA is bound to diazonium cellulose or a like support. The source DNA, appropriately cut into fragments, is hybridized against the immobilized DNA to $C_o t$ values in the range of about 1 to 100. The preferred stringency of the hybridization conditions may vary depending on the base composition of the DNA. Such a procedure could remove repetitive sequences from chromosome-specific libraries, for example, those of Table I, to produce a probe capable of staining a whole human chromosome.

3d. Blocking non-targeted sequences in the targeted genome. Blocking of non-targeted binding sites in the targeted genome by hybridization with unlabeled complementary sequences will prevent binding of labeled sequences in the probe that have the potential to bind to those sites. For example, hybridization with unlabeled genomic DNA will render the high-copy repetitive sequences in the target genome double-stranded. Labeled copies of such sequences in the probe will not be able to bind when the probe is subsequently applied.

In practice, several mechanisms combine to produce the staining contrast. For example, when blocking DNA is added to the probe as in 3b above, that which remains single-stranded when the probe is applied to the target can bind to and block the target sequences. If the incubation of the probe with the blocking DNA is minimal, then the genomic DNA simultaneously blocks the probe and competes with the probe for binding sites in the target.

3e. Concept of Q. As mentioned in section 3b.i above, it is necessary to add the correct amount of genomic DNA to achieve the best compromise between inhibiting the hybridization capacity of high-copy repeats in the probe and reducing the desired signal intensity by inhibition of the binding of the target-specific sequences. The following discussion pertains to use of genomic blocking DNA with probes produced by cloning or otherwise replicating stretches of DNA from the target region of the genome. Thus, the probe contains a representative sampling of the single-copy, chromosome-specific repetitive sequences, and shared repetitive sequences found in the target. Such a probe might range in complexity from 100 kb of sequence derived from a small region of the genome, for example several closely spaced cosmid clones; to many millions of bases, for example a combination of multiple libraries from Table I. The discussion below is illustrative and can be extended to other situations where different blocking nucleic acids are used. The following discussion of Q is designed only to give general guidelines as to how to proceed.

The addition of unlabeled genomic DNA to a hybridization mix containing labeled probe sequences increases the concentration of all of the sequences, but increases the concentration of the shared sequences by a larger factor than the concentration of the target-specific sequences because the shared sequences are found elsewhere in the genome, whereas the target-specific sequences are not. Thus, the reassociation of the shared sequences is preferentially enhanced so that the hybridization of the labeled copies of the shared sequences to the target is preferentially inhibited.

To quantity this concept, first consider one of the sequences, repeat or single-copy, that hybridize specifically to the ith chromosome in a hybridization mixture containing a mass $m_p$ of probe DNA from the ith chromosome library of Table 1 (for example) and $m_b$ of unlabeled genomic DNA. The number of labeled copies of the sequence is proportional to $m_p$. However, the number of unlabeled copies is proportional to $f_i m_b$, where $f_i$ is the fraction of genomic DNA contained on the ith chromosome. Thus, the ratio of unlabeled to labeled copies of each of the sequences specific for the target chromosome, is $f_i m_b/m_p$, which is defined herein as Q. For normal human chromosomes, $0.016 \leq f_i \leq 0.08$ [Mendelsohn et al., *Science*, 179:1126 (1973)]. For representative examples described in Section VI.B (infra), $f_4=0.066$ and $f_{21}=0.016$. For a probe targeted at a region comprised of L base pairs, $f_i=L/G$ where G is the number of base pairs in a genome (approximately $3 \times 10^9$ bases for humans and other mammals). Thus, $Q=(L/G)(m_b/m_p)$.

Now consider a shared sequence that is distributed more-or-less uniformly over the genome, for example, Alu. The number of labeled copies is proportional to $m_p$, whereas the number of unlabeled copies is proportional to $m_b$. Thus, the ratio of unlabeled to labeled copies is $m_b/m_p=Q/f_i$. This is true for all uniformly distributed sequences, regardless of copy number. Thus adding genomic DNA increases the concentration of each specific sequence by the factor 1+Q, whereas each uniformly distributed sequence is increased by the larger factor $1+Q/f_i$. Thus, the reassociation rates of the shared sequences are increased by a larger factor than those of the specific sequences by the addition of genomic DNA.

It can be shown that roughly half of the beneficial effect of genomic DNA on relative reassociation rates is achieved when Q=1, and, by Q=5, there is essentially no more benefit to be gained by further increases. Thus, the protocol I hybridizations of Section VI.B infra keep $Q \leq 5$.

To illustrate the use of genomic blocking DNA, it is convenient to consider a model of a genome wherein 50% of the DNA is comprised of specific sequences (both repetitive and single-copy) and the other 50% of the DNA is comprised of shared repetitive sequences that are distributed uniformly over the genome. Thus, according to the model, if the target is L bases (that is, the probe contains fragments representing L bases of the target area or areas of the genome), sequences containing L/2 bases will be specific to the target, and L/2 will be shared with the entire genome.

Case I. The complexity of the probe is about 50 kb to about 100 kb. (In this case the complexity may be approximately equal to L since the probability is that no repetitive sequences will typically occur with more than a few copies in such a number of bases). Using a standard hybridization mixture (as exemplified in Section VI.B, infra), the target can be hybridized with about 2 ng of labeled probe DNA in 10 ul of hybridization mix, corresponding to approximately 1 pg/ul per kb of specific sequences (as used in Section VI.B, infra). Suppose the hybridization is to a slide containing $10^4$ cells (a typical number), and each cell has about 6 pg of DNA, (typical for mammals). Then in this model calculation, there is 3 pg of shared repetitive sequences per cell. Thus, for $10^4$ cells there are $3 \times 10^4$ pg or 30 ng of shared sequences on the slide. Similarly, there is $10^4 \times 0.5 \times 10^5 \times 6/3 \times 10^9$ pg=1 pg of target for the specific sequences. The probe contains ½×2 ng or 1 ng of shared sequences and 1 ng of specific sequences. Therefore, there is not enough probe to saturate the shared sequences in the target DNA, but enough to saturate the specific sequences. The signal from the shared sequences is spread at low intensity over the entire genome whereas the specific signal is concentrated in a compact region. Thus, good contrast can be obtained without adding any blocking genomic DNA at all.

A great deal of genomic DNA can be added to improve the contrast without interfering with the hybridization of the specific sequences, that is, Q remains low even if a great deal of genomic DNA is added.

$$Q = 10^5 / 3 \times 10^9 m_b / m_p = 3 \times 10^{-5} m_b / m_p.$$

If a large amount of blocking nucleic acid, for example, 10 ug were used (according to the standard hybridization protocols exemplified in Section VI.B infra wherein the practical limit of total nucleic acid is on the order of 10 ug in a 10 ul hybridization mixture) with the 2 ng of probe, then $Q = 3 \times 10^{-5} \times 10^4$ ng/2 ng=$3/2 \times 10^{-1}$=0.15. Thus, Q is <1, and is so low that the blocking DNA cannot substantially interfere with the desired signal. Increasing the amount of labeled probe nucleic acid to speed the hybridization would further decrease Q. In practice, one would typically use 1 ug of blocking DNA for such a hybridization.

Case II. As the size of the target region is increased, the complexity of the probe necessarily is increased, and the amount of DNA in the hybridization mix needs to be increased in order to have a sufficient concentration of each portion of specific sequence to hybridize. Also, if one desires to decrease the hybridization time of the procedure, the probe concentration must be increased. In these situations, the increase in probe concentration results in an increase in the amount of shared sequences in the hybridization mixture, which in turn increases the amount of hybridization that will occur to the shared sequences in the target area or areas, thereby reducing the contrast ratio.

With very high complexity probes spanning several entire chromosomes, L/G can approach 1. In order to stain such a portion of the genome within a reasonable time, for example, overnight, the concentration of labeled nucleic acid needs to be increased, for example, 200 ng in 10 ul of hybridization mixture. Up to about 3000 ng of blocking DNA can be used and still keep $Q \leq 5$ [wherein the calculation is Q=5=0.3 $m_b$/200 ng or $m_b$=1000 ng/0.3=3,333 ng]. In practice, staining 25% and more of the human genome (for example, human chromosomes 1, 3 and 4) can be accomplished with the blocking protocols described below, but the contrast is less than for that achieved with probes for smaller regions.

III. Labeling the Nucleic Acid Fragments of the Heterogeneous Mixture.

Several techniques are available for labeling single- and double-stranded nucleic acid fragments of the heterogeneous mixture. They include incorporation of radioactive labels, e.g. Harper et al. *Chromosoma,* Vol 83, pgs. 431–439 (1984); direct attachment of fluorochromes or enzymes, e.g. Smith et al., *Nucleic Acids Research,* Vol. 13, pgs. 2399–2412 (1985), and Connolly et al., *Nucleic Acids Research,* Vol. 13, pgs. 4485–4502 (1985); and various chemical modifications of the nucleic acid fragments that render them detectable immunochemically or by other affinity reactions, e.g. Tchen et al., "Chemically Modified Nucleic Acids as Immunodetectable Probes in Hybridization Experiments," *Proc. Natl. Acad. Sci.,* Vol 81, pgs. 3466–3470 (1984); Richardson et al., "Biotin and Fluorescent Labeling of RNA Using T4 RNA Ligase," *Nucleic Acids Research,* Vol. 11, pgs. 6167–6184 (1983); Langer et al., "Enzymatic Synthesis of Biotin-Labeled Polynucleotides: Novel Nucleic Acid Affinity Probes," *Proc. Natl. Acad. Sci.,* Vol. 78, pgs. 6633–6637 (1981); Brigati et al., "Detection of Viral Genomes in Cultured Cells and Paraffin-Embedded Tissue Sections Using Biotin-Labeled Hybridization Probes," *Virology,* Vol. 126, pgs. 32–50 (1983); Broker et al., "Electron Microscopic Visualization of tRNA Genes with Ferritin-Avidin: Biotin Labels," *Nucleic Acids Research,* Vol. 5, pgs. 363–384 (1978); Bayer et al., "The Use of the Avidin Biotin Complex as a Tool in Molecular Biology," *Methods of Biochemical Analysis,* Vol. 26, pgs. 1–45 (1980) Kuhlmann, *Immunoenzyme Techniques in Cytochemistry* (Weinheim, Basel, 1984). Langer-Safer et al., *PNAS USA,* 79: 4381 (1982): Landegent et al., *Exp. Cell Res.,* 153: 61 (1984); and Hopman et al., *Exp. Cell Res.,* 169: 357 (1987).

Exemplary labeling means include those wherein the probe fragments are biotinylated, modified with N-acetoxy-N-2-acetylaminofluorene, modified with fluorescein isothiocyanate, modified with mercury/TNP ligand, sulfonated, digoxigenenated or contain T-T dimers.

The key feature of "probe labeling" is that the probe bound to the target be detectable. In some cases, an intrinsic feature of the probe nucleic acid, rather than an added feature, can be exploited for this purpose. For example, antibodies that specifically recognize RNA/DNA duplexes have been demonstrated to have the ability to recognize probes made from RNA that are bound to DNA targets [Rudkin and Stollar, *Nature,* 265:472–473 (1977)]. The RNA used for such probes is unmodified. Probe nucleic acid fragments can be extended by adding "tails" of modified nucleotides or particular normal nucleotides. When a normal nucleotide tail is used, a second hybridization with nucleic acid complementary to the tail and containing fluorochromes, enzymes, radioactivity, modified bases, among other labeling means, allows detection of the bound probe. Such a system is commerically available from Enzo Biochem (Biobridge Labeling System; Enzo Biochem Inc., New York, N.Y.).

Another example of a means to visualize the bound probe wherein the nucleic acid sequences in the probe do not directly carry some modified constituent is the use of antibodies to thymidine dimers. Nakane et al., *ACTA HISTOCHEM. CYTOCHEM.,* 20 (2): 229 (1987), illustrate such a method wherein thymine-thymine dimerized DNA (T-T DNA) was used as a marker for in situ hybridization. The hybridized T-T DNA was detected immunohistochemically using rabbit anti-T-T DNA antibody.

All of the labeling techniques disclosed in the above references may be preferred under particular circumstances. Accordingly, the above-cited references are incorporated by reference. Further, any labeling techniques known to those in the art would be useful to label the staining compositions of this invention. Several factors govern the choice of labeling means, including the effect of the label on the rate of hybridization and binding of the nucleic acid fragments to the chromosomal DNA, the accessibility of the bound probe to labeling moieties applied after initial hybridization, the mutual compatibility of the labeling moieties, the nature and intensity of the signal generated by the label, the expense and ease in which the label is applied, and the like.

Several different high complexity probes, each labeled by a different method, can be used simultaneously. The binding of different probes can thereby be distinguished, for example, by different colors.

IV. In Situ Hybridization.

Application of the heterogeneous mixture of the invention to chromosomes is accomplished by standard in situ hybridization techniques. Several excellent guides to the technique are available, e.g., Gall and Pardue, "Nucleic Acid Hybridization in Cytological Preparations," *Methods in Enzymology,* Vol. 21, pgs. 470–480 (1981); Henderson, "Cytological Hybridization to Mammalian Chromosomes," *International Review of Cytology,* Vol. 76, pgs. 1–46 (1982); and Angerer, et al., "In Situ Hybridization to Cellular RNAs," in *Genetic Engineering: Principles and Methods,* Setlow and Hollaender, Eds., Vol. 7, pgs. 43–65 (Plenum Press, New York, 1985). Accordingly, these references are incorporated by references.

Three factors influence the staining sensitivity of the hybridization probes: (1) efficiency of hybridization (fraction of target DNA that can be hybridized by probe), (2) detection efficiency (i.e., the amount of visible signal that can be obtained from a given amount of hybridization probe), and (3) level of noise produced by nonspecific binding of probe or components of the detection system.

Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the heterogeneous mixture of probe to the DNA in the biological structure or tissue; (4) posthybridization washes to remove probe not bound in specific hybrids, and (5) detection of the hybridized probes of the heterogeneous mixture. The reagents used in each of these steps and their conditions of use vary depending on the particular situation.

The following comments are meant to serve as a guide for applying the general steps listed above. Some experimentation may be required to establish optimal staining conditions for particular applications.

In preparation for the hybridization, the probe, regardless of the method of its production, may be broken into fragments of the size appropriate to obtain the best intensity and specificity of hybridization. As a general guideline concerning the size of the fragments, one needs to recognize that if the fragments are too long they are not able to penetrate into the target for binding and instead form aggregates that contribute background noise to the hybridization; however, if the fragments are too short, the signal intensity is reduced.

Under the conditions of hybridization exemplified in Section VI.B wherein human genomic DNA is used as an agent to block the hybridization capacity of the high copy shared repetitive sequences, the preferred size range of the probe fragments is from about 200 bases to about 2000 bases, more preferably in the vicinity of 1 kb. When the size of the probe fragments is in about the 800 to about 1000 base range, the preferred hybridization temperature is about 30° C. to about 45° C., more preferably about 35° C. to about 40° C., and still more preferably about 37° C.; preferred washing temperature range is from about 40° C. to about 50° C., more preferably about 45° C.

The size of the probe fragments is checked before hybridization to the target; preferably the size of the fragments is monitored by electrophoresis, more preferably by denaturing agarose gel electrophoresis.

Fixatives include acid alcohol solutions, acid acetone solutions, Petrunkewitsch's reagent, and various aldehydes such as formaldehyde, paraformaldehyde, glutaraldehyde, or the like. Preferably, ethanol-acetic acid or methanol-acetic acid solutions in about 3:1 proportions are used to fix the chromosomes in metaphase spreads. For cells or chromosomes in suspension, a fixation procedure disclosed by Trask, et al., in *Science,* Vol. 230, pgs. 1401–1402 (1985), is useful. Accordingly, Trask et al., is incorporated by reference. Briefly, $K_2CO_3$ and dimethylsuberimidate (DMS) are added (from a 5x concentrated stock solution, mixed immediately before use) to a suspension containing about $5 \times 10^6$ nuclei/ml. Final $K_2CO_3$ and DMS concentrations are 20 mM and 3 mM, respectively. After 15 minutes at 25° C., the pH is adjusted from 10.0 to 8.0 by the addition of 50 microliters of 100 mM citric acid per milliliter of suspension. Nuclei are washed once by centrifugation (300 g, 10 minutes, 4° C. in 50 mM kCl, 5 mM Hepes buffer, at pH 9.0, and 10 mM $MgSO_4$).

A preferred fixation procedure for cells or nuclei in suspension is disclosed by Trask et al., *Hum. Genet.,* 78:251–259 (1988), which article is herein incorporated by reference. Briefly, nuclei are fixed for about 10 minutes at room temperature in 1% paraformaldehyde in PBS, 50 mM $MgSO_4$, pH 7.6 and washed twice. Nuclei are resuspended in isolation buffer (IB) (50 mM KCl, 5 mM HEPES, 10 mM $MgSO_4$, 3 mM dithioerythritol, 0.15 mg/ml RNase, pH 8.0)/0.05% Triton X-100 at $10^8$/ml.

Frequently before in situ hybridization chromosomes are treated with agents to remove proteins. Such agents include enzymes or mild acids. Pronase, pepsin or proteinase K are frequently used enzymes. A representative acid treatment is 0.02–0.2 N HCl, followed by high temperature (e.g., 70° C.) washes. Optimization of deproteinization requires a combination of protease concentration and digestion time that maximizes hybridization, but does not cause unacceptable loss of morphological detail. Optimum conditions vary according to tissue types and method of fixation. Additional fixation after protease treatment may be useful. Thus, for particular applications, some experimentation may be required to optimize protease treatment.

In some cases pretreatment with RNase may be desirable to remove residual RNA from the target. Such removal can be accomplished by incubation of the fixed chromosomes in 50–100 microgram/milliliter RNase in 2×SSC (where SSC is a solution of 0.15M NaCL and 0.015M sodium citrate) for a period of 1–2 hours at room temperature.

The step of hybridizing the probes of the heterogeneous probe mixture to the chromosomal DNA involves (1) denaturing the target DNA so that probes can gain access to complementary single-stranded regions, and (2) applying the heterogeneous mixture under conditions which allow the probes to anneal to complementary sites in the target. Methods for denaturation include incubation in the presence of high pH, low pH, high temperature, or organic solvents such as formamide, tetraalkylammonium halides, or the like, at various combinations of concentration and temperature. Single-stranded DNA in the target can also be produced with enzymes, such as, Exonuclease III [van Dekken et al., *Chromosoma* (Berl) 97:1–5 (1988)]. The preferred denaturing procedure is incubation for between about 1–10 minutes in formamide at a concentration between about 35–95 percent in 2×SSC and at a temperature between about 25–70° C. Determination of the optimal incubation time, concentration, and temperature within these ranges depends on several variables, including the method of fixation and type of probe nucleic acid (for example, DNA or RNA).

After the chromosomal DNA is denatured, the denaturing agents are typically removed before application of the heterogeneous probe mixture. Where formamide and heat are the primary denaturing agents, removal is conveniently accomplished by several washes with a solvent, which solvent is frequently chilled, such as a 70%, 85%, 100% cold ethanol series. Alternatively the composition of the denaturant can be adjusted as appropriate for the in situ hybridization by addition of other consitutents or washes in appropriate solutions. The probe and target nucleic acid may be denatured simultaneously by applying the hybridization mixture and then heating to the appropriate temperature.

The ambient physiochemical conditions of the chromosomal DNA and probe during the time the heterogeneous mixture is applied is referred to herein as the hybridization conditions, or annealing conditions. Optimal hybridization conditions for particular applications can be adjusted by controlling several factors, including concentration of the constituents, incubation time of chromosomes in the heterogeneous mixture, and the concentrations, complexities, and lengths of the nucleic acid fragments making up the heterogeneous mixture. Roughly, the hybridization conditions must be sufficiently close to the melting temperature to minimize nonspecific binding. On the other hand, the conditions cannot be so stringent as to reduce correct hybridizations of complementary sequences below detectable levels or to require excessively long incubation times.

The concentrations of nucleic acid in the hybridization mixture is an important variable. The concentrations must be high enough so that sufficient hybridization of respective chromosomal binding sites occurs in a reasonable time (e.g., within hours to several days). Higher concentrations than that necessary to achieve adequate signals should be avoided so that nonspecific binding is minimized. An important practical constraint on the concentration of nucleic acid in the probe in the heterogeneous mixture is solubility. Upper bounds exist with respect to the fragment concentration, i.e., unit length of nucleic acid per unit volume, that can be maintained in solution and hybridize effectively.

In the representational examples described in Section VI.B (infra), the total DNA concentration in the hybridization mixture had an upper limit on the order of 1 ug/ul. Probe concentrations in the range of 1–20 ng/ul were used for such whole chromosome staining. The amount of genomic blocking DNA was adjusted such that Q was less than 5. At the low end of probe concentration, adequate signals were obtained with a one hour incubation, that is, a time period wherein the probe and blocking DNA are maintained together before application to the targeted material, to block the high-copy sequences and a 16 hour hybridization. Signals were visible after two hours of hybridization. The best results (bright signals with highest contrast) occurred after a 100 hour hybridization, which gave the low-copy target-specific sequences more opportunity to find binding sites. At the high end of the probe concentration, bright signals are obtained after hybridizations of 16 hours or less; the contrast was reduced since more labeled repetitive sequences were included in the probe.

The fixed target object can be treated in several ways either during or after the hybridization step to reduce nonspecific binding of probe DNA. Such treatments include adding nonprobe, or "carrier", DNA to the heterogeneous mixture, using coating solutions, such as Denhardt's solution (*Biochem. Biophys. Res. Commun.*, Vol. 23, pgs. 641–645 (1966), with the heterogeneous mixture, incubating for several minutes, e.g., 5–20, in denaturing solvents at a temperature 5–10° C. above the hybridization temperature, and in the case of RNA probes, mild treatment with single strand RNase (e.g., 5–10 micrograms per millileter RNase) in 2×SSC at room temperature for 1 hour).

V. Chromosome-Specific Staining Reagents Comprising Selected Single-Copy Sequences V.A. Making and Using a Staining Reagent Specific to Human Chromosome 21

V.A.1. Isolation of Chromosome 21 and Construction of a Chromosome 21-Specific Library DNA fragments from human chromosome-specific libraries are available from the National Laboratory Gene Library Project through the American Type Culture Collection (ATCC), Rockville, Md. DNA fragments from chromosome 21 were generated by the procedure described by Fuscoe et al., in "Construction of Fifteen Human Chromosome-Specific DNA Libraries from Flow-Purified Chromosomes," *Cytogenet. Cell Genet.*, Vol. 43, pgs. 79–86 (1986), which reference is incorporated by reference. Briefly, a human diploid fibroblast culture was established from newborn foreskin tissue. Chromosomes of the cells were isolated by the $MgSO_4$ method of van den Engh et al., *Cytometery*, Vol. 5, pgs. 108–123 (1984), and stained with the fluorescent dyes—Hoechst 33258 and Chromomycin A3. Chromsome 21 was purified on the Lawrence Livermore National Laboratory high speed sorter, described by Peters et al., *Cytometry*, Vol. 6, pgs. 290–301 (1985).

After sorting, chromosome concentrations were approximately $4 \times 10^5$/ml. Therefore, prior to DNA extraction, the chromosomes ($0.2$–$1.0 \times 10^6$) were concentrated by centrifugation at 40,000×g for 30 minutes at 4° C. The pellet was then resuspended in 100 microliters of DNA isolation buffer (15 mM NaCl, 10 mM EDTA, 10 mM Tris HCl pH 8.0) containing 0.5% SDS and 100 micrograms/ml proteinase K. After overnight incubation at 37° C., the proteins were extracted twice with phenol:chloroform:isoamyl alcohol (25:24:1) and once with chloroform:isoamyl alcohol (24:1). Because of the small amounts of DNA, each organic phase was reextracted with a small amount of 10 mM Tris pH 8.0, 1 mM EDTA (TE). Aqueous layers were combined and transferred to a Schleicher and Schuell mini-collodion membrane (#UHO20/25) and dialyzed at room temperature against TE for 6–8 hours. The purified DNA solution was then digested with 50 units of Hind III (Bethesda Research Laboratories, Inc.) in 50 mM NaCl, 10 mM Tris HCl pH 7.5, 10 mM $MgCl_2$, 1 mM dithiothreitol. After 4 hours at 37°, the reaction was stopped by extractions with phenol and chloroform as described above. The aqueous phase was dialyzed against water overnight at 4° C. in a mini-collodion bag and then 2 micrograms of Charon 21A arms cleaved with Hind III and treated with calf alkaline phosphatase (Boehringer Mannheim) were added. This solution was concentrated under vacuum to a volume of 50–100 microliters and transferred to a 0.5 ml microfuge tube where the DNA was precipitated with one-tenth volume 3M sodium acetate pH 5.0 and 2 volumes ethanol. The precipitate was collected by centrifugation, washed with cold 70% ethanol, and dissolved in 10 microliters of TE.

After allowing several hours for the DNA to dissolve, 1 microliter of 10× ligase buffer (0.5M Tris HCl pH 7.4, 0.1 M $MgCl_2$, 0.1M dithiothreitol, 10 mM ATP, 1 mg/ml bovine serum albumin) and 1 unit of T4 ligase (Bethesda Research Laboratory, Inc.) were added. The ligation reaction was incubated at 10° C. for 16–20 hours and 3 microliter aliquots were packaged into phage particles using in vitro extracts prepared from *E. coli* strains BHB 2688 and BHB 2690, described by Hohn in *Methods in Enzymology,* Vol. 68, pgs. 299–309 (1979) *Molecular Cloning: A Laboratory Manual,* (Cold Spring Harbor Laboratory, New York, 1982). Briefly, both extracts were prepared by sonication and combined at the time of in vivo packaging. These extracts packaged wild-type lambda DNA at an efficiency of $1-5 \times 10^8$ plaque forming units (pfu) per microgram. The resultant phage were amplified on *E. coli* LE392 at a density of approximately $10^4$ pfu/150 mm dish for 8 hours to prevent plaques from growing together and to minimize differences in growth rates of different recombinants. The phage were eluted from the agar in 10 ml SM buffer (50 mM Tris HCl pH 7.5, 10 mM $MgSO_4$, 100 mM NaCl, 0.01% gelatin) per plate by gentle shaking at 4° C. for 12 hours. The plates were then rinsed with an additional 4 ml of SM. After pelleting cellular debris, the phage suspension was stored over chloroform at 4° C.

V.A.2. Construction and Use of Chromosome 21-Specific Stain for Staining Chromosome 21 of Human Lymphocytes Clones having unique sequence inserts are isolated by the method of Benton and Davis, *Science,* Vol. 196, pgs. 180–182 (1977). Briefly, about 1000 recombinant phage are isolated at random from the chromosome 21-specific library. These are transferred to nitrocellulose and probed with nick translated total genomic human DNA.

Of the clones which do not show strong hybridization, approximately 300 are picked which contain apparent unique sequence DNA. After the selected clones are amplified, the chromosome 21 insert in each clone is $^{32}P$ labeled and hybridized to Southern blots of human genomic DNA digested with the same enzyme used to construct the chromosome 21 library, i.e., Hind III. Unique sequence containing clones are recognized as those that produce a single band during Southern analysis. Roughly, 100 such clones are selected for the heterogeneous mixture. The unique sequence clones are amplified, the inserts are removed by Hind III digestions, and the inserts are separated from the phage arms by gel electrophoresis. The probe DNA fragments (i.e., the unique sequence inserts) are removed from the gel and biotinylated by nick translation (e.g., by a kit available from Bethesda Research Laboratories). Labeled DNA fragments are separated from the nick translation reaction using small spin columns made in 0.5 ml Eppendorph tubes filled with Sephadex G-50 (medium) swollen in 50 mM Tris, 1 mM EDTA, 0.1% SDS, at pH 7.5. Human lymphocyte chromosomes are prepared following Harper et al, *Proc. Natl. Acad. Sci.,* Vol. 78, pgs. 4458–4460 (1981). Metaphase and interphase cells were washed 3 times in phosphate buffered saline, fixed in methanol-acetic acid (3:1) and dropped onto cleaned microscope slides. Slides are stored in a nitrogen atmosphere at −20° C.

Slides carrying interphase cells and/or metaphase spreads are removed from the nitrogen, heated to 65° C. for 4 hours in air, treated with RNase (100 micrograms/ml for 1 hour at 37° C.), and dehydrated in an ethanol series. They are then treated with proteinase K (60 ng/ml at 37° C. for 7.5 minutes) and dehydrated. The proteinase K concentration is adjusted depending on the cell type and enzyme lot so that almost no phase microscopic image of the chromosomes remains on the dry slide. The hybridization mix consists of (final concentrations) 50 percent formamide, 2×SSC, 10 percent dextran sulfate, 500 micrograms/ml carrier DNA (sonicated herring sperm DNA), and 2.0 microgram/ml biotin-labeled chromsome 21-specific DNA. This mixture is applied to the slides at a density of 3 microliters/$cm^2$ under a glass coverslip and sealed with rubber cement. After overnight incubation at 37° C., the slides are washed at 45° C. (50% formamide-2×SSC pH 7, 3 times 3 minutes; followed by 2×SSC pH 7, 5 times 2 minutes) and immersed in BN buffer (0.1 M Na bicarbonate, 0.05 percent NP-40, pH 8). The slides are never allowed to dry after this point.

The slides are removed from the BN buffer and blocked for 5 minutes at room temperature with BN buffer containing 5% non-fat dry milk (Carnation) and 0.02% Na Azide (5 microliter/$cm^2$ under plastic coverslips). The coverslips are removed, and excess liquid briefly drained and fluorescein-avidin DCS (3 microgram/ml in BN buffer with 5% milk and 0.02% NaAzide) is applied (5 microliter/$cm^2$). The same coverslips are replaced and the slides incubated 20 minutes at 37° C. The slides are then washed 3 times for 2 minutes each in BN buffer at 45° C. The intensity of biotin-linked fluorescence is amplified by adding a layer of biotinylated goat anti-avidin antibody (5 microgram/ml in BN buffer with 5% goat serum and 0.02% Na Azide), followed, after washing as above, by another layer of fluorescein-avidin DCS. Fluorescein-avidin DCS, goat antiavidin and goat serum are all available commercially, e.g., Vector Laboratories (Burlingame, Calif.). After washing in BN, a fluorescence antifade solution, p-phenylenediamine (1.5 microliter/$cm^2$ of coverslip) is added before observation. It is important to keep this layer thin for optimum microscopic imaging. This antifade significantly reduced fluorescein fading and allows continuous microscopic observation for up to 5 minutes. The DNA counterstains (DAPI or propidium iodide) are included in the antifade at 0.25–0.5 microgram/ml.

The red-fluorescing DNA-specific dye propidium iodide (PI) is used to allow simultaneous observation of hybridized probe and total DNA. The fluorescein and PI are excited at 450–490 nm (Zeiss filter combination 487709). Increasing the excitation wavelength to 546 nm (Zeiss filter combination 487715) allows observation of the PI only. DAPI, a blue fluorescent DNA-specific stain excited in the ultraviolet (Zeiss filter combination 487701), is used as the counterstain when biotin-labeled and total DNA are observed separately. Metaphase chromosome 21s are detected by randomly located spots of yellow distributed over the body of the chromosome.

V.B. Improved Method for Efficiently Selecting Chromosome 21 Single-Copy Sequences Fuscoe et al., *Genomics,* 5:100–109 (1989) provides more efficient procedures than the method described immediately above (V.A.2) for selecting large numbers of single-copy sequence or very low copy number repeat sequence clones from recombinant phage libraries and demonstrates their use to stain chromosome 21. Said article is hereby incorporated by reference. Briefly, clones were selected from the Charon 21A library LL21NS02 (made from DNA from human chromosome 21) using two basic procedures. In the first, the phage library was screened in two stages using methods designed to be more sensitive to the presence of repetitive sequences in the clones than the method of Section V.A.2. The selected clones were then subcloned into plasmids. The 450 inserts thus selected form the library pBS-U21. The second was in a multistep process in which: 1) Inserts from LL21NS02 were subcloned into Bluescribe plasmids, 2) plasmids were grown at high density in bacterial colonies on nitrocellulose filters and 3) radioactive human genomic DNA was hybridized to the plasmid DNA on nitrocellulose filters at low stringency in two steps and 4) plasmids having inserts that failed to hybridize were selected as potentially carrying single-copy sequences. Fifteen hundred and thirty colonies were picked in this manner to form the library pBS-U21/1530.

Southern analysis indicated that the second procedure was more effective at recognizing repetitive sequence than the first. Fluorescence in situ hybridization with DNA from pBS-U21/1530 allowed specific, intense staining of the number 21 chromosomes in metaphase spreads made from human lymphocytes. Hybridization with pBS-U21 gives less specific staining of chromosome 21. Details concerning the Fuscoe et al. method of selecting single-copy sequence or very low repeat sequence probes from recombinant libraries follow immediately below.

V.B.1. Phage Screening

Charon 21A phage from the LL21NS02 library were plated onto 30 plates at an average density of 86 pfu per plate. DNA from each plate was transferred onto HATF085-50 nitrocellulose filters (Benton and Davis, supra) by blotting. Duplicate plaque lifts were prepared from each plate. One set of filters was hybridized with an oligonucleotide that spans the cloning site in Charon 21A (Fuscoe, *Gene*, 52:291, 1987). Hybridization occurs when the Hind III cloning site is not interrupted by an insert. The other set was subjected to the primary phage screen for human repetitive sequences. Phage that were negative in both hybridizations (indicating that the phage were recombinant and the amount of repetitive DNA was below the limit of detection) were picked into individual wells of microtiter dishes. To assist with the identification of the appropriate plaques, the agar plates were photographed onto transparencies at 1:1 magnification. These were overlaid on the autoradiographs. The selected phage were then screened again using the same procedure.

Primary Phage Screen For Repetitive Sequences: Phage clones containing repetitive DNA sequences were identified by hybridization with $^{32}$P-labeled human lymphocyte DNA. The DNA was $^{32}$P labeled by nick translation [Rigby et al., *J. Mol. Biol.*, 113:237 (1977)] to a specific activity of >$10^8$ cpm/ug. Plaque lifts were prepared as above. They were prehybridized in buffer B (50 ml of 50% formamide, 5×SSC, 5×Denhart's and 250 ug/ml sonicated, denatured herring sperm DNA) at 42° C. for 3 hours and hybridized in 50 ml of buffer B containing 3×$10^6$ cpms of probe per ml at 42° C. overnight. The filters were washed once at room temperature in 2×SSC, 5× Denhart's, and 0.1% SDS for 10 minutes, twice in the same buffer at 65° C. for 30 minutes each and finally rinsed twice in 0.1×SSC at room temperature. After air drying, the filters were exposed to x-ray film (Kodak X-AR5) with an intensifier screen for 48 hours at 80° C.

Secondary Phage Screen for Repetitive Sequences: Recombinant plaques giving no hybridization signal with the oligonucleotide or the genomic DNA were picked into individual wells of 96 well microtiter plates containing 50 ul of SM (100 mM NaCl, 8 mM MgSO$_4$, 50 mM Tris HCl pH 7.5, 0.1% gelatin) and the phage were allowed to diffuse overnight. Five microliters of each phage isolate were transferred to a conical bottom microtiter tray well and combined with 5 ul of a 1:5 dilution of stationary phase *E. coli* LE392, prepared by incubation overnight at 37° C. with good aeration in L-broth containing 0.2% maltose and 10 mM MgSO$_4$. Infection was performed at 37° C. for 15 minutes with no shaking. Six microliters of each infection were spotted onto a nitrocellulose filter (Millipore HATF 085 150) that had been soaked in a 1:5 dilution of an overnight culture of LE392, described above. The filters were hybridized and screened under the conditions of the primary screen following plaque formation at 37° C. Again, plaques showing no hybridization signal were picked for subsequent evaluation.

V.B.2. Subcloning From Charon 21A Phage Into Plasmids

Inserts were subcloned in bulk from Charon 21A into Bluescribe plasmids (Stratagene). Bluescribe is a 2.75 kb, pUC19-derived, high copy number vector which permits selection on ampicillin and the chromogenic indicator Xgal. Run-off RNA transcripts can be made from T3 and T7 promoters that flank the lacZ gene and the cloning site. Charon 21A recombinant phage and Bluescribe plasmid DNAs were digested to completion with Hind III. The Bluescribe DNA was then dephosphorylated with calf intenstine alkaline phosphatase (Boehringer Mannheim). Four hundred ng of Bluescribe vector was ligated to 5 ug of Hind III-cleaved phage DNA with 1 unit ligase [Bethesda Research Laboratories (BRL)] in 10 ul at 15° C. overnight. *E. coli* JM83 or DH5alpha (BRL) cells were transformed with 1 ul of the ligation reaction by the method of Dagert and Ehrlich, *Gene*, 6:23 (1979). The transformed cells were plated onto L-plates containing 100 ug/ml ampicillin (L-amp 100) and 40 ug/ml X-gal (BRL) and incubated overnight at 37° C. Recombinants formed pale blue-white colonies and grew larger than the deep blue nonrecombinants. The recombinants were picked into individual wells of 96 well microtiter dishes filled with L-Amp-100. After overnight growth, glycerol was added to a final concentration of 15%, and the cells were frozen at −80° C.

V.B.3 Plasmid Colony Screening For Repetitive Sequences.

Primary Plasmid Screen For Repetitive Sequences: A microtiter dish inoculating block consisting of 96 machine screws arranged in the 8×12 pattern of the wells in a 96 well microtiter dish was used to transfer bacteria containing recombinant plasmids to a nitrocellulose filter. The filter was overlayed on an L-amp 100 plate and 96 bacterial-plasmid colonies were grown overnight. The colonies on each filter were sufficiently well separated that the overlap between plasmid DNAs from adjacent colonies was minimal. The filters were prepared for hybridization as described by Weber et al, *Mol. Cell Biol.*, 8:1137 (1987). Briefly the bacteria were lysed with 10% SDS, and the DNA was denatured (0.5M NaOH, 1.5M NaCl) and fixed (1M NH$_4$OAc, 0.02 M NaOH). Bacterial debris was removed by washing in 2×SSC. The filters were prehybridized and hybridized with $^{32}$P-labeled human genomic DNA at 1×$10^6$ cpm/ml as in phage screening except that the hybridization temperature was 34° C.

Secondary Plasmid Hybridizations Screen For Repetitive Sequences: Colonies negative on the first screen were picked into fresh microtiter dishes as described above. New filters were prepared and were rehybridized as in the primary screen except that the probe concentration was increased to 3×$10^6$ cpm/ml. Colonies negative on this screen were picked into new microtiter dishes.

V.B.4 Plasmid Copy Number Quantitation

Twelve clones were picked at random from the pBS-U21 library and used to inoculate a 96-well microtiter dish (100 ul L-broth plus 100 ug/ml ampicillin per well). There were 8 identical rows of the 12 individual clones. These were grown overnight at 37° C. One column of 8 cultures, did not grow. All of the 88 colonies that grew were of approximately the same size. The inoculating block was used to replicate the bacterial array onto 2 nitrocellulose filters overlaying L-amp 100 plates. The bacteria on these filters were then incubated for 20 hours, one at 37° C. and one at 32° C. Each filter was then cut in half (40 or 48 colonies). One half of each filter was placed into 10 ml L-broth containing 100 ug/ml ampicillin. The bacteria were eluted together by vortexing and stored at 4° C. The other half of each filter was transferred to L-agar plates containing 100 ug/ml chloramphenicol and incubated 24 hours at 37° C. These filters were then placed in 10 ml L-broth containing 100 ug/ml ampicillin, and the bacteria were eluted and stored. The optical density of the eluted bacteria (determined at 650 nm) ranged between 3.6 and 5.3. The number of colony forming units (cfu) per filter was determined by plating dilutions onto L-amp 100 plates. Finally, plasmid DNA was isolated from 1.5 ml of the eluted bacteria from each filter by the alkaline extraction method [Birnboim and Doly, *Nucl. Acids Res.*, 7:1513 (1979)]. The amount of isolated DNA was measured in two ways: 1) Test and known amounts of standard DNA were separated using agarose gel electrophoresis. The gels were then stained with ethidium bromide and the amount of test DNA was determined by comparison with the standard. 2) The isolated DNA was stained with Hoechst 33258 and the fluorescence intensity (proportional to DNA amount) was measured fluorimetrically.

V.B.5. Southern Hybridization

Southern blot hybridizations were performed using standard procedures [Maniatis et al., *Molecular Cloning: A Laboratory Manual* (Cold Spring Harbor Laboratory 1982)]. Briefly, 5 ug or 10 ug of genomic DNA from cells in a mapping panel was digested to completion with Hind III and size fractionated on 0.8% agarose minigels. Alternatively, the DNA was prepared from cells encapsulated in agarose. Approximately $10^6$ cells (~6 ug) were mixed with 30 ul of low gelling temperature agarose (Sea Plaque, FMC). The final agarose concentration was 0.5%. After cooling, the plugs were incubated at 50° C. in 0.5 M EDTA pH 8.0, 1% sarcosine, 2 mg/ml proteinase K for 40 hr. They could then be stored at least 1 year at 4° C. The plugs were rinsed in 10 volumes 10 mM Tris pH 7.5, 0.1 mM EDTA containing 1 mM phenylmethylsulfonyl fluoride (PMSF) three times for 20 min each at room temperature and in this buffer without PMSF twice for 30 min each. The plugs were transferred to 1× medium salt butter Maniatis et al., supra) containing 200 units Hind III and 300 ug/ml bovine serum albumin and incubated 3 hr at 37° C. After melting at 65° C. for 3 min, the DNA-agarose mixture was placed into wells of agarose gels for electrophoresis. The size fractionated DNA was transferred to nitrocellulose and probed with plasmids nick translated to $10^8$ cpm/ug with $^{32}$P. Hybridization was in 50% formamide, 5×SSC at 42 C.

V.B.6. Fluorescence in Situ Hybridization

Biotin labeling of the probe, metaphase spread preparation, and hybridization were as described by Pinkel et al. (I), supra. Briefly DNA samples from the chromosome 21 probe collections pBS-U21 and pBS-U21/1530 (including plasmid DNA) were biotin labeled by nick translation (BRL), and used at a concentration of 4 ug/ml in hybridization mix containing 50% formamide, 2×SSC, 10% dextran sulfate, and 1 mg/ml carrier DNA (herring). The metaphase spreads were treated with RNAse (100 ug/ml in 2×SSC) at 37° C. for 1 hour, heated (70° C. in 70% formamide, 2×SSC for 2 minutes) to denature the target DNA, and dehydrated in ethanol. The hybridization mix was heated to 70° C. for 5 minutes to denature the probe, applied to the slide in a 37° C. glove box, and sealed under a glass coverslip. The slide was incubated at 37° C. overnight. After incubation, the cover slip was removed and the slide was washed twice in 50% formamide, 2×SSC at 45° C. for 2 minutes, and once in 0.1 M phosphate buffer (pH 8) containing 0.1% NP40 (PN buffer) for 2 minutes. Fluorescent staining of the hybridized probe was accomplished by alternately incubating with fluorescein-avidin DCS and biotinylated anti-avidin antibody (Vector Laboratories, Burlingame, Calif.), both at 5 ug/ml in PN buffer plus 5% nonfat dry milk, until three layers of avidin were applied. These incubations were 20 minutes in duration at room temperature. Slides were washed in PN between layers. The slides were counterstained with propidium iodide (1 ug/ml) in a fluorescence anti-fade solution [Johnson and Arovjo, *J. Immunol.* Methods, 43:349 350, (1981)].

V.B.7 Library pBS-U21

Phage Screening: Two thousand five hundred phage plaques were screened twice to identify recombinant phage carrying unique-sequence inserts. In the first screen, 850 out of 2500 plaques were found to be non-recombinant, and 524 recombinants had undetectable levels of human repetitive sequences. After the second screen, 450 recombinant phage remained negative. Inserts from these phage were subcloned in bulk into Bluescribe plasmids. Eight hundred and forty recombinant plasmids were selected to form the library designated pBS-U21.

pBS-U21 Characterization: Plasmid DNA samples from 48 random clones from pBS-U21 were prepared (Birnboin and Doly, supra) and the plasmid inserts were sized on agarose gels. Forty-four clones contained single Hind III fragments, three clones contained 2 Hind III fragments and one clone contained 3 Hind III fragments. The sizes ranged from 4.8 kb to <0.1 kb with the average being 2.0 kb. Seventy percent of the clones contained inserts of greater than 0.5 kb. Some plasmid clones contained Hind III inserts of nearly identical size. To determine if the inserts in these clones were identical, DNA from each clone was cleaved with the 4-cutter Sau3A which should cut the insert into multiple pieces of average size about 250 bases. Agarose gel electrophoresis of these fragments suggested that 4 pairs of identical clones were present in the 48 tested.

The frequency of unique and repeat-sequences in pBS-U21 was estimated by hybridizing radiolabeled DNA from 18 of the 48 clones against Southern blots of HindIII digested human DNA. Clones producing a single band of the predicted size and intensity on an autoradiograph of the blot were scored as carrying a unique-sequence insert. Clones producing multiple bands or smears were scored as carrying repetitive inserts.

The average size of the 18 inserts was 2.9 kb. Eleven clones hybridized to unique single Hind III fragments in the human DNA of the same size as the cloned insert. The remaining 7 showed the presence of repetitive sequences. Thus about 60% (11/18) clones in pBS-U21 proved to carry unique sequence inserts.

Detection of Residual Repetitive Sequences in pBS-U21 by Plasmid Colony Screening: The 48 plasmid clones from pBS-U21 described above were rescreened by plasmid colony screening. Sixteen were found to be repetitive. Eighteen of the 48 clones were those characterized by Southern analysis as described above. One third of these (7/18) were shown to contain repetitive sequences by Southern analysis. Plasmid colony screening detected 5 of the 7 repeats. Thus only about 10% (2/18 ) of the clones that passed the plasmid colony screen contained repetitive sequences.

Sensitivity of Plasmid Colony Screening: The sensitivity of the plasmid colony screen is due, at least in part, to the large amount and high density of human DNA in the plasmid colonies. Colonies grown overnight at 37° C. (the condition used for colony production in the colony screening assay) contained about $6\times10^8$ bacteria/colony and about 2.6 ug plasmid DNA per colony. This would suggest that each bacteria contained about 1000 plasmids if each plasmid was about 5 kb in size. This is in the range expected for the pUC series of plasmids. The bacterial growth conditions can affect the plasmid density significantly. For example, bacteria grown at 32° C. contain about 5 times fewer plasmids. The plasmid DNA density can be increased by treatment with chloramphenicol although this was not used for colony production in this example. The most plasmid DNA per colony was obtained by 20 hr growth at 37° C. followed by 24 hr growth on chloramphenicol at 37° C.

V.B.8. Library pBS-U21/1530:

Plasmid Selection: Inserts from the entire LL21NS02 library were subcloned into Bluescribe. Ten thousand seven hundred and fifty two recombinants were individually picked into the wells of microtiter plates. Half of these were subjected to the primary plasmid colony screen. The negative clones (2450) were transferred to a new set of plates and subjected to the secondary plasmid colony screen as described above. The negative clones (1530) were transferred to a new set of plates and are being maintained individually. The collection of such clones form the library pBS-U21/1530.

pBS-U21/1530 Characterization: Plasmid DNA samples from 46 random clones from pBS-U21/1530 were prepared (Birnboim and Doly, supra), and the plasmid inserts were sized on agarose gels. Forty-four of these clones contained a single insert while two contained 2 inserts. The inserts ranged from 4 kb to <0.25 kb. The average insert size was 0.9 kb. Half of the inserts were larger than 0.25 kb.

DNA samples from 13 of the 46 random clones were characterized by Southern analysis using Hind III digested DNA from human cells as described above. These 13 clones carried 14 inserts. About 80% of the clones (10/13) proved to be unique sequence.

V.B.9 In Situ Hybridization with pBS-U21 and pBS U21/1530

Both pBS-U21 and pBS-U21/1530 preferentially and distinctly stained the number 21 chromosome. The pBS-U21 library showed preferential hybridization to both copies of chromosome 21, but there was substantial hybridization to other chromosomes. The hybridization of pBS-U21/1530 was more specific. The hybridization was weak on the short arm of the chromosome where the repetitive ribosomal sequences reside; the intensity of the signal was concentrated in the middle of the long arm of chromosome 21. Many interphase nuclei showed distinct labeling of two apparent chromosome 21 domains. The fact that the pBS-U21 library contained more repeat-sequence inserts that might hybridize non specifically than did the pBS-U21/1530 library may account for the higher specificity of the pBS-21/1530 hybridization.

V.B.10 Conclusion

Demonstrated in this subsection is that bulk subcloning of the human chromosome 21 library LL21NS02 into plasmids, followed by colony hybridization with radiolabeled human genomic DNA, allows efficient selection of a library in which 80 to 90% of the clones contain only unique sequences. Also shown is that DNA from clones selected by this procedure can be used in fluorescence in situ hybridization to specifically stain the number 21 chromosomes in human metaphase spreads and interphase nuclei. The intensity of staining of the unique sequence probes is not as high as that obtained using highly repeated DNA sequences as probes [Pinkel et al. (I), supra] because the amount of target sequence for the unique sequence probes is relatively low and is spread out over an extended region. The amount of target sequence for a highly repeated probe may be around 5 Mb; whereas the amount of target sequence for the DNA probes isolated from the pBS-U21 and pBS-U21/1530 libraries are only about 0.9 Mb and 1.3 Mb, respectively. In addition, the high complexity of the probes means that each element is present at low concentration during the hybridization. The nonspecific hybridization with DNA from pBS-U21/1530 may be due to the remaining low level repeats or to unique sequences that are not from chromosome 21. Some non-specific hybridization may also result from the binding of labeled plasmid sequences.

The LL21NS02 library appears to be highly chromosome-specific in that about 80% of the clones from pBS-U21 and 70% of the clones from pBS-U21/1530 map to chromosome 21.

Further concluded herein was that in a comparison of the ability of phage plaque screening and plasmid colony screening to remove clones containing repetitive DNA, the plasmid colony screen was significantly more sensitive than the phage plaque screen. The higher sensitivity of the plasmid colony screen resulted from the high density of human DNA in the plasmids of a colony. The human DNA content of the plasmid colony was calculated to be about $5\times10^4$ times that of a plaque, whereas the human DNA density of a plasmid colony was about $4\times10^3$ times that of a plaque.

These experiments indicated that bulk subcloning of lambda phage libraries into plasmids followed by plasmid colony screening as described above should result in selection of a plasmid library in which approximately 90% of the plasmids carry unique-sequence inserts. Some technical improvement in the colony screening procedure, such as the use of chloramphenicol to increase the plasmid content of the bacteria, may make it possible to obtain a positive hybridization signal from essentially every colony, thus improving sensitivity. Using control colonies with well characterized inserts, it should be possible to choose upper and lower intensity thresholds that would optimize selection of unknown clones containing inserts with the desired characteristics.

V.C. Hybridization with a Collection of Chromosome 4 Single-Copy Sequences

Chromosome 4 Single-Copy Sequences. One hundred and twenty clones carrying chromosome 4-specific single-copy sequence inserts selected from the Charon 21A library LL04NS01 (ATCC accession number 57700; Van Dilla et al., supra; see Table 1) were supplied by C. Gilliam (Harvard University) [Gilliam et al., *Nucleic Acids Res.*, 15:1445 (1987)]. The human inserts were all about 3 kilobases (kb) in length, so the ratio of insert to vector DNA was <0.1. Total phage DNA was produced from each clone individually using DEAE-cellulose columns (Whatman DE-52) [Helms et al., *DNA*, 4:39 (1985)]. DNA pooled from the 120 clones was biotinylated by nick-translation with biotin-11-dUTP (Bethesda Research Laboratories) and recovered at a concentration of about 20 nanograms per microliter (ng/ul) using Sephadex G-50 spin columns.

Cells. Metaphase spreads from human lymphocytes were prepared from methotrexate-synchronized cultures by using the procedure of Harper et al., supra. The cells were fixed in methanol/acetic acid, 3:1. Slides were stored at −20° C. in plastic bags filled with nitrogen gas.

In Situ Hybridization: Single-Copy Hybridization. Hybridization was accomplished by using a modification of the procedure described by Pinkel et al., *PNAS USA*, 83: 2934 (1986). The slide mounted cells were treated with RNase [100 micrograms per milliliter (ug/ml) in 0.3 molar (M) sodium chloride (NaCl)/30 millimolar (mM) sodium citrate at 37° C. for 1 hr), dehydrated in a 70%/85%/100% ethanol series, treated with proteinase K (0.3–0.6 ug/ml in 20 mM Tris/2 mM $CaCl_2$, pH 7.5, for 7.5 min at 37° C.), and fixed [4% paraformaldehyde in phosphate-buffered saline (PBS; in g/liter, KCl, 0.2; $KH_2PO_4$, 0.2; NaCl, 8; $Na_2HPO_4.7H_2O$, 2.16) plus 50 mM $MgCl_2$ for 10 min at room temperature]. The DNA in the target cells was denatured by immersion in 70% formamide/2×SSC (0.3 M NaCl/30 mM sodium citrate) at pH 7, for 2 min at 70° C. The hybridization mixture [10 ul total volume consisting of 50% formamide, 0.3 M NaCl/30 mM sodium citrate (final concentration), 10% dextran sulfate, 50 ug of sonicated herring DNA per ml, and 3–6 ng of biotinylated chromosome 4 unique sequences (40–80 ng of total phage DNA)] was then denatured (70° C. for 5 min) and applied. Hybridization was at 37° C. overnight (16 hr). Slides were washed in three changes of 50% formamide/0.3 M NaCl/30 mM sodium citrate (final concentration), pH 7, at 45° C. for 5 min each and once in PN buffer (a mixture of 0.1 M $NaH_2PO_4$ and 0.1 M $Na_2HPO_4$ to give pH 8/0.1% Nonidet P-40). The slides were then treated with alternating layers of fluoresceinated avidin and biotinylated goat antiavidin, both at 5 ug/ml in PNM buffer (PN buffer/5% non-fat dry milk/0.02% sodium azide, centrifuged to remove solids), for 20 min each at room temperature until three layers of avidin were applied. The avidin and goat anti-avidin treatments were separated by three washes of 3 min each in PN buffer [avidin (DCS grade) and anti-avidin from Vector Laboratories (Burlingame, Calif.)]. After the final avidin treatment, a fluorescence antifade solution [Johnson and Noqueria, *J. Immunol. Methods*, 43: 349 (1981)] containing 1 ug of 4',6-amidino-2-phenylindole or propidium iodide per ml was applied as a counterstain (1.5 $ul/cm^2$ under a no. 1 coverslip).

Results. As shown in FIG. 4H, individual hybridization sites could be located to within a fraction of the width of a chromatid after overnight hybridization (16 hr) and application of three layers of avidin. Analysis of three spreads from the hybridization with the 120 unique sequence probes at a total probe concentration of 1.5 pg/ul per kilobase of human insert, showed 222 fluorescent spots out of the 1440 possible on the number 4 chromosomes (120 target sites per chromatid×4 chromatids per metaphase×3 metaphases). Thus, the hybridization efficiency was 15%. There were 814 total spots on all of the chromosomes giving a hybridization specificity of 27%. The experiment demonstrates that substantial hybridization can occur with single copy probes at low probe concentrations in overnight hybridizations. The contrast ratio of chromosome 4 relative to the rest of the chromosomes was thus:

$$\frac{\text{spots/length of chromosome 4}}{\text{spots/length of all chromosomes}} = \frac{222/.06}{814/1.0} = \text{approximately} 4.$$

VI. Incapacitating Shared Repetitive Sequences

VI.A. Chromosome 21-Specific Staining Using Blocking DNA

High concentrations of unlabeled human genomic DNA and lambda phage DNA were used to inhibit the binding of repetitive and vector DNA sequences to the target chromosomes. Heavy proteinase digestion and subsequent fixation of the target improved access of probes to target DNA.

Human metaphase spreads were prepared on microscope slides with standard techniques and stored immediately in a nitrogen atmosphere at −20° C.

Slides were removed from the freezer and allowed to warm to room temperature in a nitrogen atmosphere before beginning the staining procedure. The warmed slides were first treated with 0.6 microgram/ml proteinase K in P buffer (20 mM Tris, 2 mM $CaCl_2$ at pH 7.5) for 7.5 minutes, and washed once in P buffer. The amount of proteinase K used needs to be adjusted for different batches of slides. After denaturing the slides were stored in 2×SSC. A hybridization mix was prepared which consisted of 50% formamide, 10% dextran sulfate, 1% Tween 20, 2×SSC, 0.5 mg/ml human genomic DNA, 0.03 mg/ml lambda DNA, and 3 microgram/ml biotin labeled probe DNA. The probe DNA consisted of the highest density fraction of phage from the chromosome 21 Hind III fragment library (ATCC accession number 57713), as determined by a cesium chloride gradient. (Both insert and phage DNA of the probe were labeled by nick translation.) The average insert size (amount of chromosome 21 DNA), as determined by gel electrophoresis was about 5 kilobases. No attempt was made to remove repetitive sequences from the inserts or to isolate the inserts from the lambda phage vector. The hybridization mix was denatured by heating to 70° C. for 5 minutes followed by incubation at 37° C. for 1 hour. The incubation allows the human genomic DNA and unlabeled lambda DNA in the hybridization mix to block the human repetitive sequences and vector sequences in the probe.

Figure 1B:
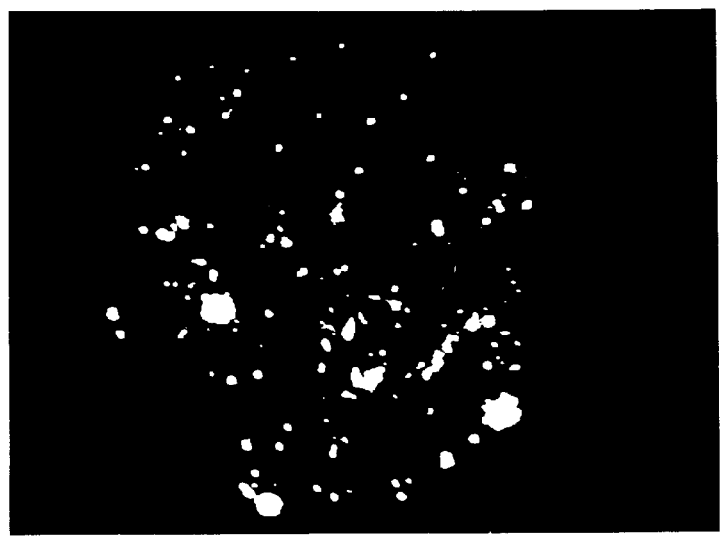
FIG. 1B is a binary image of the FITC staining of the same human metaphase spread as in FIG. 1A. The image was processed as in FIG. 1A but the filter was changed in the microscope such that the FITC attached to the probe is visible rather than the DAPI.
Figure 1C:
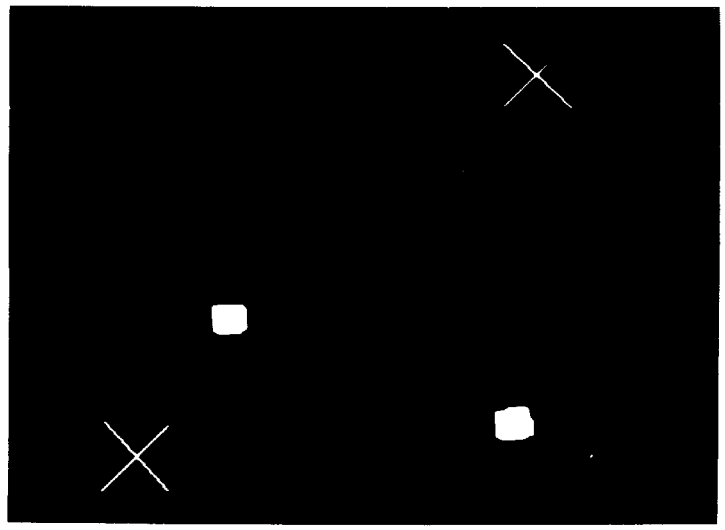
FIG. 1C is a binary image of the chromosome 21s alone, nonspecifically stained objects (which are smaller) having been removed by standard image processing techniques on the binary image of FIG. 1B.
Figure 2A:
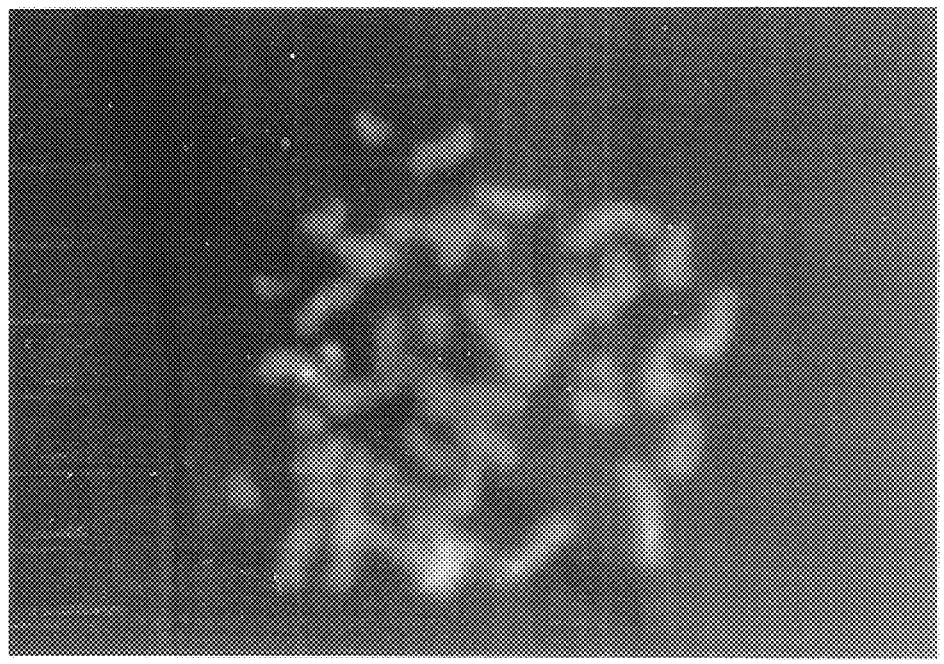
FIGS. 2A and 2B illustrate the hybridization of a chromosome-specific 21 library to human metaphase spread wherein the inserts were cloned in Lambda phage Charon 21A. The hybridization capacity of the high copy repetitive sequences in the library was reduced by the addition of unlabeled genomic DNA to the hyridization mixture. The probe was labeled with biotin, which was detected with green FITC-avidin (fluorescein isothiocyanate avidin). All of the DNA in the chromosomes was stained with the blue fluorescent dye DAPI (4,6-diamidino-2-phenylindole).
Figure 2B:
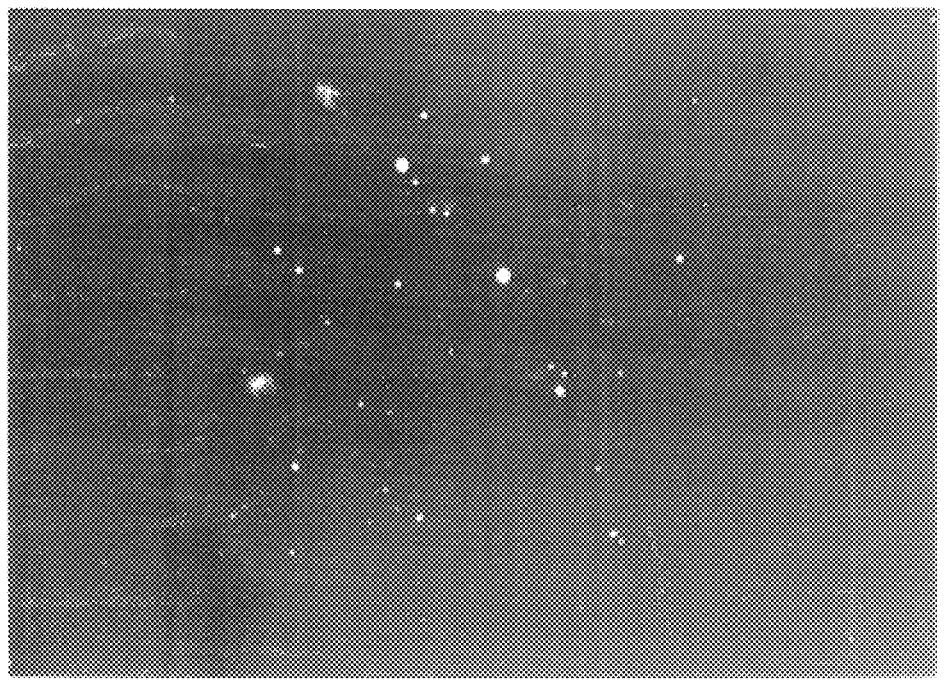

The slide containing the human metaphase spread was removed from the 2×SSC and blotted dry with lens paper. The hybridization mix was immediately applied to the slide, a glass cover slip was placed on the slide with rubber cement, and the slide was incubated overnight at 37° C. Afterwards preparation of the slides proceeded as described in Section V.B. (wherein chromosome 21 DNA was stained with fluorescein and total chromosomal DNA counterstained with DAPI). FIGS. 1A–C illustrate the results. FIG. 1A is a DAPI image of the human metaphase spread obtained with a computerized image analysis system. It is a binary image showing everything above threshold as white, and the rest as black. The primary data was recorded as a gray level image with 256 intensity levels. (Small arrows indicate the locations of the chromosome 21s.) FIG. 1B is a fluorescein image of the same spread as in FIG. 1A, again in binary form. (Again, small arrows indicate the locations of the chromosome 21s.) FIG. 1C illustrates the positions of the chromosome 21s after other less densely stained objects were removed by standard image processing techniques.

VI.B. Detection of Trisomy 21 and Translocations of Chromosome 4 Using Bluescribe Plasmid Libraries As illustrated in Section VI.A., a human chromosome-specific library, including its shared repetitive sequences, can be used to stain that chromosome if the hybridization capacity of the shared repetitive sequences is reduced by incubation with unlabeled human genomic DNA. In Section VI.A., the nucleic acid sequences of the heterogeneous mixture were cloned in the phage vector Charon 21A, in which the ratio of insert of vector DNA is about 0.1 (4 kb average insert to 40 kb of vector). In this section, we demonstrate that transferring the same inserts to a smaller cloning vector, the about 3 kb Bluescribe plasmid, which increases the ratio of insert to vector DNA to 0.5, improved the specificity and intensity of the staining.

As previously discussed, incubation of the probe can be carried out wish the probe alone, with the probe mixed with unlabeled genomic DNA, and with the probe mixed with unlabeled DNA enriched in all or some shared repetitive sequences. If unlabeled genomic DNA is added, then it is important to add enough to incapacitate sufficiently the shared repetitive sequences in the probe. However, the genomic DNA also contains unlabeled copies of the sequences, the hybridization of which is desired. As explained above, Q is herein defined as the ratio of unlabeled to labeled copies of the chromosome-specific sequences in the hybridization mixture.

Cells. Metaphase spreads from human lymphocytes were prepared from methotrexate-synchronized cultures by using the procedure of Harper et al. supra. These and all other cells used in this example were fixed in methanol/acetic acid, 3:1. Other human lymphocyte cultures were irradiated with $^{60}$Co gamma rays and stimulated with phytohemagglutnin. Colcemid was added 48 hr after stimulation and metaphase spreads were prepared 4 hr later. Metaphase spreads and interphase cells from lymphoblastoid cells (GM03716A; Human Mutant Cell Repository, Camden, N.J.) carrying trisomy 21 were prepared after a 4-hr colcemid block. Interphase cells from the cell line RS4;11 carrying t(4;11) and isochromosome 7q were harvested, fixed in methanol/acetic acid, and dropped onto slides [Strong et al., *Blood*, 65:21 (1985)]. Slides were stored at −20° C. in plastic bags filled with nitrogen gas.

pBS-4. The entire chromosome 4 library LL04NS02 (ATCC accession number 57745; Van Dilla et al., supra) was subcloned into Bluescribe plasmids (Stratagene La Jolla, Calif.) to form the library pBS-4. The average insert to vector DNA ratio in pBS-4 is about 1. The plasmid library was amplified in bulk and the DNA was extracted using DEAE-cellulose columns (Whatman DE-52) [Helms et al., *DNA*, 4:39 (1985)]. The DNA was then biotinylated by nick translation with biotin-11-dUTP (Bethesda Research Laboratories) and recovered at a concentration of about 20 ng/ul using Sephadex G-50 spin columns. In some experiments, the biotinylated DNA was concentrated by ethanol precipitation to achieve higher probe concentrations.

pBS-21. The entire chromosome 21 library LL21NS02 (ATCC accession number 57713; Van Dilla et al., supra) was subcloned into Bluescribe plasmids to form the library pBS-21. This library was amplified and biotinylated as described above for pBS-4.

Human genomic DNA. Placental DNA (Sigma) was treated with proteinase K, extracted with phenol, and sonicated to a size range of 200–600 base pairs (bp).

Whole Library Hybridization. Hybridization was as above in section V.C except that RNase, proteinase K, and paraformaldehyde were not used. The amount of probe and genomic DNA in the hybridization mixture and the length of the hybridization varied as described in Results. All probe concentrations refer to the human insert DNA unless otherwise noted. DNA concentrations were determined by fluorometric analysis (Hoeffer Scientific Instruments, San Francisco). Incubation of the hybridization mixture prior to hybridization followed two different protocols as indicated immediately below.

Protocol I. The hybridization mixture (10 ul) contained 10–150 ng of biotinylated human DNA (20–300 ng of total plasmid DNA) and 0–10 ug of unlabeled genomic DNA. The mixture was heated to denature the DNA and incubated at 37° C. for a time t before it was added to the slide. Hybridization times ranged from 2 to 110 hr.

Protocol II. Protocol II was identical to Protocol I except that an additional aliquot of freshly denatured genomic DNA was added to the hybridization mixture after an incubation time t. The mixture was then incubated an additional time t prior to starting the hybridization. The volume of the hybridization mixture was increased <20% by the additional genomic DNA.

Microscopy. Quantitative fluorescence measurements were performed using a video camera on the microscope and a digital image processing system, [Trask et al., *Human Genet.*, 78:251 (1988)].

Results. FIG. 4A shows hybridization of pBS-4 to a human metaphase spread with a probe concentration of 1 ng/ul. No genomic DNA was used and the hybridization mixture was applied immediately after denaturation. All of the chromosomes are stained, except near many centromeres, with two copies of chromosome 4 being stained most heavily. All the chromosomes are stained along most of their lengths due to sequences in the probe which are shared with other chromosomes. Unstained regions, noted by arrows, show locations for which homologous sequences are not present in pBS-4. The unstained regions are mostly centromeric and along the long arm of the Y chromosome. Blocks of repetitive DNA specific to those sites are known to exist.

The visible contrast on chromosome 4 is the result of the interaction of several factors. (i) All of the DNA in chromosome 4 is potential target for sequences in the probe, whereas only those sequences on the other chromosomes that are shared with chromosome 4 can bind probe. (ii) The hybridization time and probe concentration were high enough to allow significant binding of the specific sequences in the probe. (iii) The ratio of probe to target sequences is higher for the specific sequences than for the shared sequences [Ten nanograms of chromosome 4 DNA was hybridized to about 200 ng of human DNA target ($4\times10^4$ cells), 13 ng of which is chromosome 4. Thus, the ratio of probe to target for the specific sequences was about 1, whereas for the shared sequences it was about 0.05.]

The contrast can be increased by allowing the denatured probe DNA to partially reassociate prior to adding it to the slide, preferentially depleting the single-stranded high-copy (predominantly the shared) sequences in the probe [Cantor & Schimmel, *Biophysical Chemistry: The Behavior of Biological Macromolecules*, (part III, p. 1228) (Freeman 1980)]. A significant increase in staining specificity resulting from probe reassociation was observed experimentally for chromosome 4 using a hybridization mixture with 1 ng of probe per microliter (ul) and a 24-hr incubation at 37° C. prior to in situ hybridization (not shown). Likewise, hybridization after a 24 hr incubation of 4 ng of chromosome 21 probe per ul resulted in a substantial contrast ratio. That result indicates that at such concentrations the chromosome-specific sequences remain substantially single stranded for times on the order of days in the hybridization mixture. It also demonstrates that other mechanisms that might inactivate the probe are not significant during the incubation.

FIGS. 4B and 4C show the result of a protocol I hybridization [0.8 ng of probe per ul and 24 ng of genomic DNA per ul (Q=2); 1-hr probe incubation and 110-hr hybridization]. Quantitative image analysis shows that the intensity per unit length of the FITC fluorescein on chromosome 4 is approximately 20 times that of the other chromosomes, that is the contrast ratio is 20:1. Two layers of avidin-fluorescein isothiocyanate have been used here to make the non-target chromosomes sufficiently bright to be measured accurately. However, the number 4 chromosomes can be recognized easily after a single layer.

FIG. 4D demonstrates detection of a radiation-induced translocation involving chromosome 4 in human lymphocytes [protocol I, 1 ng of probe per ul and 76 ng of genomic DNA per ul (Q=5); 1-hr probe incubation and 16-hr hybridization]. The contrast ratio was about 5. The hybridization intensity and specificity shown in FIG. 4D are such that even small portions of the involved chromosome can be detected.

The ease with which translocations can be recognized offers the opportunity for translocation detection by automated means, such as, computerized microscopy or flow cytometry. [See Section VIII infra for elaboration concerning automated detection means.]

FIG. 4E shows that the normal and two derivative chromosomes resulting from the translocation between chromosomes 4 and 11 [t(4;11)] in cell line RS4;11 can be detected in interphase nuclei as three distinct domains [protocol I, 13.5 ng of probe per ul and 800 ng of genomic DNA per ul (Q=5); 1-hr probe incubation and 16-hr hybridization]. The increased probe concentration resulted in brighter signals relative to FIG. 4D. Approximately half of the cells clearly show the presence of three nuclear domains, presumably produced by the two portions of the involved chromosome 4 and the intact normal chromosome. The domains in the other nuclei may have been obscured by the nuclear orientation in these two-dimensional views, by nuclear distortion that occurred during slide preparation, or because the domains were too close to each other to be distinguished. Hybridization using procedures that preserve three-dimensional morphology may resolve these issues and also permit general studies of chromosomal domains in interphase nuclei [Trask et al., *Hum. Genet.*, 78: 251 (1988)].

Hybridization of pBS-21 to a metaphase spread from a cell line with trisomy 21 is shown in FIG. 4F [protocol II, 4 ng of probe per ul and 250 ng of genomic DNA per ul; 3-hr incubation, additional 250 ng of genomic DNA per ul (Q=1+1); 3-hr probe incubation and 16-hr hybridization]. A small amount of hybridization is visible near the centromeres of the other acrocentric chromosomes.

FIG. 4G shows two interphase nuclei from the same hybridization which clearly show the three chromosome 21 domains. Hybridization with probe prepared according to protocol I resulted in higher relative intensity of the shared signals on the D- and G-group chromosomes, and consequently it was more difficult to determine the number of number 21 chromosomes in interphase (not shown). Increasing stringency by using a hybridization mixture with 55% formamide and 0.15 M NaCl/15 mM sodium citrate, which lowers the melting temperature about 8° C., did not reduce the unwanted hybridization. Addition of unlabeled pA ribosomal DNA [Erikson et al., *Gene*, 16:1 (1981)] also was ineffective at increasing specificity.

The centromeric region of the D- and G-group chromosomes contain ribosomal [Erikson et al., id] and alpha satellite sequences and perhaps others [Choo et al., *Nucleic Acids Res.*, 16: 1273 (1988)]. These are relatively low copy sequences shared with only a few chromosomes, so Protocol I is not very effective at suppressing them relative to the chromosome 21-specific sequences. In addition, these sequences are clustered on the chromosomes, so that even much reduced hybridization is clearly visible. This is especially distracting in analysis of interphase nuclei. Calculations indicate that addition of several aliquots of freshly denatured genomic DNA periodically during the incubation (protocol II) should increase the staining specificity. FIG. 4F shows a protocol II hybridization, using two aliquots of genomic DNA, to a metaphase spread from a trisomy 21 cell line. Intense hybridization to the three number 21 chromosomes is clearly visible and hybridization to the other D- and G-group chromosomes has been reduced to an acceptable level. FIG. 4G shows that hybridization to chromosomes other than chromosome 21 is sufficiently low that the three chromosome 21 domains are clearly visible in interphase nuclei. In practice, the most convenient procedure for suppressing the shared acrocentric hybridization might be inclusion of unlabeled DNA from one of the other D- or G-group chromosome libraries (or unlabeled cloned DNA from just these sequences, if available) as additional competitor. The use of libraries from non-target chromosomes as blocker for a probe may in general improve contrast. The specific sequences in the probe will not be blocked (Q=0) no matter how much competitor for the shared sequences is added.

VI.C. Hybridization of Yeast Artificial Chromosomes (YACS) to Human Metaphase Spread YACS. Seven yeast clones HY1, HY19, HY29, HYA1.A2, HYA3.A2, HYA3.A9, and HYA9.E6 were obtained from D. Burke (Washington University, St. Louis, Mo.). The lengths of the human DNA in the clones ranged from about 100 kb to about 600 kb. Gel electrophoresis was performed to verify the size of these inserts. Each of these clones was grown up and total DNA was isolated. The isolated DNA was biotinylated by nick translation so that 10–30% of the thymidine was replaced by biotin-11-dUTP. The concentration of the total labeled DNA after nick translations is in the range of 10–20 ng/ul.

Blocking DNA. Human placental DNA (Sigma) was treated with proteinase K and extracted with phenol and sonicated to a size range of 200–600 bp. Total DNA isolated from yeast not containing an artificial chromosome was sonicated to a similar size range. Both of these DNA's were maintained at a concentration of 1–10 ug/ul.

Fluorescence in situ Hybridization (FISH).

Hybridization followed the procedures of Pinkel et al. (1988), supra (as exemplified in Sections V and VI, supra) with slight modifications. Metaphase spreads were prepared from methotrexate synchronized cultures according to the procedures of Harper et al. *PNAS* (USA) 78: 4458–4460, (1981). Cells were fixed in methanol/acetic acid, fixed (3:1), dropped onto slides, air dried, and stored at −20° C. under nitrogen gas until used. The slides were then immersed two minutes in 70% formamide/2×SSC to denature the target DNA sequences, dehydrated in a 70–85–100% ethanol series, and air dried. (SSC is 0.15 M NaCl/0.015 M Na Citrate, pH 7). Ten–100 ng of biotinylated yeast DNA, and approximately 1 ug each of unlabeled yeast and human genomic DNA were then added to the hybridization mix (final volume 10 ul, final composition 50% formamide/2× SSC/10% dextran sulfate), heated to 70° C. for 5 min., and then incubated at 37° C. for 1 hr to allow the complementary strands of the more highly repeated sequences to reassociate.

The hybridization mixture was then applied to the slide (approximately 4 cm² area) and sealed with rubber cement under a glass cover slip. After overnight incubation at 37° C. the coverslip was removed and the slide washed 3 times 3 min each in 50% formamide/2×SSC at 42–45° C., and once in PN buffer [mixture of 0.1 M $NaH_2PO_4$ and 0.1 M $Na_2HPO_4$ to give pH 8; 0.1% Nonidet P-40 (Sigma)]. The bound probe was then detected with alternating 20 min incubations (room temperature in avidin-FITC and goat-anti-avidin antibody, both at 5 ug/ml in PNM buffer (PN buffer plus 5% nonfat dry milk, centrifuged to remove solids; 0.02% Na azide). Avidin and anti-avidin incubation were separated by 3 washes of 3 min each in PN buffer. Two or three layers of avidin were applied (Avidin, DCS grade, and biotinylated goat-anti-avidin are obtained from Vector Laboratories Inc., Burlingame, Calif.).

Figure 5:
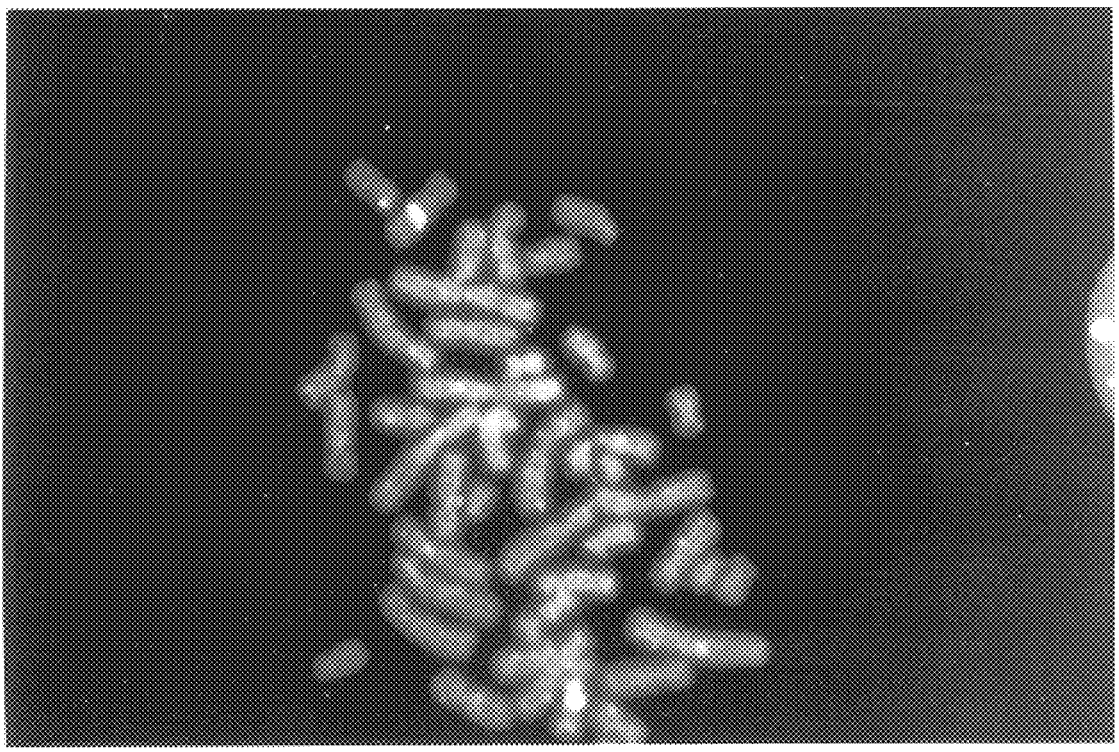
FIG. 5 shows the hybridization of a yeast artificial chromosome (YAC) clone containing a 580 kb insert of human DNA to a human metaphase spread. A yellow fluorescein band on each of the chromosome 12s (at 12q21.1) is visible against the propidium iodide counterstain.

FIG. 5 shows the hybridization of HYA3.A2 (580 kb of human DNA) to 12q21.1. The location of the hybridization was estabilished by using a conventional fluorescent banding technique employing the DAPI/actinomycin D procedure: Schweizer, "Reverse fluorescent chromosome banding with chromomycin and DAPI," *Chromosoma*, 58: 307–324

(1976). The hybridization signal forms a band across the width of each of the chromosome 12s, indicating the morphology of the packing of DNA in that region of the chromosome.

The YAC clone positions are attributed as shown in Table 2 below.

TABLE 2

YAC Competition Hybridization

| YAC Clone | Insert Size | Localization |
|---|---|---|
| HY1 | 120 | Xq23 |
| HY19 | 450 | 8q23.3 |
| | | 21q21.1 |
| HY29 | 500 | 14q12 |
| HYA1.A2 | 250 | 6q16 |
| HYA3.A2 | 580 | 12q21.1 |
| HYA3.A9 | 600 | 14q21 |
| HYA9.E6 | 280 | 1p36.2 |
| | | 3q22 |

VI.D. Hybridization With Human/Hamster Hybrid Cell

Figure 6:
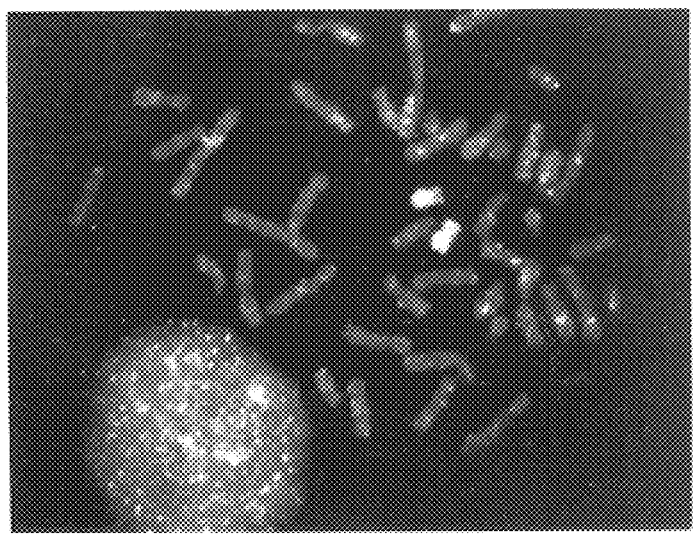
FIG. 6 shows the hybridization of DNA from a human/hamster hybrid cell containing one copy of human chromosome 19 to a human metaphase spread. A little to the right of the photograph's center are the two chromosome 19s which are brighter than the other chromosomes in the spread.

Essentially the same hybridization and staining conditions were used in this example as for those detailed in the procedure of Pinkel et al. (1988), supra and exemplified in Sections V.C. and VI.B., supra. In this example, 400 ng of biotin labeled DNA from a hamster-human hybrid cell that contains one copy of human chromosome 19 was mixed with 1.9 ug of unlabeled human genomic DNA in 10 ul of hybridization mix. Hybridization was for approximately 60 hours at 37° C. Fluorescent staining of the bound probe and counterstaining of the chromosomes was as in the other examples above. FIG. 6 shows the results of the hybridization.

VII. Specific Applications

The present invention allows microscopic and in some cases flow cytometric detection of genetic abnormalities on a cell by cell basis. The microscopy can be performed entirely by human observers, or include various degrees of addititional instrumentation and computational assistance, up to full automation. The use of instrumentation and automation for such analyses offers many advantages. Among them are the use of fluorescent dyes that are invisible to human observers (for example, infared dyes), and the opportunity to interpret results obtained with multiple labeling methods which might not be simultaneously visible (for example, combinations of fluorescent and absorbing stains, autoradiography, etc.) Quantitative measurements can be used to detect differences in staining that are not detectable by human observers. As is described below, automated analysis can also increase the speed with which cells and chromosomes can be analysed.

The types of cytogenetic abnormalities that can be detected with the probes of this invention include: Duplication of all or part of a chromosome type can be detected as an increase in the number or size of distinct hybridization domains in metaphase spreads or interphase nuclei following hybridization with a probe for that chromosome type or region, or by an increase in the amount of bound probe. If the probe is detected by fluorescence, the amount of bound probe can be determined either flow cytometrically or by quantitative fluorescence microscopy. Deletion of a whole chromosome or chromosome region can be detected as a decrease in the number or size of distinct hybridization domains in metaphase spreads or interphase nuclei following hybridization with a probe for that chromosome type or region, or by a decrease in the amount of bound probe. If the probe is detected by fluorescence, the amount bound can be determined either flow cytometrically or by quantitative fluorescence microscopy. Translocations, dicentrics and inversions can be detected in metaphase spreads and interphase nuclei by the abnormal juxtaposition of hybridization domains that are normally separate following hybridization with probes that flank or span the region(s) of the chromosome(s) that are at the point(s) of rearrangement. Translocations involve at least two different chromosome types and result in derivative chromosomes possessing only one centromere each. Dicentrics involve at least two different chromosome types and result in at least one chromosome fragment lacking a centromere and one having two centromeres. Inversions involve a reversal of polarity of a portion of a chromosome.

VII.A Banding Analysis

Substantial effort has been devoted during the past thirty years to development of automated systems (especially computer controlled microscopes) for automatic chromosome classification and aberration detection by analysis of metaphase spreads. In recent years, effort has been directed at automatic classification of chromosomes which have been chemically stained to produce distinct banding patterns on the various chromosome types. These efforts have only partly succeeded because of the subtle differences in banding pattern between chromosome types of approximately the same size, and because differential contraction of chromosomes in different metaphase spreads causes a change in the number and width of the bands visible on chromosomes of each type. The present invention overcomes these problems by allowing construction of reagents which produce a staining pattern whose spacing, widths and labeling differences (for example different colors) are optimized to facilitate automated chromosome classification and aberration detection. This is possible because hybridization probes can be selected as desired along the lengths of the chromosomes. The size of a band produced by such a reagent may range from a single small dot to a substantially uniform coverage of one or more whole chromosomes. Thus the present invention allows construction of a hybridization probe and use of labeling means, preferably fluorescence, such that adjacent hybridization domains can be distinguished, for example by color, so that bands too closely spaced to be resolved spatially can be detected spectrally (i.e, if red and green fluorescing bands coalesce, the presence of the two bands can be detected by the resulting yellow fluorescence).

The present invention also allows construction of banding patterns tailored to particular applications. Thus they can be significantly different in spacing and color mixture, for example, on chromosomes that are similar in general shape and size and which have similar banding patterns when conventional techniques are used. The size, shape and labeling (e.g. color) of the hybridization bands produced by the probes of the present invention can be optimized to eliminate errors in machine scoring so that accurate automated aberration detection becomes possible. This optimized banding pattern will also greatly improve visual chromosome classification and aberration detection.

The ease of recognition of specific translocation breakpoints can be improved by using a reagent closely targeted to the region of the break. For example, a high complexity probe of this invention comprising sequences that hybridize to both sides of the break on a chromosome can be used. The portion of the probe that binds to one side of the break can be detected differently than that which binds to the other, for example with different colors. In such a pattern, a normal chromosome would have the different colored hybridization regions next to each other, and such bands would appear close together. A break would separate the probes to different chromosomes or result in chromosomal fragments, and could be visualized as much further apart on an average.

VII.B Biological Dosimetry

One approach to biological dosimetry is to measure frequencies of structurally aberrant chromosomes as an indication of the genetic damage suffered by individuals exposed to potentially toxic agents. Numerous studies have indicated the increase in structural aberration frequencies with increasing exposure to ionizing radiation and other agents, which are called clastogens. Dicentric chromosomes are most commonly scored because their distinctive nature allows them to be scored rapidly without banding analysis. Rapid analysis is important because of the low frequency of such aberrations in individuals exposed at levels found in workplaces ($\sim 2 \times 10^{-3}$/cell). Unfortunately, dicentrics are not stably retained so the measured dicentric frequency decreases with time after exposure. Thus low level exposure over long periods of time does not result in an elevated dicentric frequency because of the continued clearance of these aberrations. Translocations are better aberrations to score for such dosimetric studies because they are retained more or less indefinitely. Thus, assessment of genetic damage can be made at times long after exposure. Translocations are not routinely scored for biological dosimetry because the difficulty of recognizing them makes scoring sufficient cells for dosimetry logistically impossible.

The present invention eliminates this difficulty. Specifically, hybridization with a probe which substantially uniformly stains several chromosomes (e.g. chromosomes 1, 2, 3 and 4) allows immediate microscopic identification in metaphase spreads of structural aberrations involving these chromosomes. Normal chromosomes appear completely stained or unstained by the probe. Derivative chromosomes resulting from translocations between targeted and non-targeted chromosomes are recognized as being only partly stained, FIG. 4D. Such partially hybridized chromosomes can be immediately recognized either visually in the microscope or in an automated manner using computer assisted microscopy. Discrimination between translocations and dicentrics is facilitated by adding to the probe, sequences found at all of the chromosome centromeres. Detection of the centromeric components of the probe with a labeling means, for example color, different from that used to detect the rest of the probe elements allows ready identification of the chromosome centromeres, which in turn facilitates discrimination between dicentrics and translocations. This technology dramatically reduces the scoring effort required with previous techniques so that it becomes feasible to examine tens of thousands of metaphase spreads as required for low level biological dosimetry.

VII.C. Prenatal Diagnosis

The most common aberrations found prenatally are trisomies involving chromosomes 21 (Down syndrome), 18 (Edward syndrome) and 13 (Patau syndrome) and X0 (Turner syndrome), XXY (Kleinfelter syndrome) and XYY disease. Structural aberrations also occur. However, they are rare and their clinical significance is often uncertain. Thus, the importance of detecting these aberrations is questionable. Current techniques for obtaining fetal cells for conventional karyotyping, such as, amniocentesis and chorionic villus biopsy yield hundreds to thousands of cells for analysis. These are usually grown in culture for 2 to 5 weeks to produce sufficient mitotic cells for cytogenetic analysis. Once metaphase spreads are prepared, they are analyzed by conventional banding analysis. Such a process can only be carried out by highly skilled analysts and is time consuming so that the number of analyses that can be reliably carried out by even the largest cytogenetics laboratories is only a few thousand per year. As a result, prenatal cytogenetic analysis is usually limited to women whose children are at high risk for genetic disease (e.g. to women over the age of 35).

The present invention overcomes these difficulties by allowing simple, rapid identification of common numerical chromosome aberrations in interphase cells with no or minimal cell culture. Specifically, abnormal numbers of chromosomes 21, 18, 13, X and Y can be detected in interphase nuclei by counting numbers of hybridization domains following hybridization with probes specific for these chromosomes (or for important regions thereof such as 21q22 for Down syndrome). A hybridization domain is a compact, distinct region over which the intensity of hybridization is high. An increased frequency of cells showing three domains (specifically to greater than 10%) for chromosomes 21, 18 and 13 indicates the occurrence of Down, Edward and Patau syndromes, respectively. An increase in the number of cells showing a single X-specific domain and no Y-specific domain following hybridization with X-specific and Y-specific probes indicates the occurrence of Turner syndrome. An increase in the frequency showing two X-specific domains and one Y-specific domain indicates Kleinfelter syndrome, and increase in the frequency of cells showing one X-specific domain and two Y-specific domains indicates an XYY fetus. Domain counting in interphase nuclei can be supplemented (or in some cases replaced) by measurement of the intensity of hybridization using, for example, quantitative fluorescence microscopy or flow cytometry, since the intensity of hybridization is approximately proportional to the number of target chromosomes for which the probe is specific. Numerical aberrations involving several chromosomes can be scored simultaneously by detecting the hybridization of the different chromosomes with different labeling means, for example, different colors. These aberration detection procedures overcome the need for extensive cell culture required by procedures since all cells in the population can be scored. They eliminate the need for highly skilled analysts because of the simple, distinct nature of the hybridization signatures of numerical aberrations. Further, they are well suited to automated aberration analysis.

The fact that numerical aberrations can be detected in interphase nuclei also allows cytogenetic analysis of cells that normally cannot be stimulated into mitosis. Specifically, they allow analysis of fetal cells found in maternal peripheral blood. Such a feature is advantageous because it eliminates the need for invasive fetal cell sampling such as amniocentesis or chorionic villus biopsy.

As indicated in the Background, the reason such embryo-invasive methods are necessary is that conventional karyotyping and banding analysis requires metaphase chromosomes. At this time, there are no accepted procedures for culturing fetal cells separated from maternal blood to provide a population of cells having metaphase chromosomes. In that the staining reagents of this invention can be employed with interphase nuclei, a non-embryo-invasive method of karyotyping fetal chromosomes is provided by this invention.

The first step in such a method is to separate fetal cells that have passed through the placenta or that have been shed by the placenta into the maternal blood. The incidence of fetal cells in the maternal bloodstream is very low, on the order of $10^{-4}$ to $10^{-6}$ cells/ml and quite variable depending on the time of gestation; however, appropriately marked fetal cells may be distinguished from maternal cells and concentrated, for example, with high speed cell sorting.

The presence of cells of a male fetus may be identified by a label, for example a fluorescent tag, on a chromosome-specific staining reagent for the Y chromosome. Cells that were apparently either lymphocytes or erythrocyte precursors that were separated from maternal blood were shown to be Y-chromatin-positive. [Zillacus et al., Scan. J. Haematol, 15: 333 (1975); Parks and Herzenberg, Methods in Cell Biology, Vol. 10, pp. 277–295 (Academic Press, N.Y., 1982); and Siebers et al., Humangenetik, 28: 273 (1975)].

A preferred method of separating fetal cells from maternal blood is the use of monoclonal antibodies which preferentially have affinity for some component not present upon the maternal blood cells. Fetal cells may be detected by paternal HLA (human leukocyte antigen) markers or by an antigen on the surface of fetal cells. Preferred immunochemical procedures to distinguish between fetal and maternal leukocytes on the basis of differing HLA type use differences at the HLA-A2, -A3, and -B7 loci, and further preferred at the -A2 locus. Further, first and second trimester fetal trophoblasts may be marked with antibody against the internal cellular constituent cytokeratin which is not present in maternal leukocytes. Exemplary monoclonal antibodies are described in the following references.

Herzenberg et al., PNAS, 76: 1453 (1979), reports the isolation of fetal cells, apparently of lymphoid origin, from maternal blood by fluorescence activated cell sorting (FACS) wherein the separation was based on the detection of labeled antibody probes which bind HLA-A2 negative cells in maternal blood. Male fetal cells separated in that manner were further identified by quinacrine staining of Y-chromatin.

Covone et al., Lancet, Oct. 13, 1984: 841, reported the recovery of fetal trophoblasts from maternal blood by flow cytometry using a monoclonal antibody termed H315. Said monoclonal reportedly identifies a glycoprotein expressed on the surface of the human syncytiotrophoblast as well as other trophoblast cell populations, and that is absent from peripheral blood cells.

Kawata et al., J. Exp. Med., 160: 653 (1984), discloses a method for isolating placental cell populations from suspensions of human placenta. The method uses coordinate two-color and light-scatter FACS analysis and sorting. Five different cell populations were isolated on the basis of size and quantitative differences in the coordinate expression of cell surface antigens detected by monoclonal antibodies against an HLA-A, B, C monomorphic determinant (MB40.5) and against human trophoblasts (anti-Trop-1 and anti-Trop-2).

Loke and Butterworth, J. Cell Sci., 76: 189 (1985), describe two monoclonal antibodies, 18B/A5 and 18A/C4, which are reactive with first trimester cytotrophoblasts and other fetal epithelial tissues including syncytiotrophoblasts.

A preferred monoclonal antibody to separate fetal cells from maternal blood for staining according to this invention is the anti-cytokeratin antibody Cam 5.2, which is commercially available from Becton-Dickinson (Franklin Lakes, N.J., USA).

Other preferred monoclonal antibodies for separating fetal cells from maternal blood are those disclosed in co-pending, commonly owned U.S. Pat. application Ser. No. 389,224, filed Aug. 3, 1989, entitled "Method for Isolating Fetal Cytotrophoblast Cells". [See also: Fisher et al., J. Cell. Biol., 109 (2): 891–902 (1989)]. The monoclonal antibodies disclosed therein react specifically with antigen on first trimester human cytotrophoblast cells, which fetal cells have the highest probability of reaching the maternal circulation. Said application and article are herein specifically incorporated by reference. Briefly, the disclosed monoclonal antibodies were raised by injection of test animals with cytotrophoblast cells obtained from sections of the placental bed, that had been isolated by uterine aspiration. Antibodies raised were subjected to several cytological screens to select for those antibodies which react with the cytotrophoblast stem cell layer of first trimester chorionic villi.

Preferred monoclonal antibodies against such first trimester cytotrophoblast cells disclosed by Fisher et al. include monoclonal antibodies produced from the following hybridomas deposited at the American Tyupe Culture Collection (ATCC; Rockville, Md., USA) under the Budapest Treaty:

| Hybridoma | ATCC Accession # |
|---|---|
| J1D8 | HB10096 |
| P1B5 | HB10097 |

Both hybridoma cultures were received by the ATCC on Apr. 4, 1989 and reported viable thereby on Apr. 4, 1989.

Fisher et al. state that fetal cells isolated from maternal blood by use of said monoclonal antibodies are capable of replication in vitro. Therefore, fetal cells isolated by the method of Fisher et al., that is, first trimester fetal cytotrophoblasts, may provide fetal chromosomal material that is both in metaphase and in interphase.

The fetal cells, preferably leukocytes and cytotrophoblasts, more preferably cytotrophoblasts, once marked with an appropriate antibody are then separated from the maternal cells either directly or by preferably separating and concentrating said fetal cells by cell sorting or panning. For example, FACS may be used to separate fluorescently labeled fetal cells, or flow cytometry may be used.

The fetal cells once separated from the maternal blood can then be stained according to the methods of this invention with appropriate chromosome-specific staining reagents of this invention, preferably those of particular importance for prenatal diagnosis. Preferred staining reagents are those designed to detect aneuploidy, for example, trisomy of any of several chromosomes, including chromosome types 21, 18, 13, X and Y and subregions on such chromosomes, such as, subregion 21q22 on chromosome 21.

Preferably, a fetal sample for staining analysis according to this invention comprises at least 10 cells or nuclei, and more preferably about 100 cells or nuclei.

VII.D Tumor Cytogenetics

Numerous studies in recent years have revealed the existence of structural and numerical chromosome aberrations that are diagnostic for particular disease phenotypes and that provide clues to the genetic nature of the disease itself. Prominent examples include the close association between chronic myelogeneous leukemia and a translocation involving chromosome 9 and 22, the association of a deletion of a portion of 13q14 with retinoblastoma and the association of a translocation involving chromosomes 8 and 14 with Burkitts lymphoma. Current progress in elucidating new tumor specific abnormalities is limited by the difficulty of producing representative, high quality banded metaphase spreads for cytogenetic analysis. These problems stem from the fact that many human tumors are difficult or impossible to grow in culture. Thus, obtaining mitotic cells is usually difficult. Even if the cells can be grown in culture, there is the significant risk that the cells that do grow may not be representative of the tumorigenic population. That difficulty also impedes the application of existing genetic knowledge to clinical diagnosis and prognosis.

The present invention overcomes these limitations by allowing detection of specific structural and numerical aberrations in interphase nuclei. These aberrations are detected as described supra. Hybridization with whole chromosome probes will facilitate identification of previously unknown aberrations thereby allowing rapid development of new associations between aberrations and disease phenotypes. As the genetic nature of specific malignancies becomes increasingly well known, the interphase assays can be made increasingly specific by selecting hybridization probes targeted to the genetic lesion. Translocations at specific sites on selected chromosomes can be detected by using hybridization probes that closely flank the breakpoints. Use of these probes allows diagnosis of these specific disease phenotypes. Translocations may be detected in interphase because they bring together hybridization domains that are normally separated, or because they separate a hybridization domain into two, well separated domains. In addition, they may be used to follow the reduction and reemergence of the malignant cells during the course of therapy. Interphase analysis is particularly important in such a application because of the small number of cells that may be present and because they may be difficult or impossible to stimulate into mitosis.

Duplications and deletions, processes involved in gene amplification and loss of heterozygosity, can also be detected in metaphase spreads and interphase nuclei using the techniques of this invention. Such processes are implicated in an increasing number of different tumors.

The descriptions of the foregoing embodiments of the invention have been presented for purpose of illustration and description. They are not intended to be exhaustive or to limit the invention to the precise form disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

All references cited herein are hereby incorporated by reference.

What is claimed is:

1. A method of biological dosimetry comprising measuring the frequency of structurally aberrant chromosomes to determine the level of genetic damage suffered by a subject, wherein the frequency of structurally aberrant chromosomes is measured by staining target interphase chromosomal DNA according to a method which comprises:
    (a) providing 1) labeled nucleic acid that comprises fragments which are substantially complementary to nucleic acid segments within the chromosomal DNA for which detection is desired, and 2) blocking nucleic acid that comprises fragments which are substantially complementary to repetitive segments in the labeled nucleic acid; and
    (b) employing said labeled nucleic acid, blocking nucleic acid, and chromosomal DNA in in situ hybridization so that labeled repetitive segments are substantially blocked from binding to the chromosomal DNA, while hybridization of unique segments within the labeled nucleic acid to the chromosomal DNA is allowed, wherein blocking of the labeled repetitive segments is sufficient to permit detection of hybridized labeled nucleic acid containing unique segments, and wherein the chromosomal DNA is present in a morphologically identifiable chromosome or cell nucleus during the in situ hybridization; wherein the detection of unique segments in the chromosomal DNA indicates structurally aberrant chromosomes and the frequency of structurally aberrant chromosomes is measured to determine levels of generic damage suffered by a subject.

2. The method of claim 1, wherein the structurally aberrant chromosome is a dicentric chromosome or a translocation.

3. The method according to claim 1, wherein the hybridized labeled nucleic acid containing unique segments are detected visually in a microscope or in an automated manner using computer assisted microscopy.

4. The method according to claim 1, wherein a translocation is discriminated from a dicentric by adding to the probe at least one sequence found at all of the chromosome centromeres.

5. The method according to claim 4, wherein the sequence found at the chromosome centromeres is differently labeled from that of the labeled nucleic acid which hybridizes to the unique segments of the chromosomal DNA.

6. The method according to claim 5, wherein the centromere sequence and the labeled nucleic acid are differently labeled by color.

7. The method according to claim 1, wherein one or more chromosomes are stained and wherein the labeled nucleic acid comprises labels of one or more colors to stain said chromosomes.

8. The method according to claim 1, wherein said fragments of labeled nucleic acid are labeled using more than one color.

9. The method according to claim 1, wherein the labeled nucleic acid is a high complexity probe comprising greater than or equal to 50 kb of nucleic acid sequences.

10. A method for biological dosimetry comprising measuring the frequency of structurally aberrant chromosomes by staining target interphase chromosomal DNA with a nucleic acid probe comprising:
    providing labeled nucleic acid that comprises fragments which are substantially complementary to nucleic acid segments within the chromosomal DNA for which detection is desired, from which high copy repetitive nucleic acid sequences or genomic DNA that comprises fragments which are substantially complementary to repetitive segments have been removed; and
    employing said labeled nucleic acid and chromosomal DNA in in situ hybridization so that hybridization of unique segments within the labeled nucleic acid to the chromosomal DNA is allowed, wherein removal of the repetitive segments from the labeled nucleic acid is sufficient to permit detection of hybridized labeled nucleic acid containing unique segments, and wherein the chromosomal DNA is present in a morphologically identifiable chromosome or cell nucleus during the in situ hybridization;

wherein the detection of unique segments in the chromosomal DNA indicates structurally aberrant chromosomes and the frequency of structurally aberrant chromosomes is measured to determine level of genetic damage suffered by a subject, wherein a translocation is discriminated from a dicentric by adding to the probe at least one sequence found at all of the chromosome centromeres.

11. The method according to claim 10, wherein the sequence found at the chromosome centromeres is differently labeled from that of the labeled nucleic acid which hybridizes to the unique segments of the chromosomal DNA.

12. The method according to claim 11, wherein the centromere sequence and the labeled nucleic acid are differently labeled by color.

13. The method according to claim 10, wherein said fragments of labeled nucleic acid are labeled using more than one color.

* * * * *